(12) United States Patent
Bourke, Jr. et al.

(10) Patent No.: US 10,201,796 B2
(45) Date of Patent: *Feb. 12, 2019

(54) PLASMONIC ASSISTED SYSTEMS AND METHODS FOR INTERIOR ENERGY-ACTIVATION FROM AN EXTERIOR SOURCE

(71) Applicants: IMMUNOLIGHT, LLC., Detroit, MI (US); DUKE UNIVERSITY, Durham, NC (US)

(72) Inventors: Frederic Avery Bourke, Jr., Greenwich, CT (US); Tuan Vo-Dinh, Chapel Hill, NC (US)

(73) Assignees: IMMUNOLIGHT, LLC., Detroit, MI (US); DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,656

(22) Filed: Feb. 27, 2017

(65) Prior Publication Data

US 2017/0173350 A1 Jun. 22, 2017

Related U.S. Application Data

(63) Continuation of application No. 14/165,026, filed on Jan. 27, 2014, now Pat. No. 9,630,022, which is a (Continued)

(51) Int. Cl.
*A61N 5/00* (2006.01)
*A23L 3/26* (2006.01)
(Continued)

(52) U.S. Cl.
CPC ............. *B01J 19/123* (2013.01); *A23L 2/50* (2013.01); *A23L 3/26* (2013.01); *A23L 3/263* (2013.01); *A23L 3/28* (2013.01); *A23L 5/32* (2016.08); *A61K 41/0057* (2013.01); *A61K 41/0066* (2013.01); *A61L 2/0011* (2013.01); *A61L 2/0047* (2013.01); *A61L 2/0076* (2013.01); *A61L 2/082* (2013.01); *A61L 2/088* (2013.01); *A61L 2/10* (2013.01); *A61L 2/16* (2013.01); *A61M 1/3683* (2014.02); *A61N 5/062* (2013.01); *A61N 5/0624* (2013.01); *A61N 5/10* (2013.01); *B01J 19/082* (2013.01); *B01J 19/085* (2013.01); *B01J 19/12* (2013.01); *B01J 19/125* (2013.01); *B01J 19/127* (2013.01); *B01J 19/128* (2013.01); *B01J 23/50* (2013.01); *B01J 23/52* (2013.01); *B01J 31/0275* (2013.01); *B01J 31/2295* (2013.01); *B01J 35/004* (2013.01); *B01J 35/0006* (2013.01); *B01J 35/0013* (2013.01); *B01J 37/0072* (2013.01); *B01J 37/0221* (2013.01); *C02F 1/30* (2013.01); *C02F 1/305* (2013.01); *C02F 1/307* (2013.01); *C02F 1/32* (2013.01); *C02F 1/725* (2013.01); *C08J 3/24* (2013.01); *C08J 3/28* (2013.01); *C08J 7/18* (2013.01); *C09D 201/00* (2013.01); *C09J 5/00* (2013.01); *C09J 201/00* (2013.01); *C12H 1/06* (2013.01); *G02B 5/008* (2013.01); *G21K 5/00* (2013.01); *A23V 2002/00* (2013.01);
(Continued)

(58) Field of Classification Search
CPC ... A23L 2/50; A23L 3/26; A23L 3/262; A23L 3/28; A61N 5/10; A61N 5/0262; A61N 5/0624; A61M 1/3683; A61K 41/0057; A61K 41/0066; A61L 2/0011; A61L 2/0047; A61L 2/0076; A61L 2/082; A61L 2/088; A61L 2/16; A61L 2/10; B01J 19/082; B01J 19/085; B01J 19/19812; B01J 19/123; B01J 19/125; B01J 19/127; B01J 19/128; B01J 21/16; B01J 21/10; C02F 1/30; C02F 1/305; C02F 1/351; C02F 1/352; C02F 1/725
See application file for complete search history.

(56) References Cited

U.S. PATENT DOCUMENTS 2,721,941 A  10/1955  McMaster et al.
4,111,890 A  9/1978   Getson et al.
(Continued)

FOREIGN PATENT DOCUMENTS

CN  1270186 A  10/2000
CN  1463286 A  12/2003
(Continued)

OTHER PUBLICATIONS

K. Jensen, J. Weldon, H. Garcia, and A. Zettl, "Nanotube Radio," *Nano Lett.*, vol. 7, No. 11, 3508-3511 (2007).
(Continued)

*Primary Examiner* — Sanza L. McClendon
(74) *Attorney, Agent, or Firm* — Oblon, McClelland, Maier & Neustadt, L.L.P.

(57) ABSTRACT

A method and a system for producing a change in a medium disposed in an artificial container. The method places in a vicinity of the medium at least one of a plasmonics agent and an energy modulation agent. The method applies an initiation energy through the artificial container to the medium. The initiation energy interacts with the plasmonics agent or the energy modulation agent to directly or indirectly produce the change in the medium. The system includes an initiation energy source configured to apply an initiation energy to the medium to activate the plasmonics agent or the energy modulation agent.

44 Claims, 30 Drawing Sheets

Related U.S. Application Data continuation of application No. 13/713,931, filed on Dec. 13, 2012, now Pat. No. 9,004,131, which is a continuation of application No. 12/401,478, filed on Mar. 10, 2009, now Pat. No. 8,376,013.

(60) Provisional application No. 61/080,140, filed on Jul. 11, 2008, provisional application No. 61/035,559, filed on Mar. 11, 2008.

(51) Int. Cl.

| | | |
|---|---|---|
| *A61L 2/00* | (2006.01) | |
| *B01J 19/12* | (2006.01) | |
| *B01J 19/08* | (2006.01) | |
| *C02F 1/30* | (2006.01) | |
| *C02F 1/72* | (2006.01) | |
| *A61L 2/08* | (2006.01) | |
| *A61L 2/10* | (2006.01) | |
| *A61L 2/16* | (2006.01) | |
| *C08J 3/28* | (2006.01) | |
| *G21K 5/00* | (2006.01) | |
| *C02F 1/32* | (2006.01) | |
| *A61K 41/00* | (2006.01) | |
| *A61N 5/06* | (2006.01) | |
| *A61N 5/10* | (2006.01) | |
| *A23L 5/30* | (2016.01) | |
| *B01J 23/50* | (2006.01) | |
| *B01J 23/52* | (2006.01) | |
| *B01J 31/02* | (2006.01) | |
| *B01J 31/22* | (2006.01) | |
| *B01J 35/00* | (2006.01) | |
| *B01J 37/00* | (2006.01) | |
| *B01J 37/02* | (2006.01) | |
| *C09D 201/00* | (2006.01) | |
| *C09J 5/00* | (2006.01) | |
| *C09J 201/00* | (2006.01) | |
| *A23L 2/50* | (2006.01) | |
| *A23L 3/28* | (2006.01) | |
| *C08J 3/24* | (2006.01) | |
| *C08J 7/18* | (2006.01) | |
| *G02B 5/00* | (2006.01) | |
| *A61M 1/36* | (2006.01) | |
| *C12H 1/06* | (2006.01) | |
| *B82Y 20/00* | (2011.01) | |
| *B82Y 30/00* | (2011.01) | |
| *B82Y 40/00* | (2011.01) | |

(52) U.S. Cl.
CPC ....... *A61L 2202/21* (2013.01); *A61L 2202/22* (2013.01); *A61N 2005/0661* (2013.01); *A61N 2005/0662* (2013.01); *A61N 2005/1087* (2013.01); *A61N 2005/1089* (2013.01); *A61N 2005/1098* (2013.01); *B01J 2219/0877* (2013.01); *B01J 2219/0879* (2013.01); *B01J 2219/0892* (2013.01); *B01J 2219/1203* (2013.01); *B01J 2231/005* (2013.01); *B01J 2531/005* (2013.01); *B01J 2531/008* (2013.01); *B82Y 20/00* (2013.01); *B82Y 30/00* (2013.01); *B82Y 40/00* (2013.01); *C02F 1/302* (2013.01); *C02F 2305/10* (2013.01); *C08J 2300/00* (2013.01); *C09J 2205/31* (2013.01); *Y02W 10/37* (2015.05); *Y10S 977/774* (2013.01); *Y10S 977/777* (2013.01); *Y10S 977/896* (2013.01); *Y10S 977/915* (2013.01); *Y10T 156/10* (2015.01)

(56) References Cited

U.S. PATENT DOCUMENTS

| | | |
|---|---|---|
| 4,482,778 A | 11/1984 | Anderson |
| 4,675,346 A | 6/1987 | Lin et al. |
| 5,118,422 A | 6/1992 | Cooper et al. |
| 5,323,442 A | 6/1994 | Golovanivsky et al. |
| 5,632,057 A * | 5/1997 | Lyden .......... A43B 3/0063 12/146 B |
| 6,051,625 A | 4/2000 | Harkness et al. |
| 6,087,141 A | 7/2000 | Margolis-Nunno et al. |
| 6,281,261 B1 | 8/2001 | Bennington |
| 6,323,253 B1 | 11/2001 | Bennington |
| 6,344,272 B1 | 2/2002 | Oldenburg et al. |
| 6,627,923 B1 | 9/2003 | Lipson et al. |
| 6,727,508 B1 | 4/2004 | Tominaga et al. |
| 6,750,266 B2 | 6/2004 | Bentsen et al. |
| 7,005,229 B2 | 2/2006 | Nirmal et al. |
| 7,008,559 B2 | 3/2006 | Chen |
| 7,014,988 B2 | 3/2006 | DeVoe et al. |
| 7,091,255 B2 | 8/2006 | DeVoe |
| 7,208,890 B2 | 4/2007 | Zavadtsev et al. |
| 7,265,161 B2 | 9/2007 | Leatherdale et al. |
| 7,267,948 B2 | 9/2007 | Vo-Dinh |
| 7,294,656 B2 | 11/2007 | Bach et al. |
| 7,297,374 B1 | 11/2007 | Amey et al. |
| 7,381,516 B2 | 6/2008 | Arney et al. |
| 7,601,484 B2 | 10/2009 | DeVoe et al. |
| 7,790,347 B2 | 9/2010 | Leatherdale et al. |
| 8,038,991 B1 * | 10/2011 | Stankus .......... A61K 31/00 424/530 |
| 8,236,239 B2 | 8/2012 | Bernstein |
| 8,376,013 B2 | 2/2013 | Bourke, Jr. et al. |
| 8,927,615 B2 | 1/2015 | Bourke, Jr. et al. |
| 9,004,131 B2 * | 4/2015 | Bourke, Jr. .......... A23L 3/26 156/349 |
| 9,358,292 B2 * | 6/2016 | Bourke, Jr. .......... A61K 47/02 |
| 9,630,022 B2 * | 4/2017 | Bourke, Jr. .......... A23L 3/26 |
| 2002/0045675 A1 | 4/2002 | Halas et al. |
| 2002/0161065 A1 | 10/2002 | DiTizio et al. |
| 2003/0016780 A1 | 1/2003 | Matsuo et al. |
| 2003/0139484 A1 | 7/2003 | Bentsen et al. |
| 2003/0219785 A1 | 11/2003 | Hallahan et al. |
| 2004/0067431 A1 | 4/2004 | Arney et al. |
| 2004/0198857 A1 | 10/2004 | Dejneka et al. |
| 2004/0253138 A1 | 12/2004 | Malak |
| 2005/0020869 A1 | 1/2005 | Hainfeld et al. |
| 2005/0031077 A1 | 2/2005 | Avnery |
| 2005/0276382 A1 | 12/2005 | Lesiak et al. |
| 2006/0011862 A1 | 1/2006 | Bernstein |
| 2007/0018140 A1 | 1/2007 | Lee et al. |
| 2007/0063154 A1 | 3/2007 | Chen et al. |
| 2007/0153283 A1 | 7/2007 | Tsao et al. |
| 2007/0178133 A1 | 8/2007 | Rolland |
| 2007/0217996 A1 | 9/2007 | Levy et al. |
| 2007/0218049 A1 | 9/2007 | Chen et al. |
| 2008/0004364 A1 | 1/2008 | Huo et al. |
| 2008/0248001 A1 | 10/2008 | Bourke |
| 2009/0130169 A1 | 5/2009 | Bernstein |
| 2009/0263744 A1 | 10/2009 | Kuroki |
| 2010/0261263 A1 | 10/2010 | Vo-Dinh et al. |
| 2013/0156905 A1 | 6/2013 | Bourke, Jr. et al. |
| 2014/0163303 A1 | 6/2014 | Bourke, Jr. et al. |
| 2014/0222117 A1 | 8/2014 | Bourke, Jr. et al. |

FOREIGN PATENT DOCUMENTS

| | | |
|---|---|---|
| CN | 1950111 A | 4/2007 |
| CN | 1981360 A | 6/2007 |
| CN | 101035827 A | 9/2007 |
| EP | 1 353 179 A1 | 10/2003 |
| EP | 1 355 193 A2 | 10/2003 |
| EP | 1 376 021 A1 | 1/2004 |
| EP | 1 870 478 A1 | 12/2007 |
| EP | 2 265 366 | 12/2010 |
| EP | 2 711 075 A2 | 3/2014 |
| GB | 2300421 A | 11/1996 |

(56) References Cited

FOREIGN PATENT DOCUMENTS

| | | |
|---|---|---|
| JP | 50-83698 | 7/1975 |
| JP | 57-24944 A | 2/1982 |
| JP | 57-138634 | 8/1982 |
| JP | 58-183940 | 10/1983 |
| JP | 59-4436 | 1/1984 |
| JP | 60-186575 A | 9/1985 |
| JP | 2-36931 | 2/1990 |
| JP | 2-36931 A | 2/1990 |
| JP | 4-206709 | 7/1992 |
| JP | 6-39045 A | 2/1994 |
| JP | 8-217982 A | 8/1996 |
| JP | 9-12650 | 1/1997 |
| JP | 10-11822 A | 1/1998 |
| JP | H1011822 A1 * | 1/1998 |
| JP | 2001-501380 | 1/2001 |
| JP | 2001-46488 A | 2/2001 |
| JP | 2001-181620 A | 7/2001 |
| JP | 2001-513198 | 8/2001 |
| JP | 2001-334262 | 12/2001 |
| JP | 2002-503522 | 2/2002 |
| JP | 2002-69442 | 3/2002 |
| JP | 2002-69442 A | 3/2002 |
| JP | 2002-214142 | 7/2002 |
| JP | 2002-286251 | 10/2002 |
| JP | 2002-346394 A | 12/2002 |
| JP | 2003-331433 | 1/2003 |
| JP | 2003-265498 A | 9/2003 |
| JP | 2003-313208 A | 11/2003 |
| JP | 2004-505734 | 2/2004 |
| JP | 2005-138440 A | 6/2005 |
| JP | 2005-523231 A | 8/2005 |
| JP | 2006-502756 A | 1/2006 |
| JP | 2006-298908 A | 11/2006 |
| JP | 2006-323908 A | 11/2006 |
| JP | 2007-23221 | 2/2007 |
| JP | 2007-23221 A | 2/2007 |
| JP | 2007-104939 | 4/2007 |
| JP | 2007-156184 A | 6/2007 |
| JP | 2007-171158 A | 7/2007 |
| JP | 2007-536356 A | 12/2007 |
| JP | 2013-82943 A | 5/2013 |
| WO | WO 98/37417 | 8/1998 |
| WO | WO 98/54929 A1 | 12/1998 |
| WO | WO 99/42142 | 8/1999 |
| WO | WO 02/13905 A1 | 2/2002 |
| WO | WO 2004/022483 A1 | 3/2004 |
| WO | WO 2006/013944 A1 | 2/2006 |
| WO | WO 2007/072689 A1 | 6/2007 |
| WO | WO 2009/114567 A1 | 9/2009 |

OTHER PUBLICATIONS

Douglas D. Young and Alexander Deiters, "Photochemical Hammerhead Ribozyme Activation", *Bioorganic & Medicinal Chemistry Letters*, 16(10) ,pp. 2658-2661 (2006).

Hirsch, L.R., Stafford , R.J., Bankson, J.A. , Sershen, S.R., Rivera, B., Price, R.E., Hazle, J. D., Halas, N. J., and West, J. L., *Nanoshell-mediated near-infrared thermal therapy of tumors under magnetic resonance guidance.* PNAS, 2003. 100(23): p. 13549-13554.

Xiaohua Huang & Prashant K. Jain & Ivan H. El-Sayed & Mostafa A. El-Sayed, Plasmonic photothermal therapy (PPTT) using gold nanoparticles, *Lasers in Medical Science*, Aug. 2007.

Mircea Cotlet, Tom Vosch, Satoshi Habuchi, Tanja Weil, Klaus Mullen, Johan Hoftens, and Frans De Schryver, "*Probing intramolecular Forster Resonance Energy Transfer in a Naphthaleneimide-Peryleneimide-Terrylenediimide-Based Dendrimer by Ensemble and Single-Molecule Fluorescence Spectroscopy*", J. Am. Chem. Soc. 2005, 127, 9760-9768.

M.O. Guler, "Singlet-Singlet and Triplet-Triplet Energy Transfer in Bichromophoric Cyclic Peptides," Worcester Polytechnic Institute, May 18, 2002.

Young and Deiters in "Photochemical Control of Biological Processes", *Org. Biomol. Chem.*, 5, pp. 999-1005 (2007).

T. Vo-Dinh, M.Y.K. Hiromoto, G. M. Begun and R. L. Moody, "Surface-enhanced Raman spectroscopy for trace organic analysis," *Anal. Chem.*, vol. 56, 1667, 1984.

M. M. Kerker, Electromagnetic Model for Surface-Enhanced Raman Scattering (SERS) on Metal Colloids, *Acc. Chem. Res.*, 17, 370 (1984).

T. Vo-Dinh, "Surface-Enhanced Raman Spectroscopy Using Metallic Nanostructures," *Trends in Anal. Chem.*, 17,557 (1998).

J. B. Jackson, S. L. Westcott, L. R. Hirsch, J. L. West and N. H. Halas, "Controlling the surface enhanced Raman effect via the nanoshell geometry," *Appl. Phys. Lett.*, vol. 82, 257-259, 2003.

S. J. Norton and T. Vo-Dinh, "Plasmonic Resonances of nanoshells of Spheroidal Shape", *IEEE Trans. Nanotechnology*, 6, 627-638 (2007).

R. Eighanian, J.J. Storhoff, R.C. Mucic, R.L. Letsinger and C.A. Mirkin, Selective colorimetric detection of polynucleotides based on the distance-dependent optical properties of gold nanoparticles. *Science* 277 (1997), pp. 1078-1081.

Z. Li, R.C. Jin, C.A. Mirkin and R.L. Letsinger, Multiple thiol-anchor capped DNA-gold nanoparticle conjugates. *Nucleic Acids Res.* 30 (2002), pp. 1558-1562.

Y.W. Cao, R. Jin and C.A. Mirkin, DNA-modified core-shell Ag/Au nanoparticles. *J. Am. Chem. Soc.* 123 (2001), pp. 7961-7962.

Burgess, J. D.; Hawkridge, F. M., "*Octadecyl Mercaptan Submonolayers on Silver Electrodeposited on Gold Quartz Crystal Microbalance Electrodes*", Langmuir 1997, 13, 3781-6.

Hainfeld et al, Gold nanoparticles: a new X-ray contrast agent, *The British Journal of radiology*, 79, 248, 2006.

Ma et al, DNA-Passivated CdS Nanocrystals : Luminescence, Bioimaging, and Toxicity Profiles, *Langmuir*, 23 (26), 12783-12787 (2007).

Hua et al, Soft x-ray excited optical luminescence : Some recent applications, *Rev. Sci. Instrum.*, 73. 1379, 2002.

Jaegle et al, Ultraviolet luminescence of CsI and CsCl excited by soft x-ray laser, *J. Appl. Phys.*, 81, 2406, 1997.

Kun Chen, Yang Liu, Guillermo Ameer, Nadia Backman, Optimal design of structured nanospheres for ultrasharp light-scattering resonances as molecular imaging multilabels, *Journal of Biomedical Optics*, 10(2), 024005 (Mar./Apr. 2005).

Mirkhin et al, X-ray excited luminescence of some molybdates, *Nuclear Instrum. Meth. In Physics Res. A*, 486, 295 (2002).

L. Soderholm, G. K. Liu, Mark R. Antonioc, F. W. Lytle, X-ray excited optical luminescence .XEOL. detection of x-ray absorption fine structure .XAFZ, *J. Chem. Phys*,109, 6745, 1998.

Masashi Ishiia, Yoshihito Tanaka and Tetsuya Ishikawa, Shuji Komuro and Takitaro Morikawa, Yoshinobu Aoyagi, Site-selective x-ray absorption fine structure analysis of an optically active center in Er-doped semiconductor thin film using x-ray-excited optical luminescence, *Appl. Phys. Lett*, 78, 183, Jan. 8, 2001.

Kuiru Li, Mark I., Stockman, and David J. Bergman, Self-Similar Chain of Metal Nanospheres as an Efficient Nanolens, *Physical Review Letter*, vol. 91, No. 22, 227402-1, 2003.

Frens, G., *Controlled nucleation for the regulation of the particle size in monodisperse gold solutions.* Nature (London) Phys Sci,, 1973. 241: p. 20-22.

Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, vol. 101, 1719-1729, 2007.

Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, vol. 35 (2006), No. 10 p. 1192.

Martin Nikl, Scintillation detectors for x-rays, *Meas. Sci. Technol.* 17 (2006) R37-R54.

Kadshchuk, A. K., Ostapenko, N. I., Skryshevskii, Yu. A., Sugakov, V. I. and Susokolova, T. O., Clusters of Dipole Charge-Carrier Capture Centers in Organic Crystals, *Mol. Cryst. and Liq. Cryst.*, 201, 167 (1991) t.

S. V. Izvekov, V. I. Sugakov, Exciton and Electron Traps on Structural Defects in Molecular Crystals with Dipolar Molecules, *Physica Scripta.* vol. T66, 255-257, 1996.

(56) References Cited

OTHER PUBLICATIONS

A. P. D'Silva, G. J. Oestreich, and V. A. Fassel, X-ray excited optical luminescence of polynuclear aromatic hydrocarbons, *Anal. Chem.*; 1976, 48(6) pp. 915-917.

T. Vo-Dinh, Multicomponent analysis by synchronous luminescence spectrometry, *Anal. Chem.*; 1978; 50(3) pp. 396-401.

J. Bellessa,* C. Bonnand, and J. C. Plenet, J. Mugnier, Strong Coupling between Surface Plasmons and Excitons in an Organic Semiconductor, *Phys. Rev. Lett*, 93 (3), 036404-1, 2004.

Alexander O. Govorov, Garnett W. Bryant,‡ Wei Zhang, Timur Skeini, Jaebeom Lee,§ Nicholas A. Kotov, Joseph M. Slocik,| and Rajesh R. Naik, Exciton-Plasmon Interaction and Hybrid Excitons in Semiconductor-Metal Nanoparticle Assemblies, *Nano Lett.*, vol. 6, No. 5, 984, 2006.

I.V. Bondarev, K. Tatur and L.M. Woods, *Strong exciton-plasmon coupling in semiconducting carbon nanotube*, Jul. 8, 2009 Accepted paper in Physical Review B.

Yuri Fedutik, Vasily Temnov, Ulrike Woggon, Elena Ustinovich and Mikhail Artemyev , Exciton-Plasmon Interaction in a Composite Metal-Insulator-Semiconductor Nanowire System, *J. . Am. Chem. Soc.*, 129 (48), 14939-14945, 2007.

G.W. Ford and W. H. Weber, Electromagnetic interactions of molecules with metal surfaces. *Phys. Rep.* 113, 195-287 (1984).

Gregory A. Wurtz,* Paul R. Evans, William Hendren, Ronald Atkinson, Wayne Dickson, Robert J. Pollard, and Anatoly V. Zayats, Molecular Plasmonics with Tunable Exciton-Plasmon Coupling Strength in J-Aggregate Hybridized Au Nanorod Assemblies, *Nano Lett.*, vol. 7, No. 5, 1297, 2007.

Jaebeom Lee, Alexander O. Govorov, John Dulka, and Nicholas A. Kotov, Bioconjugates of CdTe Nanowires and Au Nanoparticles: Plasmon-Exciton Interactions, Luminescence Enhancement, and Collective Effects, *Nano Lett*, vol. 4, No. 12, 2323, 2004.

N.R. Jana, L. Gearheart and C.J. Murphy, Seeding growth for size control of 5-40 nm diameter gold nanoparticles. *Langmuir* 17 (2001), pp. 6782-6786.

Brust, M.; Walker, M.; Bethell, D.; Schiffrin, D. J.; Whyman, R., *Synthesis of Thiol-derivatised Gold Nanoparticles in a Two-phase Liquid-Liquid System Chem. Commun.* 1994, 801.

Hostetler, M.J.; Wingate, J. E.; Zhong, C. J.; Harris, J. E.; Vachet, R. W.; Clark, M. R.; Londono, J. D.; Green, S. J.; Stokes, J. J.; Wignall, G. D.; Glish, G. L.; Porter, M. D.; Evans, N. D.; Murray, R. W., Alkanethiolate Gold Cluster Molecules with Core Diameters from 1.5 to 5.2 nm: Core and Monolayer Properties as a Function of Core Size, *Langmuir* 1998, 14, 17.

Schmid, G.; Pfeil, R.; Boese, R.; Bandrmann, F.; Meyer, S.; Calis, G. H. M.; van der Velden, J. W. A., $Au_{55}[P(C_5H_5)_3]_{12}Cl_6$-ein Goldcluster ungewohnlicher Größe, *Chem. Ber.* 1981, 114, 3634; with English Abstract.

Warner, M. G.; Reed, S. M.; Hutchison, J. E., Small, Water-Soluble, Ligand-Stabilized Gold Nanoparticles Synthesized by Interfacial Ligand Exchange Reactions, *Chem. Mater.* 2000,12, 3316.

Weare, W. W.; Reed, S. M.; Warner, M. G.; Hutchison, J. E., Improved Synthesis of Small ($d_{CORE} \approx$ 1.5 nm) Phosphine-Stabilized Gold Nanoparticles, *J. Am. Chem. Soc.* 2000, 122, 12890.

Ziyi Zhong, Benoit Male, Keith B. Luong, John H.T., More Recent Progress in the Preparation of Au Nanostructures, Properties, and Applications, *Analytical Letters*; 2003, vol. 36 Issue 15, p. 3097-3118.

Akito Masuhara, Satoshi Ohhashi, Hitoshi Kasai; Shuji Okada, Fabrication and Optical Properties of Nanocomplexes Composed of Metal Nanoparticles and Organic Dyes, *Journal of Nonlinear Optical Physics & Materials* vol. 13, Nos. 3 & 4 (2004) 587-592.

Wang et al. in "Electromagnetic excitation of nano-carbon in vacuum," in Optics Express, vol. 13, No. 10, May 10, 2005.

Aslan et al. in "Multicolor Microwave-Triggered Metal-Enhanced Chemiluminescence," in J. Am. Chem. Soc. published on Web Sep. 23, 2006.

M. A. Correa-Duarte, M. Giesig, and L. M. Liz-Marzan, Stabilization of CdS semiconductor nanoparticles against photodegradation by a silica coating procedure, Chem. Phys. Lett., 1998, 286: 497.

M. Thoms, H. von Seggern, *Method for the determination of photostimulable defect center concentrations, production rates, and effective formation energies*, J. Appl. Phys. 1994, 75: 4658-4661.

W. Chen, S. P. Wang, S. Westcott, J. Zhang, A. G. Joly, and D. E. McCready, Structure and luminescence $BaFBr:Eu^{2+}$ and $BaFBr:Eu^{2+}$, $Tb^{3+}$ phosphors and thin films, J. Appl. Phys. 2005, 97: 083506.

Mai Thu Thi Tran, Mohammed Farid, "Ultraviolet Treatment of Orange Juice" published in Innovative Food Science & Emerging Technologies (vol. 5, Issue 4, Dec. 2004, pp. 495-502).

Santos et al, *Photocatalysts as a Tertiary Treatment for Petroleum Refinery Wastewaters*, Braz. J. Chem. Eng. vol. 23, No. 4, 2006.

Spatio-Resolved Hyperbranched Graft Polymerized Surfaces by Iniferter-Based Photograft Copolymerization, *Langmuir*, 2002, 18 (7), pp. 2601-2606.

Pettinger B., U. Wenneng, and H. Wetzel, Surface-plasmon enhanced Raman-scattering Frequency and Angular Resonance of Raman Scattered Light From Pyridine on Au, Ag and Cu Electrodes, 1980, Surf Sci., 101, 409.

Fleishman M., P. R. Graves, and J. Robinson, *The Raman-Spectroscopy of the Ferricyanide/Ferrocyanide System at Gold, β-Palladium Hydride and Platinum Electrodes*, 1985, J. Electroanal. Chem., 182, 87.

Miller S. K., A. Baiker, M. Meier, and A. Wokaun, *Surface-enhanced Raman scattering and the preparation of copper substrates for catalytic studies*, 1984, J. Chem. Soc. Farad. Trans. I, 80, 1305.

Taranenko N., J.P. Alarie, D.L. Stokes, and T. Vo Dinh, *Surface-Enhanced Raman Detection of Nerve Agent Simulant (DMMP and DIMP) Vapor on Electrochemically Prepared Silver Oxide Substrates*, 1996, J. Raman Spectr., 27, 379-384.

Jennings C., R. Aroca, A. M. Hor, and R. O. Loutfy, *Surface-enhanced Raman scattering from copper and zinc phthalocyanine complexes by silver and indium island films*, 1984, Anal. Chem., 56, 203.

Ni F., R. Sheng, and T. M. Cotton, *Flow-injection analysis and real-time Detection of RNA bases by surface-enhanced Raman-spectroscopy*, 1990, Anal. Chem., 62, 1958.

Moody R. L., T. Vo Dinh, and W. H. Fletcher, *Investigation of Experimental Parameters for Surface-Enhanced Raman Scattering (SERS) Using Silver-Coated Microsphere Substrates*, 1987, Appl. Spectr., 41, 966.

Bello J. M., D. L. Stokes and T. Vo Dinh, *Silver-Coated Alumina as a New Medium for Surface-Enhanced Raman Scattering Analysis*, 1989, Appl. Spectrosc., 43. 1325.

Sutherland, *A Portable Surface-Enhanced Raman Spectrometer*, Instrumentation Science & Technology, vol. 22, Issue 3 Aug. 1994, pp. 231-239.

Alak A., and T. Vo Dinh, *Silver-Coated Fumed Silica as New Substrate Materials for Surface-Enhanced Raman Scattering*, 1989, Anal. Chem., 61, 656.

Liao P. F., and M. B. Stern, *Surface-enhanced Raman scattering on gold and aluminum particle arrays*, 1982, Opt. Lett., 7, 483.

Vo Dinh T., M. Meier, and A. Wokaun, 1986, *Surface Enhanced Raman Spectroscopy with Silver Particles on Stochastic Post Substrates*, Anal. Chim. Acta, 181, 139.

Enlow P. D., M. C. Buncick, R. J. Warmack, and T. Vo Dinh *Detection of Nitro polynuclear Aromatic Compounds by Surface Enhanced Raman Spectroscopy*, 1986, Anal. Chem., 58, 1119.

Vo Dinh T., 1989, *Surface-Enhanced Raman Spectrometry, in Chemical Analysis of Polycyclic Aromatic Compounds*, Wiley, T. Vo-Dinh, Ed., New York.

M. Volkan, D.L. Stokes and T. Vo-Dinh, *A Sol-Gel Derived AgCl Photochromic Coaling on Glass for SERS Chemical Sensor Application*, Sensors and Actuators B, 106, 660-667 (2004).

M. Venkataraman, "Effects of Cryopreservation on Immune Responses" Cryobiology 34, Article No. CY972005, 1997, pp. 276-283.

Douglas D. Young, et al. "Photochemical control of biological processes" Organic & Biomolecular Chemistry,vol. 5, Dec. 20, 2006, pp. 999-1005.

(56) References Cited

OTHER PUBLICATIONS

Kadir Aslan, et al. "Multicolor Microwave-Triggered Metal-Enhanced Chemiluminescence" JACS Communications, Journal of the American Chemical Society,Sep. 2006, pp. 13372-13373.
Shaomin Wang, et al. "Electromagnetic excitation of nano-carbon in vacuum" Optics Express, vol. 13, No. 10, May 16, 2005, pp. 3625-3630.
Rahul M. Rasal, et al. "Effect of the Photoreaction Solvent on Surface and Bulk Properties of Poly(lactic acid) and Poly(hydroxyalkanoate) Films" Journal of Biomedical Material Research Part B: Applied Biometerials, 2007, pp. 564-572.
Office Action dated Jul. 22, 2014 in Japanese Patent Application No. 2013-015222 (with English language translation).
Notice of Reasons for Rejection dated Jul. 31, 2012 in Japanese Patent Application No. 2010-550826 (with English translation).
Steffi Artz et al., Automation of Macromolecular Crystallography Beamlines, Progress in Biophysics and Molecular Biology, Oct. 2005, vol. 89, Issue 2, pp. 124-152.
Combined Chinese Office Action and Search Report dated Jan. 30, 2013 in Patent Application No. 200980116914.1 (with English translation and translation of Categories of Cited Documents).
Search Report dated Mar. 20, 2013 in Chilean Patent Application No. 2009-000560 filed Mar. 10, 2009 (with English Translation of Categories of Cited Documents).
Office Action dated Feb. 26, 2013 in Japanese Patent Application No. 2013-015222 (with English-language translation).
Office Action dated Jul. 2, 2013 in the corresponding Japanese Patent Application No. 2010-550826 (with English Translation).
Decision of Rejection dated Sep. 3, 2013 in Japanese Patent Application No. 2013-015222 (w/English translation).
Office Action dated Oct. 16, 2013 in Chilean Patent Application No. 2009-000560 (with English translation of Categories of Cited Document).
Combined Chinese Office Action and Search Report dated Nov. 27, 2013 in Patent Application No. 200980116914.1 (with English language translation).
Combined Office Action and Search Report dated Dec. 26, 2013 in Taiwan Patent Application No. 098107921.
Combined Office Action and Search Report dated Mar. 17, 2014 in Chinese Patent Application No. 201310057456.7 with English language translation.
Notice of Reasons for Rejection dated Mar. 31, 2014 in Japanese patent Application No. 2013-015222 (with English translation).
Office Action dated Jun. 18, 2014 in Chinese Patent Application No. 200980116914.1 with English language translation.
Office Action dated May 26, 2014 in European Patent Application No. 13189150.9

Decision of Rejection dated Sep. 8, 2014 in Japanese Patent Application No. 2010-550826 with English language translation.
Decision to Reject the Amendments dated Sep. 8, 2014 in Japanese Patent Application No. 2010-550826 with English language translation.
Office Action dated Feb. 9, 2015 in Japanese Application No. 2013-272032 (with English language translation).
Extended Search Report dated Mar. 16, 2015 in European Patent Application No. 13 189 150.9
Combined Office Action and Search Report dated Apr. 15, 2015 in Canadian Patent Application No. 2,718,282.
Office Action dated Nov. 9, 2015 in Japanese Patent Application No. 2015-002427 (with English language translation).
Office Action dated Nov. 3, 2015 in European Patent Application No. 13 189 150.9.
Extended European Search Report issued in European Patent Application No. 097198279.9 dated Jun. 10, 2016.
Stewart M. et al., "Nanostructured Plasmonic Sensors", Chemical Reviews, American Chemical Society, US, vol. 108, No. 2, Feb. 1, 2006, pp. 494-521.
Notice of Reasons for Rejection issued in Japanese Patent Application No. 2013-272032 dated Jun. 6, 2016 (with English translation).
Notice of Reasons for Rejection issued in Japanese Patent Application No. 2015-002427 dated Aug. 8, 2016 (with English translation).
Office Action dated Nov. 20, 2015 in Japanese Patent Application No. 2013-272032 (with English language translation).
Notice of Reasons for Rejection dated Mar. 27, 2017 in Japanese Patent Application No. 2016-127329 (with English translation).
Office Action dated Nov. 20, 2017 in Japanese Patent Application No. 2013-272032 (with English language translation).
Japanese Office Action dated May 29, 2017 in Patent Application No. 2015-002427 (with English Translation).
T. Okamoto, et al., "Nonlinear Optical Response of Single Nano-Size Ag Particle Coated With CDS (2)", Proceedings of the 67th Autumn Meeting, 2006, the Japan Society of Applied Physics, No. 3, Extended Abstracts, issued by the Japan Society of Applied Physics, p. 947.
Japanese Office Action dated Dec. 11, 2017 in Japanese Patent Application No. 2017-042905, citing documents AO, AP and AQ therein, 17 pages(with English translation).
Office Action dated Aug. 27, 2018, in Japanese Patent Application No. 2013-0272032, filed Dec. 27, 2013—English translation only.
Office Action dated Nov. 5, 2018 in Japanese Patent Application No. 2017-042905, filed Mar. 7, 2017 w/English translation.

* cited by examiner

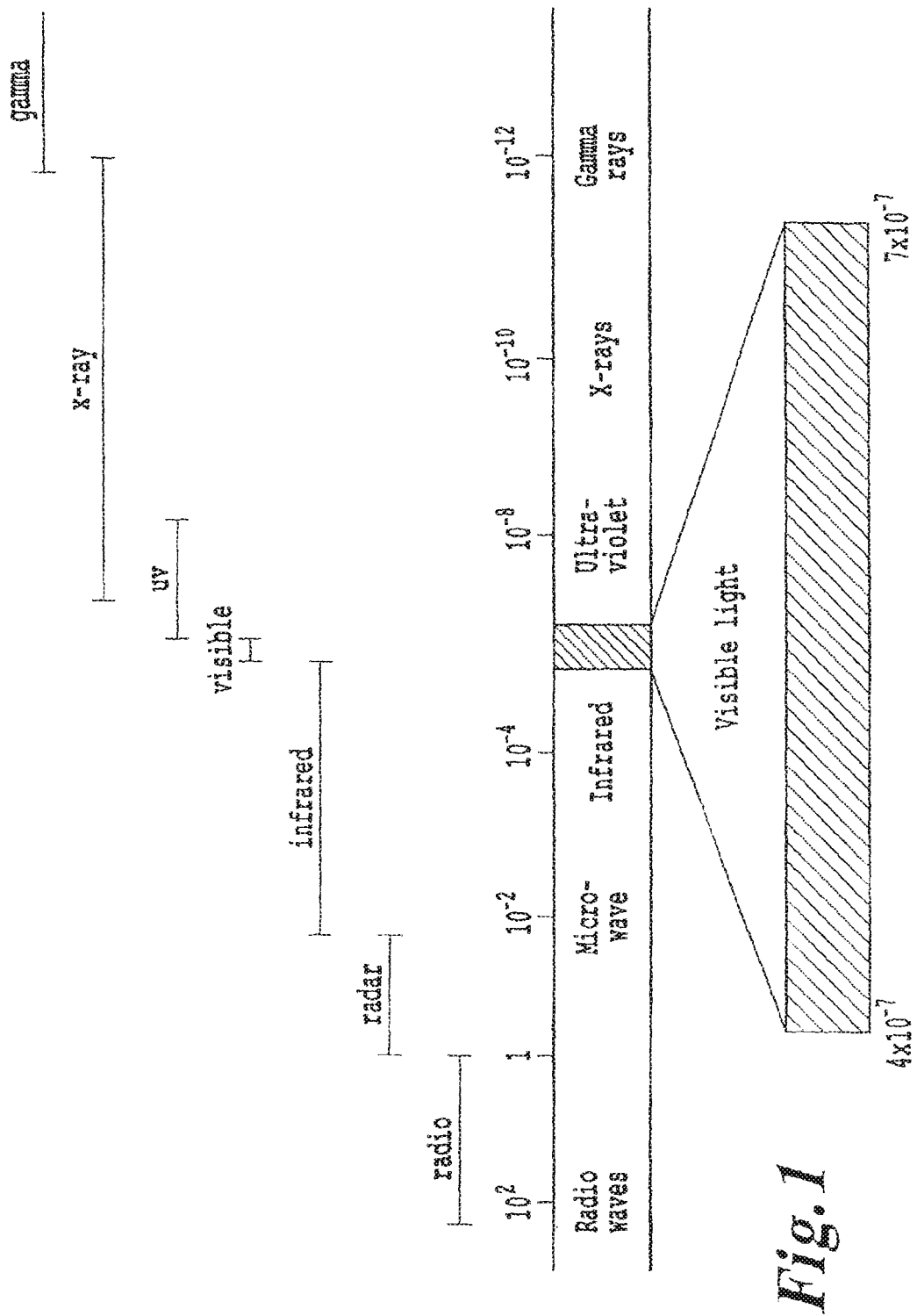

| ENDOGENOUS FLUOROPHORES | EXCITATION MAX. (nm) | EMISSION MAX. (nm) |
|---|---|---|
| Amino acids: | | |
| Tryptophan | 280 | 350 |
| Tyrosine | 275 | 300 |
| Phenylalanine | 260 | 280 |
| Structured Proteins: | | |
| Collagen | 325, 360 | 400 |
| Elastin | 290, 325 | 405 |
| Enzymes and Coenzymes: | | |
| flavine adenine dinucleatide | 450 | 535 |
| reduced nicotinamidedinucleotide | 290, 351 | 440, 460 |
| reduced nicotinamide dinucleotide phosphate | 336 | 464 |
| Vitamins: | | |
| Vitamin A | 327 | 510 |
| Vitamin K | 335 | 480 |
| Vitamin D | 390 | 480 |
| Vitamins $B_2$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

*Fig. 2*

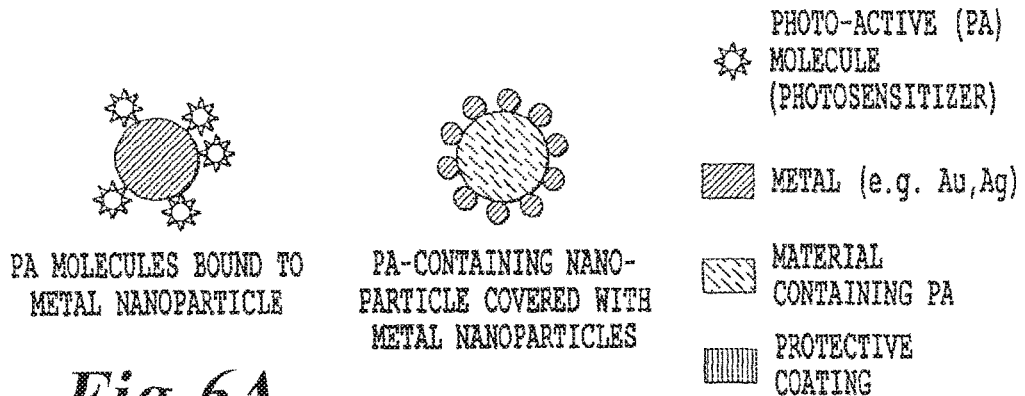

PA MOLECULES BOUND TO METAL NANOPARTICLE

*Fig. 6A*

PA-CONTAINING NANO-PARTICLE COVERED WITH METAL NANOPARTICLES

*Fig. 6B*

☆ PHOTO-ACTIVE (PA) MOLECULE (PHOTOSENSITIZER)

▨ METAL (e.g. Au, Ag)

▧ MATERIAL CONTAINING PA

▥ PROTECTIVE COATING

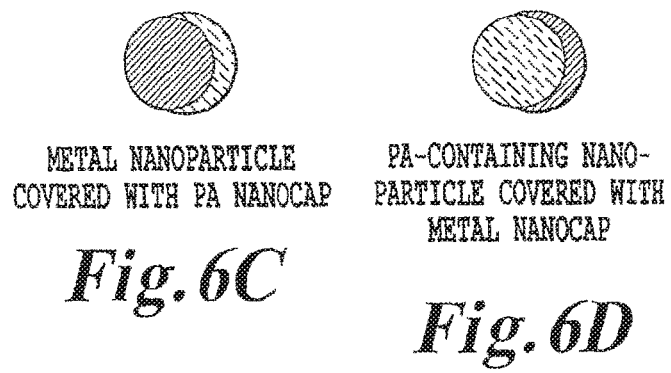

METAL NANOPARTICLE COVERED WITH PA NANOCAP

*Fig. 6C*

PA-CONTAINING NANO-PARTICLE COVERED WITH METAL NANOCAP

*Fig. 6D*

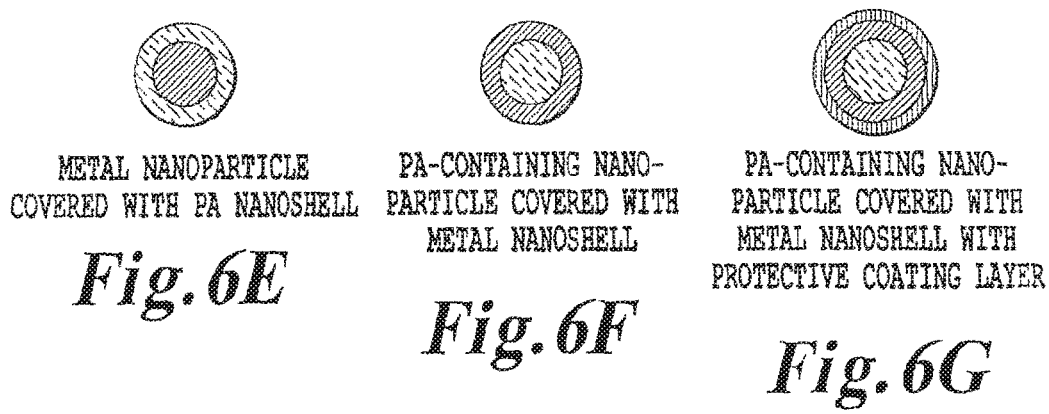

METAL NANOPARTICLE COVERED WITH PA NANOSHELL

*Fig. 6E*

PA-CONTAINING NANO-PARTICLE COVERED WITH METAL NANOSHELL

*Fig. 6F*

PA-CONTAINING NANO-PARTICLE COVERED WITH METAL NANOSHELL WITH PROTECTIVE COATING LAYER

*Fig. 6G*

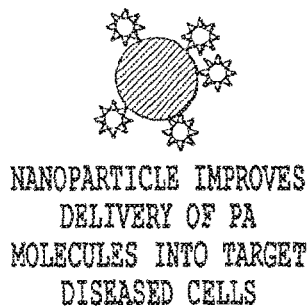
NANOPARTICLE IMPROVES DELIVERY OF PA MOLECULES INTO TARGET DISEASED CELLS
*Fig. 7A*
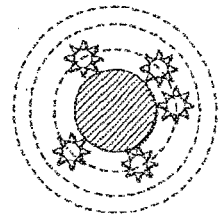

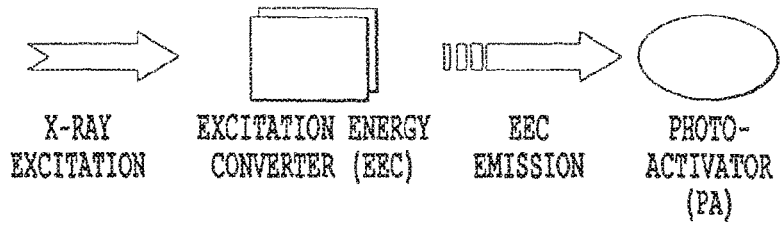

Fig. 11

PA MOLECULES BOUND TO
EEC AND TO PLASMONIC
METAL NANOPARTICLE

Fig. 12A

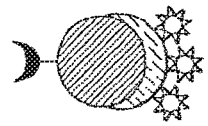

PLASMONIC AND METAL NANO-
PARTICLE WITH EEC NANOCAP
COVERED WITH PA MOLECULES

Fig. 12B

☆ PHOTO-ACTIVE (PA) MOLECULE (PHOTOSENSITIZER)

⊂ OPTIONAL BIORECEPTOR (Ab, DNA, etc)

▨ PLASMONICS-ACTIVE MATERIAL (e.g. Au, Ag)

▩ EXCITATION ENERGY CONVERTER (EEC) MATERIAL

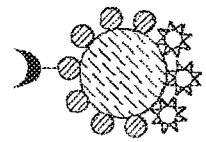

PA-COVERED NANOPARTICLE
WITH PLASMONIC METAL
NANOPARTICLES

Fig. 12C

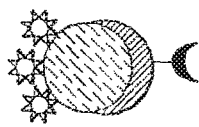

EEC-CONTAINING NANOPARTICLE
COVERED WITH PA MOLECULES AND
PLASMONIC METAL NANOCAP

Fig. 12D

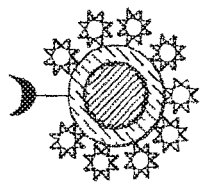

PLASMONIC METAL PARTICLE
CORE WITH EEC NANOSHELL
COVERED WITH PA MOLECULE

Fig. 12E

PA MOLECULE BOUND TO EEC (ATTACHED TO
PLASMONICS METAL NANOPARTICLE) NANOPARTICLE
BY DETACHABLE BIOCHEMICAL BOND

Fig. 12F

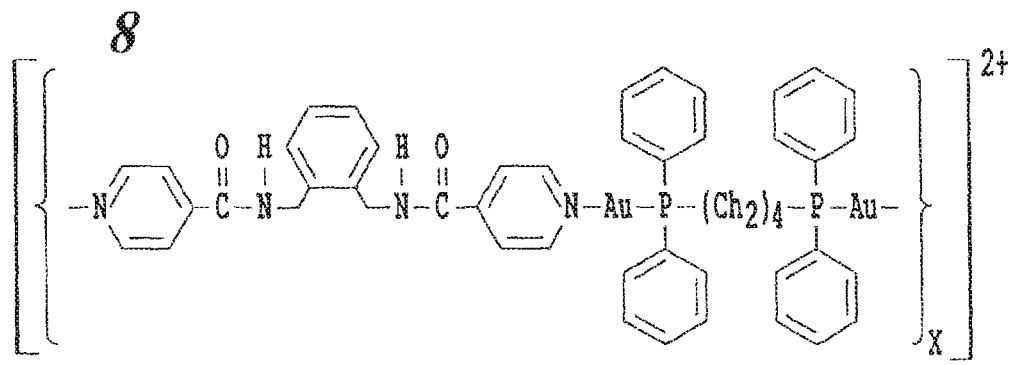
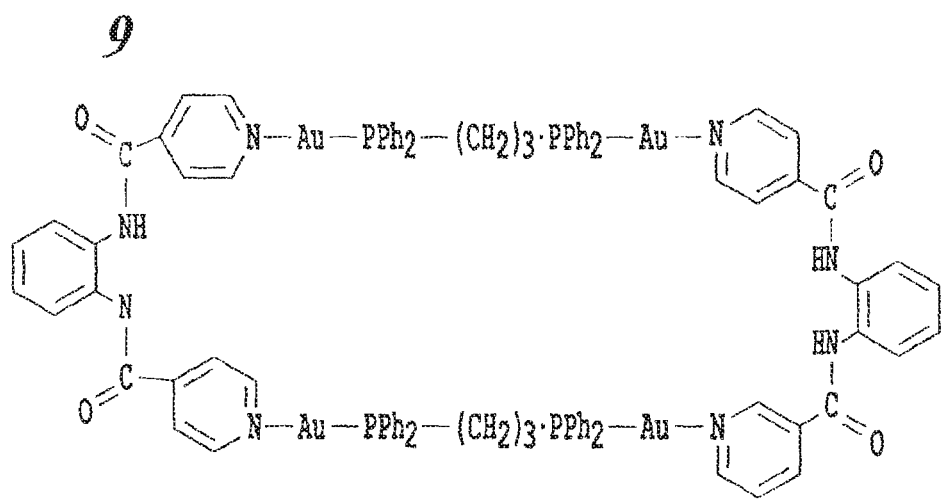
*Fig. 13B*

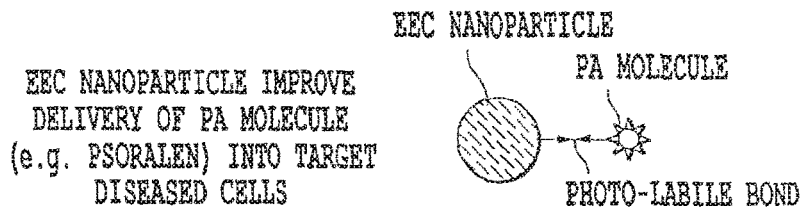
Fig. 16A
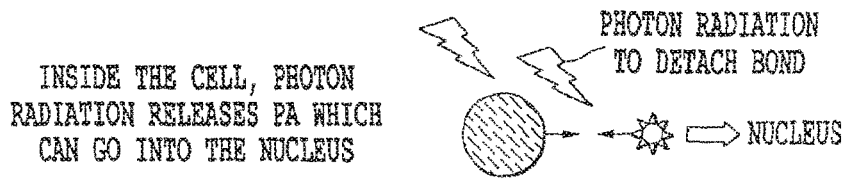
Fig. 16B
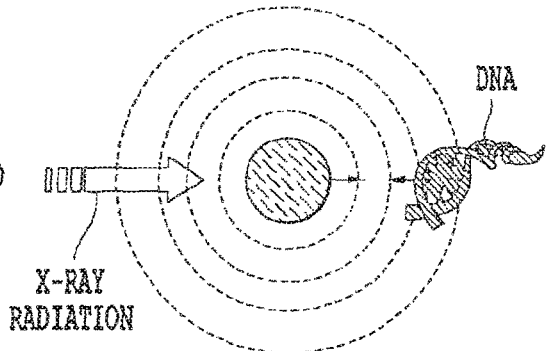
Fig. 16C
Fig. 17

ENCAPSULATED PHOTOACTIVE
DRUG MOLECULES

ENCAPSULATED PHOTOACTIVE
DRUG MOLECULES
WITH BIORECEPTOR

RELEASE OF
PHOTOACTIVE DRUG
MOLECULES

PHOTONIC ACTIVATION
OF PHOTOACTIVE DRUG
MOLECULES

STERILIZATION SYSTEM 1

STERILIZATION SYSTEM 2
WITH PLASMONICS

STERILIZATION SYSTEM 3

STERILIZATION SYSTEM 4
WITH PLASMONICS

STERILIZATION SYSTEM 5
WITH PLASMONICS

STERILIZATION SYSTEM 6
WITH PLASMONICS

STERILIZATION SYSTEM 7
WITH PLASMONICS

STERILIZATION SYSTEM 8
WITH PLASMONICS

STERILIZATION SYSTEM 9
WITH CHEMICAL RECEPTORS OR BIORECEPTORS

STERILIZATION SYSTEM 10
WITH PLASMONICS AND CHEMICAL
RECEPTORS OR BIORECEPTORS

STERILIZATION SYSTEM 11
WITH CHEMICAL RECEPTORS OR BIORECEPTORS

STERILIZATION SYSTEM 12
WITH PLASMONICS WITH CHEMICAL
RECEPTORS OR BIORECEPTORS

STERILIZATION PROBE SYSTEM 13
WITH CHEMICAL RECEPTORS OR BIORECEPTORS

STERILIZATION PROBE SYSTEM 14
WITH PLASMONICS

STERILIZATION PROBE SYSTEM 15
WITH CHEMICAL RECEPTORS OR BIORECEPTORS

STERILIZATION PROBE SYSTEM 16 WITH PLASMONICS
AND CHEMICAL RECEPTORS OR BIORECEPTORS

STERILIZATION SYSTEM 17 USING NANOPARTICLES

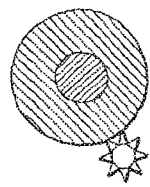

PA MOLECULES BOUND TO
METAL NANOPARTICLE

*Fig. 44A*

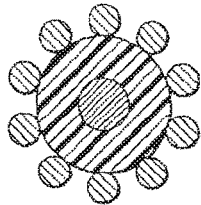

X-RAY CONVERTER NANO-
PARTICLE COVERED WITH
DIELECTRIC LAYER AND
METAL NANOPARTICLES

*Fig. 44B*

▨ MAGNETIC MATERIAL

▨ METAL (e.g., Au, Ag)

▨ MATERIAL CONTAINING X-RAY CONVERTER

▨ DIELECTRIC LAYER (e.g., SILICA)

▨ CHEMICAL RECEPTORS AND BIORECEPTORS

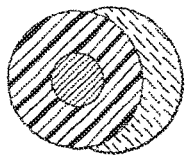

METAL NANOPARTICLE
COVERED WITH
DIELECTRIC LAYER AND
X-RAY CONVERTER NANOCAP

*Fig. 44C*

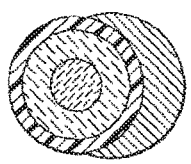

X-RAY CONVERTER NANO-
PARTICLE COVERED WITH
DIELECTRIC LAYER AND
METAL NANOCAP

*Fig. 44D*

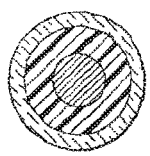

METAL NANOPARTICLE
COVERED WITH
DIELECTRIC LAYER
AND X-RAY CONVERTER
NANOSHELL

*Fig. 44E*

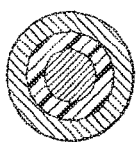

X-RAY CONVERTER
NANOPARTICLE
COVERED WITH
DIELECTRIC LAYER
AND METAL NANOSHELL

*Fig. 44F*

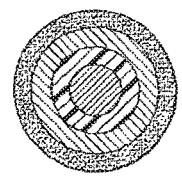

X-RAY CONVERTER
NANOPARTICLE
COVERED WITH
DIELECTRIC LAYER
AND METAL NANOSHELL
WITH PROTECTIVE
COATING LAYER

*Fig. 44G*

PLASMONIC ASSISTED SYSTEMS AND METHODS FOR INTERIOR ENERGY-ACTIVATION FROM AN EXTERIOR SOURCE

CROSS REFERENCE TO RELATED APPLICATIONS

This application is a continuation of U.S. Ser. No. 14/165,026 filed Jan. 27, 2014, the entire contents of which is incorporated herein by reference. U.S. Ser. No. 14/165,026 is a continuation of U.S. Ser. No. 13/713,931 filed Dec. 13, 2012 which is a continuation of U.S. Ser. No. 12/401,478 filed Mar. 10, 2009, the entire contents of each is incorporated herein by reference. This application is related to provisional Ser. No. 60/910,663, filed Apr. 8, 2007, entitled "METHOD OF TREATING CELL PROLIFERATION DISORDERS," and non-provisional Ser. No. 11/935,655, filed Nov. 6, 2007, entitled "METHOD OF TREATING CELL PROLIFERATION DISORDERS." the contents of each of which are hereby incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 12/389,946, filed Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to and claims priority under 35 U.S.C. 119(e) to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to and claims priority under 35 U.S.C. 119(e) to provisional Ser. No. 61/080,140, filed Jul. 11, 2008, entitled "PLASMONIC ASSISTED SYSTEMS AND METHODS FOR INTERIOR ENERGY-ACTIVATION FROM AN EXTERIOR SOURCE," the entire contents of which are hereby incorporated herein by reference.

BACKGROUND OF THE INVENTION

Field of Invention

The invention relates to methods and systems for generating in the interior of a medium or body radiant energy for producing a change in the properties of a medium or body by exposure to the radiation.

Discussion of the Background

Presently, light (i.e., electromagnetic radiation from the radio frequency through the visible to the x-ray and gamma ray wavelength range) activated processing is used in a number of industrial processes ranging from photoresist curing, to on-demand ozone production, to sterilization, to the promotion of polymer cross-linking activation (e.g. in adhesive and surface coatings) and others. Today, light activated processing is seen in these areas to have distinct advantages over more conventional approaches. For example, conventional sterilization by steam autoclaving or in food processing by pasteurization may unsuitably overheat the medium to be sterilized. As such, light activated curable coatings are one of the fastest growing sectors in the coatings industry. In recent years, this technology has made inroads into a number of market segments like fiber optics, optical and pressure-sensitive adhesives, and automotive applications like cured topcoats, and curable powder coatings. The driving force of this development is mostly the quest for an increase in productivity of the coating and curing process, as conventional non light activated adhesive and surface coatings typically require 1) the elimination of solvents from the adhesive and surface coatings to produce a cure and 2) a time/temperature cure which adds delay and costs to the manufacturing process.

Moreover, the use of solvent based products in adhesive and surface coatings applications is becoming increasingly unattractive because of rising energy costs and stringent regulation of solvent emissions into the atmosphere. Optimum energy savings as well as beneficial ecological considerations are both served by radiation curable adhesive and surface coating compositions. Radiation curable polymer cross-linking systems have been developed to eliminate the need for high oven temperatures and to eliminate the need for expensive solvent recovery systems. In those systems, light irradiation initiates free-radical cross-linking in the presence of common photosensitizers.

However, in the adhesive and surface coating applications and in many of the other applications listed above, the light-activated processing is limited due to the penetration depth of light into the processed medium. For example, in water sterilization, ultraviolet light sources are coupled with agitation and stirring mechanisms in order to ensure that any bacteria in the water medium will be exposed to the UV light. In light-activated adhesive and surface coating processing, the primary limitation is that the material to be cured must be directly exposed to the light, both in type (wavelength or spectral distribution) and intensity. In adhesive and surface coating applications, any "shaded" area will require a secondary cure mechanism, increasing cure time over the non-shaded areas and further delaying cure time due to the existent of a sealed skin through which subsequent curing must proceed (i.e., referred to as a cocoon effect).

SUMMARY OF THE INVENTION

The invention overcomes the problems and disadvantages of the prior art as described in the various embodiments below.

In one embodiment, there is provided a method and system for producing a change in a medium disposed in an artificial container. The method (1) places in a vicinity of the medium at least one of a plasmonics agent and an energy modulation agent, and (2) applies an initiation energy from an applied initiation energy source through the artificial container to the medium. The applied initiation energy interacts with the plasmonics agent or the energy modulation agent to directly or indirectly produce the change in the medium. The system includes the artificial container configured to contain the medium including the energy modulation agent or the plasmonics agent. The system further includes an applied initiation energy source configured to apply the initiation energy through the artificial container to the medium to activate at least one of the plasmonics agent and the energy modulation agent.

In another embodiment, there is provided a method and system for curing a radiation-curable medium. The method applies an applied energy throughout a composition including an uncured radiation-curable medium and at least one of a plasmonics agent and an energy modulation agent. The applied initiation energy interacts with the plasmonics agent or the energy modulation agent to directly or indirectly cure the medium by polymerization of polymers in the medium. The system includes an initiation energy source configured to apply initiation energy to the composition.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 provides an exemplary electromagnetic spectrum in meters (1 nm equals $10^{-9}$ meters);

FIG. 2 is a table providing a list of photoactivatable agents;

FIGS. 6A-6G provide representative embodiments of plasmonics photo-active probes useful in the invention;

FIGS. 7A and 7B are graphical explanations of the plasmonics-enhanced effect of the invention;

FIGS. 8A-8J show representative embodiments of plasmonics-active nanostructures;

FIG. 11 is a representation of an embodiment of the energy modulation agent (or excitation energy converter/ EEC)-photo activator (PA) system of the invention;

FIGS. 12A-12F are representations of several embodiments of plasmonics photo-active energy modulation agent-PA probes;

FIGS. 13A-13B show structures of various preferred embodiments of gold complexes exhibiting XEOL;

FIGS. 16A-16C are representations of embodiments of a PEPST energy modulation agent-PA system with detachable bond;

FIG. 17 is a representation of an embodiment of PEPST probes for dual plasmonic excitation;

FIG. 44A-44G are representations of different plasmonics probes of the invention.

DETAILED DESCRIPTION OF THE INVENTION

Figure 3A:
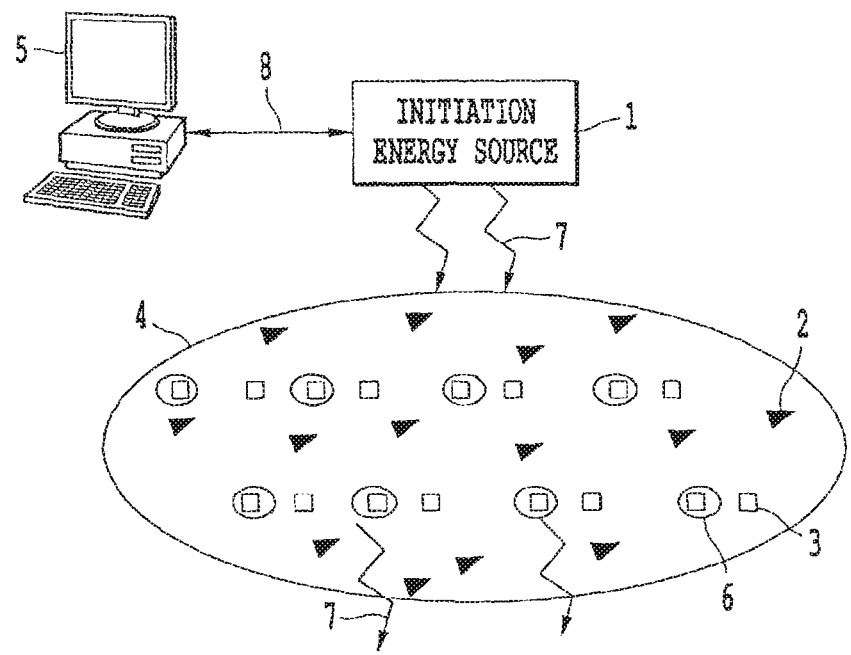
FIG. 3A is a schematic depicting a system according to one embodiment of the invention in which an initiation energy source is directed to a self-contained medium for producing changes in the medium.

The invention sets forth a novel method for causing a change in activity of an in a medium that is effective, specific, and able to produce a change to the medium.

Generally, the invention provides methods for producing a change in a medium after generation of radiant light inside the medium. In this method, an initiation energy source provides an initiation energy that penetrates the medium and induces internal radiation to produce a desired effect in the medium.

In one embodiment, the initiation energy source is applied directly or indirectly to the medium. Within the context of the invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the medium beneath the surface of the medium and to the activatable agents or energy modulation agents within a medium. In one embodiment, the initiation energy interacts with a previously supplied energy modulation agent which then activates the activatable agent.

Although not intending to be bound by any particular theory or be otherwise limited in any way, the following theoretical discussion of scientific principles and definitions are provided to help the reader gain an understanding and appreciation of the invention.

As used herein, an "activatable agent" is an agent that normally exists in an inactive state in the absence of an activation signal. When the agent is activated by an activation signal under activating conditions, the agent is capable of producing a desired pharmacological, cellular, chemical, electrical, or mechanical effect in a medium (i.e. a predetermined change). For example, when photocatalytic agents are irradiated with visible or UV light, these agents induce polymerization and "curing" of light sensitive adhesives.

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof. Activation of the agent may be as simple as delivering the signal to the agent or may further require a set of activation conditions. For example, an activatable agent, such as a photosensitizer, may be activated by UV-A radiation (e.g., by UV-A radiation generated internally in the medium). Once activated, the agent in its active-state may then directly proceed to produce a predetermined change.

Where activation may further require other conditions, mere delivery of the activation signal may not be sufficient to bring about the predetermined change. For example, a photoactive compound that achieves its effect by binding to certain structure in its active state may require physical proximity to the target structure when the activation signal is delivered. For such activatable agents, delivery of the activation signal under non-activating conditions will not result in the desired effect. Some examples of activating conditions may include, but are not limited to, temperature, pH, location, state of the medium, and the presence or absence of co-factors.

Selection of an activatable agent greatly depends on a number of factors such as the desired change, the desired form of activation, as well as the physical and biochemical constraints that may apply. Exemplary activatable agents may include, but are not limited to agents that may be activated by photonic energy, electromagnetic energy, acoustic energy, chemical or enzymatic reactions, thermal energy, microwave energy, or any other suitable activation mechanisms.

When activated, the activatable agent may effect changes that include, but are not limited to an increase in organism activity, a fermentation, a decrease in organism activity, apoptosis, redirection of metabolic pathways, a sterilization of a medium, a cross polymerization and curing of a medium, or a cold pasteurization of a medium.

The mechanisms by which an activatable agent may achieve its desired effect are not particularly limited. Such mechanisms may include direct action on a predetermined target as well as indirect actions via alterations to the biochemical pathways. In one embodiment, the activatable agent is capable of chemically binding to the organism in a medium. In this embodiment, the activatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity capable of producing a predetermined activity once activated.

The activatable agent may be derived from a natural or synthetic origin. Any such molecular entity that may be activated by a suitable activation signal source to effect a predetermined cellular change may be advantageously employed in the invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substitutes of the photosensitizers from which they are derived, and which preserve the function and substantial non-toxicity. Endogenous molecules are inherently non-toxic and may not yield toxic photoproducts after photoradiation.

FIG. 1 provides an exemplary electromagnetic spectrum in meters (1 nm equals 1 nanometer). As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy.

Table 1 in FIG. 2 provides a list of photoactivatable agents that may be used as primary or secondary internal light sources. For example, the photoactivatable agents could be receptors of X-ray induced emissions from nanoparticles (to be discussed later) and which in turn emit a secondary light. In some mediums, it may be that the excitation wavelengths in Table 1 are transparent to the particular medium and the emission wavelengths are highly absorbent (due to, for example, molecular or solid state band gap transitions). In those cases, the photoreactive agents in Table 1 would be the primary sources for internal light generation.

In various embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Typically, the energy modulation agents induce photoreactive changes in the medium and are not used for the purpose of exclusively heating the medium.

Various exemplary uses are described in the embodiments below.

The modulation agents may further be coupled to a carrier for targeting purposes. For example, a biocompatible molecule, such as a fluorescing metal nanoparticle or fluorescing dye molecule that emits in the UV-A band, may be selected as the energy modulation agent. The energy modulation agent may be preferably directed to the desired site by systemic administration into a medium. For example, a UV-A emitting energy modulation agent may be distributed in the medium by physical insertion and or mixing, or by conjugating the UV-A emitting energy modulation agent with a specific carrier, such as a lipid, chitin or chitin-derivative, a chelate or other functionalized carrier that is capable of concentrating the UV-A emitting source in a specific target region of the medium.

Additionally, the energy modulation agent can be used alone or as a series of two or more energy modulation agents such that the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable agent. Alternatively, one or more energy modulation agents in the cascade may also activate additional activatable agents.

Although the activatable agent and the energy modulation agent can be distinct and separate, it will be understood that the two agents need not be independent and separate entities. In fact, the two agents may be associated with each other via a number of different configurations. Where the two agents are independent and separately movable from each other, they can generally interact with each other via diffusion and chance encounters within a common surrounding medium. Where the activatable agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, ultraviolet lamps such as UV-A and UV-B lamps, halogen lamps, fiber optic lines, a light needle, an endoscope, self-ballasted mercury vapor lamps, ballasted HID lamps, and any device capable of generating x-ray, y-ray, gamma-ray, or electron beams.

In one embodiment, the initiation energy is capable of penetrating completely through the medium. Within the context of the invention, the phrase "capable of penetrating completely through the medium" is used to refer to energy capable of penetrating a container to any distance necessary to activate the activatable agent within the medium. It is not required that the energy applied actually pass completely through the medium, merely that it be capable of doing so in order to permit penetration to any desired distance to activate the activatable agent. The type of energy source chosen will depend on the medium itself. Exemplary initiation energy sources that are capable of penetrating completely through the medium include, but are not limited to, x-rays, gamma rays, electron beams, microwaves and radio waves.

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edt/~argon/nanoradio/radio.html, the entire contents of which are hereby incorporated by reference). These nanotubes can be introduced to the medium, and preferably would be coupled to the activatable agent or the energy modulation agent, or both, such that upon application of the initiation energy, the nanotubes would accept the initiation energy (preferably radiowaves), then emit radiowaves in close proximity to the activatable agent, or in close proximity to the energy modulation agent, to then cause activation of the activatable agent. In such an embodiment, the nanotubes would act essentially as a radiowave focusing or amplification device in close proximity to the activatable agent or energy modulation agent.

Alternatively, the energy emitting source may be an energy modulation agent that emits energy in a form suitable for absorption by a transfer agent or for direct interaction with components of the medium. For example, the initiation energy source may be acoustic energy, and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent.

Photoactivatable agents may be stimulated by an energy source through mechanisms such as irradiation, resonance energy transfer, exciton migration, electron injection, or chemical reaction, to an activated energy state that is capable of producing the predetermined change desired. One advantage is that wavelengths of emitted radiation may be used to selectively stimulate one or more photoactivatable agents or energy modulation agents capable of stimulating the one or more photoactivatable agents. The energy modulation agent is suitably stimulated at a wavelength and energy that causes little or no change to the medium.

In another embodiment, the photoactivatable agent is stimulated via a resonance energy transfer. Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. One advantage is that multiple wavelengths of emitted radiation may be used to selectively stimulate one or more photoactivatable agents or energy modulation agents capable of stimulating the one or more photoactivatable agents. With RET, the energy modulation agent is preferably stimulated at a wavelength and energy that causes little or no effect to the surrounding medium with the energy from one or more energy modulation agents being transferred, such as by Foerster Resonance Energy Transfer, to the photoactivatable agents.

Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can apply the initiation energy source to the medium. Within the context of the invention, the applying of the initiation energy source means the application of an agent, that itself produces the initiation energy, in a manner that permits the agent to arrive at the target structure within the medium. The application can take any form. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, nanoemitters, nanochips, and other nanomachines that produce and emit energy of a desired frequency.

Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the invention to provide targeting of the target cell, to deliver the initiation energy source directly at the desired site.

In another embodiment, the invention includes the application of the activatable agent, along with a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the medium or inside the medium, with the chemiluminescence, phosphorescence or bioluminescence being allowed to activate the activatable agent in the medium. The administration of the activatable agent and the source of chemical energy can be performed sequentially in any order or can be performed simultaneously.

In the case of certain sources of such chemical energy, the application of the chemical energy source can be performed after activation outside the medium, with the lifetime of the emission of the energy being up to several hours for certain types of phosphorescent materials for example.

When molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ via an internal conversion (IC) process. IC processes are transitions between states of the same multiplicity.

The molecule subsequently deactivates to the lowest vibronic levels of $S_{n-1}$ via a VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local changes in the medium.

Light absorbing species in various embodiments can include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of laser energy needed to induce a local change in the medium.

One problem associated with the use of dye molecules is their photobleaching under laser irradiation. Therefore, nanoparticles such as gold nanoparticles and nanoshells have recently been used. The promising role of nanoshells in medical applications has been demonstrated [Hirsch, L. R., Stafford, R. J., Bankson, J. A., Sershen, S. R., Rivera. B., Price, R. E., Hazle, J. D., Halas, N. J., and West, J. L., *Nanoshell-mediated near-infrared thermal therapy of tumors under magnetic resonance guidance*. PNAS, 2003. 100(23): p. 13549-13554], the entire contents of which are incorporated herein by reference. The use of plasmonics-enhanced photothermal properties of metal nanoparticles for photothermal therapy has also been reviewed (Xiaohua Huang & Prashant K. Jain & Ivan H. El-Sayed & Mostafa A. El-Saved. "*Plasmonic photothermal therapy (PPTT) using gold nanoparticles*". Lasers in Medical Science. August 2007), the entire contents of which are incorporated herein by reference.

Yet another example is that nanoparticles or nanoclusters of certain atoms may be introduced such that they are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a medium are capable of stimulating activation of photoactivatable agents disposed in a distant portion of the medium, so long as the distance does not greatly exceed $R_0$. For example, gold nanospheres having a size of 5 atoms of gold have been shown to have an emission band in the ultraviolet range, recently.

Any of the photoactivatable agents may be exposed to an excitation energy source provided in the medium. The photoactive agent may be directed to a receptor site by a carrier having a strong affinity for the receptor site. Within the context of the invention, a "strong affinity" is preferably an affinity having an equilibrium dissociation constant, $K_t$, at least in the nanomolar, nM, range or higher. The carrier may be a polypeptide and may form a covalent bond with a photoactive agent, for example. Alternatively, a photoactive agent may have a strong affinity for the target molecule in the medium without binding to a carrier.

In one embodiment, a plurality of sources for supplying electromagnetic radiation energy or energy transfer is provided by one or more molecules provided to the medium. The molecules may emit stimulating radiation in the correct band of wavelength to stimulate the photoactivatable agents, or the molecules may transfer energy by a resonance energy transfer or other mechanism directly to the photoactivatable agent or indirectly by a cascade effect via other molecular interactions.

In a further embodiment, a biocompatible emitting source, such as a fluorescing metal nanoparticle or fluorescing dye molecule, is selected that emits in the UV-A band. UV-A and the other UV bands are known to be effective as germicides.

In one embodiment, the UV-A emitting source is a gold nanoparticle comprising a cluster of 5 gold atoms, such as a water soluble quantum dot encapsulated by polyamidoamine dendrimers. The gold atom clusters may be produced through a slow reduction of gold salts (e.g. $HAuCl_4$ or $AuBr_3$) or other encapsulating amines, for example. One advantage of such a gold nanoparticle is the increased Foerster distance (i.e. $R_0$), which may be greater than 100 angstroms. The equation for determining the Foerster distance is substantially different from that for molecular fluorescence, which is limited to use at distances less than 100 angstroms. It is believed that the gold nanoparticles are governed by nanoparticle surface to dipole equations with a $1/R^4$ distance dependence rather than a $1/R^6$ distance dependence. For example, this permits cytoplasmic to nuclear energy transfer between metal nanoparticles and a photoactivatable molecule.

In another embodiment, a UV or light-emitting luciferase is selected as the emitting source for exciting a photoactivatable agent. A luciferase may be combined with molecules, which may then be oxygenated with additional molecules to stimulate light emission at a desired wavelength. Alternatively, a phosphorescent emitting source may be used. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. By pairing a combined energy harvester with a photoactivatable molecule, a further energy resonance transfer excites the photoactivatable molecule, when the photoactivatable molecule is nearby stimulated combined energy harvester molecules. Another example of a harvester molecule is disclosed in FIG. 4 of "Singlet-Singlet and Triplet-Triplet Energy Transfer in Bichromophoric Cyclic Peptides," M. S. Thesis by M. O. Guler, Worcester Polytechnic Institute, May 18, 2002, which is incorporated herein by reference.

In another embodiment, a Stokes shift of an emitting source or a series of emitting sources arranged in a cascade is selected to convert a shorter wavelength energy, such as X-rays, to a longer wavelength fluorescence emission such a optical or UV-A, which is used to stimulate a photoactivatable molecule in the medium.

In an additional embodiment, the photoactivatable agent can be a photocaged complex having an active agent (which can be a cytotoxic agent if cytotoxicity is needed, or can be an activatable agent) contained within a photocage. In various embodiments, where the active agent is a cyotoxic agent, the photocage molecule releases the cytotoxic agent into the medium where it can attack non-beneficial "target" species in the medium. The active agent can be bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters.* 16(10). pp. 2658-2661 (2006), the contents of which are hereby incorporated by reference.

Work has shown that the amount of singlet oxygen necessary to cause cell lysis, and thus cell death, is 0.32 H $10^{-3}$ mol/liter or more, or $10^9$ singlet oxygen molecules/cell or more. In one embodiment of the invention, the level of singlet oxygen production caused by the initiation energy or the activatable agent upon activation is sufficient to cause a change in a medium, wherein the medium becomes free from any microorganisms. Microorganisms include but are not limited to bacteria, viruses, yeasts or fungi. To this end, singlet oxygen in sufficient amounts as described above can be used to sterilize the medium.

For example, medical bottle caps need to be sterilized between the base cap material and the glued seal material which contacts the base of the medical bottle. Because steam autoclaves are insufficient for this purpose, one embodiment of the invention uses UV luminescing particles included in the adhesive layer when the seal material is applied to the bottle cap. Then. X-ray irradiation becomes capable of curing the adhesive and producing within the adhesive medium UV radiation for direct sterilization or the production of singlet oxygen or ozone for biological germicide.

The activatable agent and derivatives thereof as well as the energy modulation agent, can be incorporated into compositions suitable for delivery to particular mediums. The composition can also include at least one additive having a complementary effect upon the medium, such as a lubricant or a sealant.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Referring to FIG. 3A, an exemplary system according to one embodiment of the invention may have an initiation energy source 1 directed at medium 4. Activatable agents 2 and an energy modulation agents 3 are dispersed throughout the medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 3A as silica encased energy modulation agents. As shown in FIG. 3A, initiation energy 7 in the form of radiation from the initiation energy source 1 permeated throughout the medium 4. A more thorough discussion of the computer system 5 is provided below in reference to FIG. 4. As discussed below in more detail, the initiation energy source 1 can be an external energy source or an energy source located at least partially in the medium 4. As discussed below in more detail, activatable agents 2 and/or the energy modulation agents 3 can include plasmonics agents which enhance either the applied energy or the energy emitted from the energy modulation agents 3 so as to directly or indirectly produce a change in the medium.

In various embodiments, the initiation energy source 1 may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.). In other embodiments, the initiation energy source 1 may be commercially available components of X-ray machines or non-medical X-ray machines. X-ray machines that produce from 10 to 150 keV X-rays are readily available in the marketplace. For instance, the General Electric Definium series or the Siemens MULTIX series are but two examples of typical X-ray machines designed for the medical industry, while the Eagle Pack series from Smith Detection is an example of a non-medical X-ray machine. As such, the invention is capable of performing its desired function when used in conjunction with commercial X-ray equipment.

In other embodiments, the initiation energy source 1 can be a radio frequency or microwave source emitting radio waves at a frequency which permeates the medium and which triggers or produces secondary radiant energy emission within the medium by interaction with the energy modulation elements 6 therein. In other embodiments, the initiation energy source 1 can be an ultraviolet, visible, near infrared (NIR) or infrared (IR) emitter emitting at a frequency which permeates the medium 4 and which triggers or produces secondary radiant energy emission within medium 4 by interaction with the energy modulation elements 6 therein.

Figure 3B:
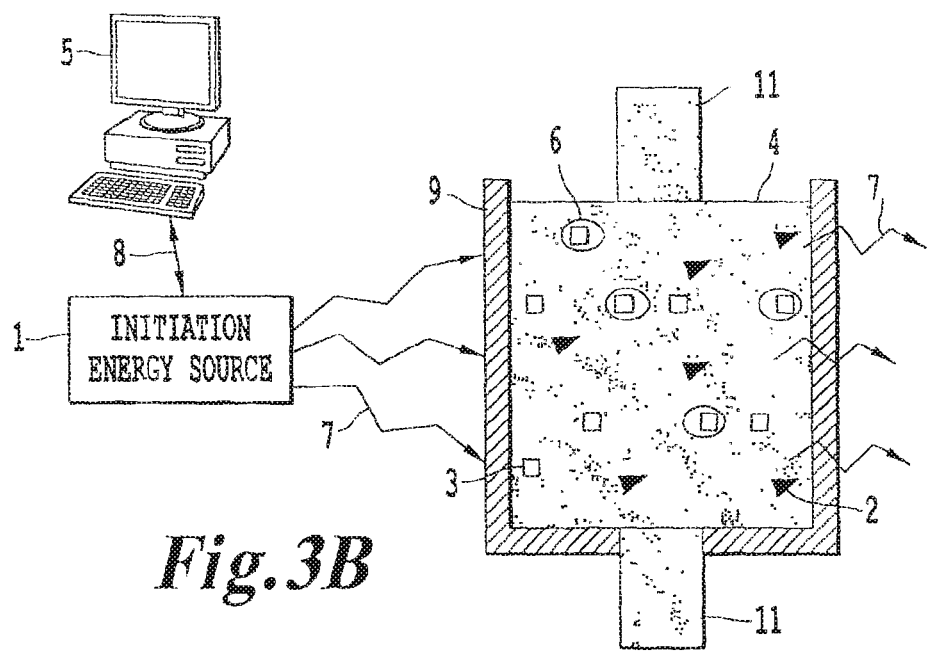
FIG. 3B is a schematic depicting a system according to another embodiment of the invention in which the initiation energy source is directed to a container enclosing a medium having energy modulation agents disbursed within the medium.

FIG. 3B is a schematic depicting another system according to another embodiment of the invention in which the initiation energy source 1 of FIG. 3A is directed to energy modulation elements 6 placed in the vicinity of a fluid medium 4 (e.g., a liquid or other fluid-like medium) and held inside a container 9. The container 9 is made of a material that is "transparent" to the radiation 7. For example, plastic, quartz, glass, or aluminum containers would be sufficiently transparent to X-rays, while plastic or quartz or glass containers would be transparent to microwave or radio frequency light. The energy modulation elements 6 can be dispersed uniformly throughout the medium or may be segregated in distinct parts of the medium or further separated physically from the medium by encapsulation structures 10. A supply 11 provides the medium 4 to the container 9.

Figure 3C:
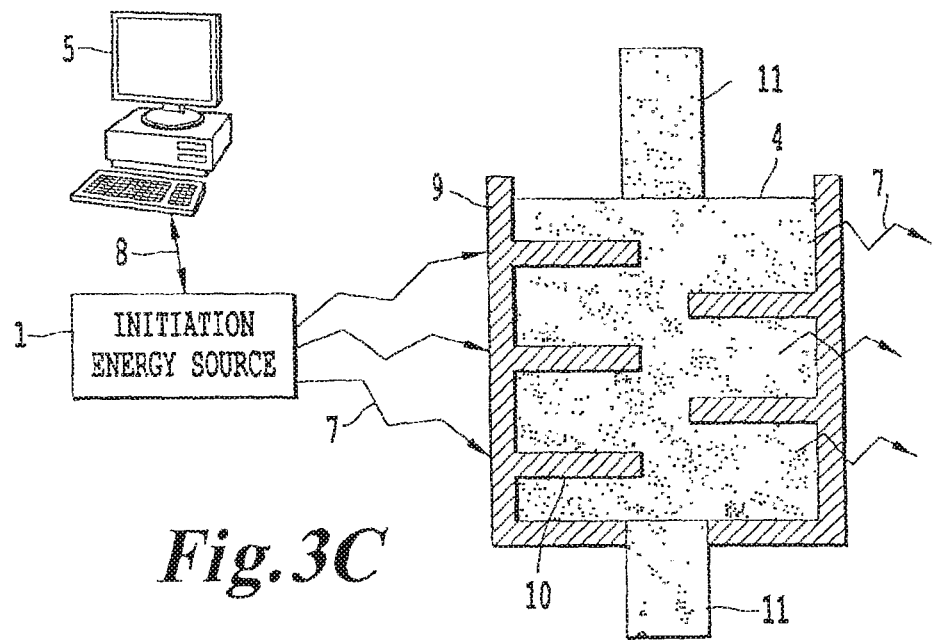
FIG. 3C is a schematic depicting a system according to another embodiment of the invention in which the initiation energy source is directed to a container enclosing a medium having energy modulation agents segregated within the medium.

Alternatively, as shown in FIG. 3C, the luminescing particles could be present in the medium in encapsulated structures 10. In one embodiment, the encapsulated structures 10 are aligned with an orientation in line with the external initiation energy source 1. In this configuration, each of the encapsulated structures 10 has itself a "line-of-sight" to the external initiation energy source 1 shown in FIG. 3C without being occluded by other of the encapsulated structures 10. In other embodiments, the encapsulated structures 10 are not so aligned in that direction, but could aligned perpendicular to the direction shown in FIG. 3C, or could be randomly placed. Indeed, supply of fluid medium 4 could itself be used to agitate the encapsulated structures 10 and mix the fluid medium 4 inside container 9.

The system of FIG. 3C may also be used without energy modulation agents. In this embodiment, the initiation energy source 1 can be for example at an energy suitable for driving physical, chemical, and/or biological processes in the fluid medium 4. The plasmonics agents included in the encapsulated structures 10 effectively amplify the light from the initiation energy source 1 as it interacts with the medium 4. In one aspect of the invention, the initiation energy source 1 can a UV light source as in many conventional UV sterilization systems and the encapsulated structures 10 of FIG. 3C are light rods conducting UV light from an exterior source to a region inside the medium 4. In one aspect of the invention, the initiation energy source 1 can be even disposed inside the medium and can be a UV light source as in many conventional UV sterilization systems.

Figure 3D:
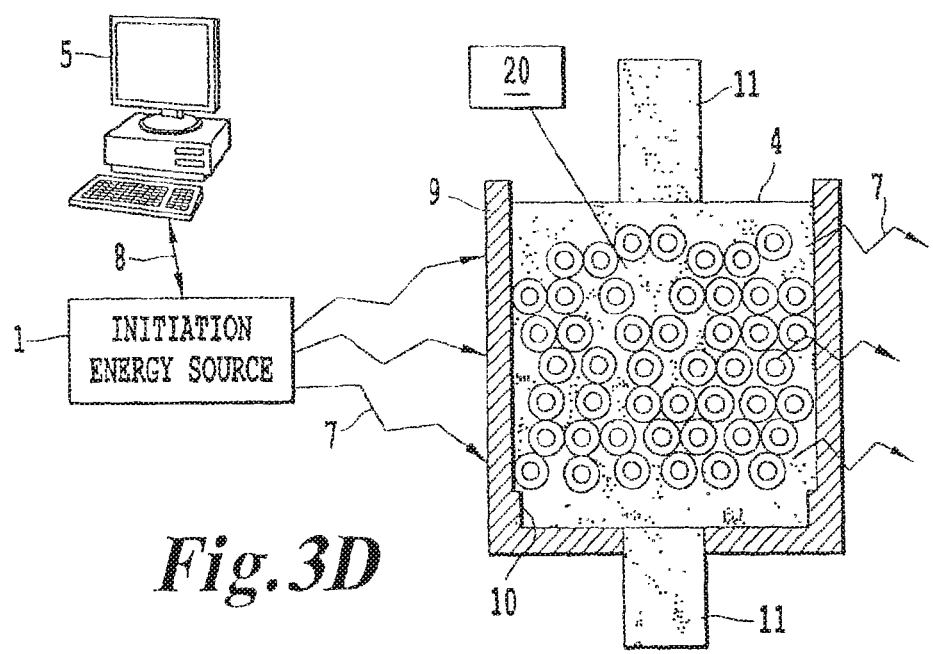
FIG. 3D is a schematic depicting a system according to another embodiment of the invention in which the initiation energy source is directed to a container enclosing a medium having energy modulation agents segregated within the medium in a fluidized bed configuration.

FIG. 3D is a schematic depicting a system according to another embodiment of the invention in which the initiation energy source is directed a container enclosing a medium having energy modulation agents segregated within the medium in a fluidized bed 20 configuration. The fluidized bed 20 includes the encapsulated structures 10 in a configuration where a fluid to be treated is passed between the encapsulated structures 10. The encapsulated structures 10 can include both energy modulation agents and plasmonics agents as described herein.

In further embodiments of the invention, robotic manipulation devices may also be included in the systems of FIGS. 3A, 3B, 3C, and 3D for the purpose of delivering and dispersing the energy modulation elements 6 in medium 4 or for the purpose of removing old product and introducing new product for treatment into the system.

In the invention, energy transfer among molecules may occur in a number of ways. The form of energy may be electronic, thermal, electromagnetic, kinetic, or chemical in nature. The energy can be modulated up to emit higher energy from the energy modulation agent compared to the input initiation energy, or can be modulated down to emit lower energy from the energy modulation agent compared to the input initiation energy. Energy may be transferred from one molecule to another (intermolecular transfer) or from one part of a molecule to another part of the same molecule (intramolecular transfer). For example, a modulation agent may receive electromagnetic energy and re-emit the energy in the form of a different energy. In various embodiments, the energy modulation agents receive higher energy (e.g. x-ray) and re-emits in lower energy (e.g. UV-A). In other embodiments, the energy modulation agent receive lower energy (e.g., infrared or near-infrared) and emits in a higher energy (e.g., visible or ultraviolet). Energy transfer processes are also referred to as molecular excitation. Some modulation agents may have a very short energy retention time (on the order of fs-ns, e.g. fluorescent molecules) whereas others may have a very long half-life (on the order of seconds to hours, e.g. luminescent inorganic molecules or phosphorescent molecules). Suitable energy modulation agents include, but are not limited to, a metal nanoparticle or a biocompatible metal nanoparticle, a metal coated or uncoated with a biocompatible outer layer, a chemiluminescent molecule whose rate of luminescence is increased by microwave activation, fluorescing dye molecule, gold nanoparticle, a water soluble quantum dot encapsulated by polyamidoamine dendrimers, a luciferase, a biocompatible phosphorescent molecule, a biocompatible fluorescent molecule, a biocompatible scattering molecule, a combined electromagnetic energy harvester molecule, and a lanthanide chelate capable of intense luminescence. Various exemplary uses of these are described.

The modulation agents may further be coupled to a carrier for targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. in close vicinity to a photoactive substance such as for example a photocatalyst or a photo initiator) by pre-distribution of the energy modulation agent into a medium to be exposed to the activation energy. For example, a UV-A emitting energy modulation agent may be concentrated in joints for adhesion of two parts together by physical insertion or by conjugating the UV-A emitting energy modulation agent with a photoactivatable resin.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary, to activate the photo-activatable agent in the medium.

Although the photo-activatable agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the photo-activatable agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. The energy used can be any type, including but not limited to, gamma ray, x-ray, UV, near-UV, visible, Near IR, IR microwave, radio wave, etc. In a preferred embodiment, the initiation energy capable of penetrating completely through the subject. Exemplary initiation energy sources that are capable of penetrating completely through the subject include, but are not limited to, x-rays, gamma rays, electron beams, microwaves and radio waves.

Basic Principle of Plasmonics and Enhanced Electromagnetic Fields

The plasmonics-enhanced principle is based in theory on enhancement mechanisms of the electromagnetic field effect. These theories are advanced here for the sake of illustrating the invention and are not necessarily intended to limit any of the embodiments to this particular theory. There are two main sources of electromagnetic enhancement: (1) first, the laser electromagnetic field is enhanced due to an addition of a field caused by a polarization of a metal particle; (2) an enhancement due to the molecule radiating an amplified emission (luminescence, Raman, etc.) field, which further polarizes the metal particle, thereby acting as an antenna to further amplify a Raman/Luminescence signal.

Electromagnetic enhancements are divided into two main classes: a) enhancements that occur only in the presence of a radiation field, and b) enhancements that occur even without a radiation field. The first class of enhancements is further divided into several processes. Plasma resonances on substrate surfaces, also called surface plasmons, provide a significant contribution to electromagnetic enhancement. One effective type of plasmonics-active substrate includes nanostructured metal particles, protrusions, or rough surfaces of metallic materials. Incident light irradiating these surfaces excites conduction electrons in the metal, and induces the excitation of surface plasmons leading to Raman/luminescence enhancement. At a plasmon frequency, metal nanoparticles (or other nanostructured roughened structures) become polarized, resulting in large field-induced polarizations and thus large local fields on the surface. These local fields increase the luminescence/Raman emission intensity, which is proportional to the square of the applied field at the molecule.

As a result, the effective electromagnetic field experienced by an analyte molecule on these surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence).

Accordingly, plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents thus provides a selective and efficient strategy for the efficient use of internally generated light.

Accordingly, the invention utilizes several important mechanisms:
(A) Increased absorption of the excitation light by the plasmonic metal nanoparticles, resulting in enhanced photoactivation of photoinitiators or photocatalysts;
(B) Increased absorption of the excitation light by the plasmonic metal nanoparticles that serve as more efficient energy modulation agent systems, yielding more light for increased excitation of the photoinitiators or photocatalysts;
(C) Increased absorption of the excitation light by the medium material on or near the plasmonic metal nanoparticles;
(D) Increased light absorption of the energy modulation agent molecules adsorbed on or near the metal nanoparticles;
(E) Amplified light emission from the energy modulation agent molecules adsorbed on or near the metal nanoparticles; and
(F) Increased absorption of emission light emitted from the energy modulation agent by the photoinitiators or photocatalysts.

Figure 5A:
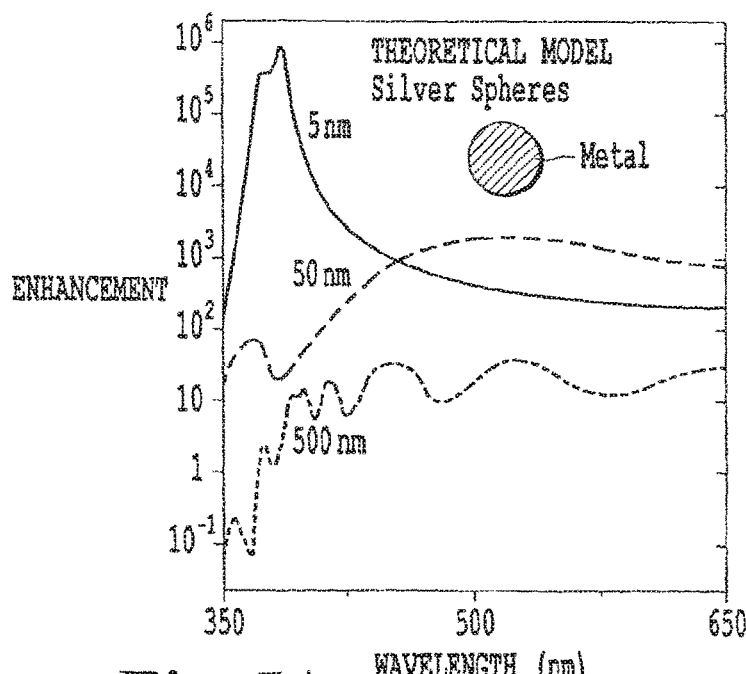
FIGS. 5A and 5B are representations of plasmonic nanostructures and their theoretical electromagnetic enhancement at different excitation wavelength.
Figure 5B:
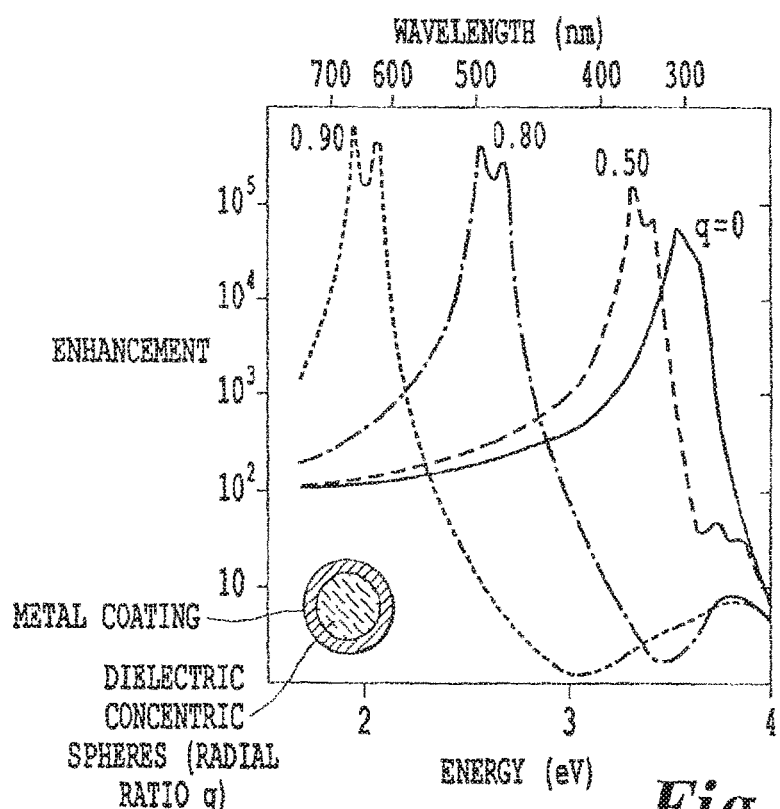

As discussed above, one of several phenomena that can enhance the efficiency of light emitted (Raman or luminescence) from molecules adsorbed or near a metal nanostructures Raman scatter is the surface-enhanced Raman scattering (SERS) effect. In 1984, the general applicability of SERS as an analytical technique was first reported by one of the present inventors, and the possibility of SERS measurement for a variety of chemicals including several homocyclic and heterocyclic polyaromatic compounds [T. Vo-Dinh. M. Y. K. Hiromoto, G. M. Begun and R. L. Moody. "Surface-enhanced Raman spectroscopy for trace organic analysis." Anal. Chem., vol. 56, 1667, 1984], the entire contents of which are incorporated herein by reference. Extensive research has been devoted to understanding and modeling the Raman enhancement in SERS since the mid 1980's. FIG. 5, for example, shows the early work by Kerker modeling electromagnetic field enhancements for spherical silver nanoparticles and metallic nanoshells around dielectric cores as far back as 1984 [M. M. Kerker, Acc. Chem. Res., 17, 370 (1984)], the entire contents of which are incorporated herein by reference. This figure shows the result of theoretical calculations of electromagnetic enhancements for isolated spherical nanospheres and nanoshells at different excitation wavelengths. The intensity of the normally weak Raman scattering process is increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

Theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons." and b) an effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons." produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

Design, Fabrication and Operation of Plasmonics-Enhanced Structures

FIGS. 6A-6G shows a number of the various embodiments of plasmonics-enhanced probe structures (PEPST) that can be designed:
- (A) Photo-activatable (PA) molecules bound to a metal (e.g., gold) nanoparticle;
- (B) Photo-activatable (PA) molecule covered with metal nanoparticles;
- (C) Metal nanoparticle covered with PA nanocap;
- (D) PA-containing nanoparticle covered with metal nanocap;
- (E) Metal nanoparticle covered with PA nanoshell;
- (F) PA-containing nanoparticle covered with metal nanoshell; and
- (G) PA-containing nanoparticle covered with metal nanoshell with protective coating layer.

A basic embodiment of the PEPST is shown in FIG. 6A. This PEPST includes PA molecules bound to a metal (e.g., gold) nanoparticle. FIG. 7 illustrates the plasmonics-enhancement effect as it would be used in this invention to enhance the interaction of the primary excitation light source with energy modulation agents or to enhance the interaction of the secondarily produced light with the medium in effecting a change to the medium. Radiation of suitable energy is used to excite the PEPST structures which in turn activates for example nearby photoinitiators.

For example, light of a HeNe laser (632.8-nm excitation) can be used for excitation. In this case the metal nanoparticles are designed to exhibit strong plasmon resonance band around 632.8 nm. The surface plasmon resonance effect amplifies the excitation light at the nanoparticles, resulting in an increased photoactivation of a photo-initiator or a photo-catalyst and improved reaction kinetic. Further, for sterilization applications, the effect increases the likelihood for a germicide event in the medium in vicinity of the nanoparticles. While light such as the HeNe laser light might be scattered and absorbed in the medium, the presence of the PEPST structures enhances the interaction of the penetrating light beyond that which would normally be considered useful. The plasmonics-enhanced mechanism can also be used with the other PEPST probes in FIGS. 6B, 6C. 6D, 6E, 6F and 6G.

Structures of Plasmonics-Active Metal Nanostructures

Plasmon resonances arise within a metallic nanoparticle from the collective oscillation of free electrons driven by an incident optical field. The plasmonic response of nanoparticles have played a role in a growing number of applications, including surface-enhanced Raman scattering (SERS), chemical sensing, drug delivery, photothermal cancer therapy, and new photonic devices. The investigation and application of plasmonics nanosubstrates for SERS detection has been used by one of the present inventors for over two decades [T. Vo-Dinh, "Surface-Enhanced Raman Spectroscopy Using Metallic Nanostructures," *Trends in Anal. Chem.*, 17.557 (1998)], the entire contents of which are incorporated herein by reference. The first report by one of the present inventors on the practical analytical use of the SERS techniques for trace analysis of a variety of chemicals including several homocyclic and heterocyclic polyaromatic compounds was in 1984 [T. Vo-Dinh, M. Y. K. Hiromoto, G. M. Begun and R. L. Moody, "*Surface-enhanced Raman spectroscopy for trace organic analysis.*" *Anal. Chem.*, vol. 56, 1667, 1984], the entire contents of which are incorporated herein by reference. Since then, the development of SERS technologies for applications in chemical sensing, biological analysis and medical diagnostics has been ongoing. The substrates involve nanoparticles and seminanoshells having a layer of nanoparticles coated by a metal (such as silver) on one side (nanocaps or half-shells). Several groups have shown that plasmon resonances of spherical shells can be tuned by controlling the shell thickness and aspect ratios of the nanoshell structures [M. M. Kerker, *Acc. Chem. Res.*, 17, 370 (1984); J. B. Jackson, S. L. Westcoit, L. R. Hirsch, J. L. West and N. H. Halas, "*Controlling the surface enhanced Raman effect via the nanoshell geometry.*" *Appl. Phys. Lett.*, vol. 82, 257-259, 2003, the entire contents of which are incorporated herein by reference; S J. Norton and T. Vo-Dinh. "*Plasmonic Resonances of nanoshells of Spheroidal Shape*", *IEEE Trans. Nanotechnology*, 6, 627-638 (2007), the entire contents of which are incorporated herein by reference]. These shells typically have a metallic layer over a dielectric core. In one embodiment of the invention, these shells include spheroidal shells, since the plasmon resonances (both longitudinal and transverse modes) are influenced by both shell thickness and aspect ratio. A number of researchers have examined the plasmonic response of the solid spheroidal particle in their analysis of surface-enhanced Raman scattering, although the spheroidal shell appears not to have been investigated. The invention also includes prolate and oblate spheroidal shells, which show some interesting qualitative features in their plasmon resonances. The spheroidal shell presents two degrees of freedom for tuning: the shell thickness and the shell aspect ratio [S. J. Norton and T. Vo-Dinh. "*Plasmonic Resonances of Nanoshells of Spheroidal Shape*", *IEEE Trans. Nanotechnology*, 6, 627-638 (2007)], the entire contents of which are incorporated herein by reference.

FIG. 7 shows some of the various embodiments of plasmonics-active nanostructures that can be designed, and are preferred embodiments of this invention:
- (A) Metal nanoparticle;
- (B) Dielectric nanoparticle core covered with metal nanocap;
- (C) Spherical metal nanoshell covering dielectric spheroid core;
- (D) Oblate metal nanoshell covering dielectric spheroid core;
- (E) Metal nanoparticle core covered with dielectric nanoshell;
- (F) Metal nanoshell with protective coating layer;
- (G) Multi layer metal nanoshells covering dielectric spheroid core;
- (H) Multi-nanoparticle structures;
- (I) Metal nanocube and nanotriangle/nanoprism; and
- (J) Metal cylinder.

PEPST Probes with Remotely-Activated Photoactivatable Molecules

In a further embodiment of the invention, the PA molecules can be incorporated into a material (e.g., biocompatible polymer) that can form a nanocap onto the metal (gold) nanoparticles. The material can be a gel or biocompatible polymer that can have long-term continuous release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ster) block copolymers, and ethylene vinyl acetate copolymers. The release mechanism can also be triggered by non-invasive techniques, such as RF, MW, ultrasound, photon (FIG. 8).

Figure 9A:
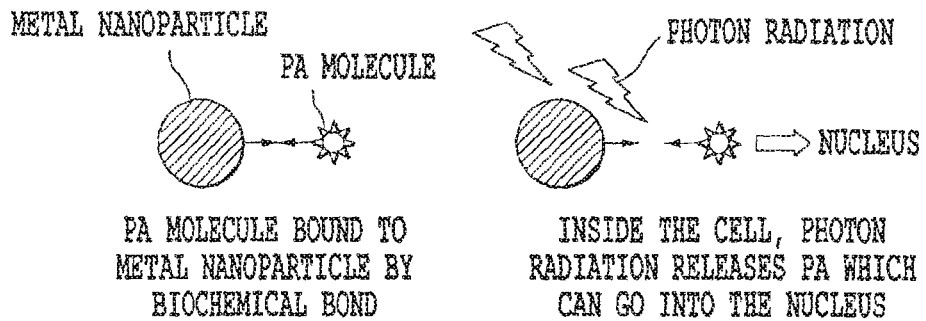
FIGS. 9A-9C are representations of several embodiments of PEPST probes with a linker that can be cut by a photon radiation.
Figure 9B:
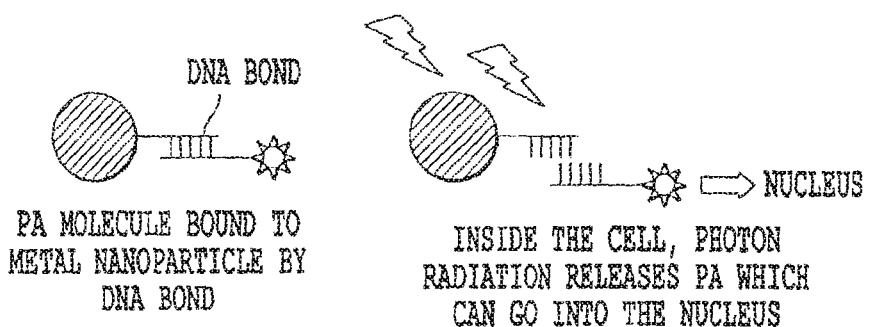
Figure 9C:
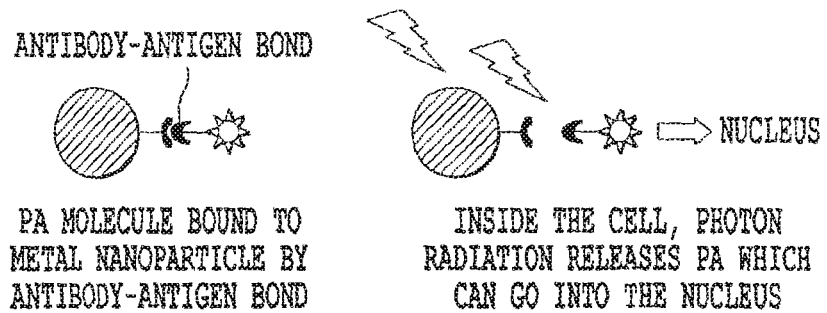

FIG. 9 shows other possible embodiments where the PA molecule is bound to the metal nanoparticles via a linker that can be cut by a photon radiation. Such a linker includes, but is not limited to, a biochemical bond (FIG. 9A), a DNA bond (FIG. 9B), or an antibody-antigen bond (FIG. 9C). In another embodiment, the linker is a chemically labile bond that will be broken by the chemical environment inside the cell. In various embodiments, it may be more difficult for metal nanoparticles to enter targeted cites in the medium than for smaller molecules. In these embodiments, it is desirable to have PEPST probes that have releasable PA molecules.

Aggregation of metal (such as silver or gold) nanoparticles (nanospheres, nanorods, etc) is often a problem, especially with citrate-capped gold nanospheres, cetyl trimethylammonium bromide (CTAB)-capped gold nanospheres and nanorods and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles).

Immobilization of Biomolecules and Metal Nanoparticles

The immobilization of biomolecules (PA molecules, drugs, proteins, enzymes, antibodies, DNA, etc.) to a support can use a wide variety of methods published in the literature. For example, the encapsulated structures 10 of FIGS. 3C and 3D can be modified in one embodiment of this invention such that the PEPST structures are immobilized on the outer exposed surfaces such that any light from the encapsulated structures would be enhanced in interaction with the medium. Furthermore, in one embodiment, the encapsulated structures 10 can not include an energy modulation agent. Rather, light from an external source such as a flash lamp or a LED array or laser or UV source could be transmitted through the empty encapsulated structures 10 and propagate into the medium. Binding can be performed through covalent bonds taking advantage of reactive groups such as amine (—NH$_2$) or sulfide (—SH) that naturally are present or can be incorporated into the biomolecule structure. Amines can react with carboxylic acid or ester moieties in high yield to form stable amide bonds. Thiols can participate in maleimide coupling, yielding stable dialkylsulfides.

One solid support of interest in this invention is the metal (preferably gold or silver) nanoparticles. The majority of immobilization schemes involving metal surfaces, such as gold or silver, utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface, with lengths of the alkyl group from 4 to 20 carbons being preferred.

There are many methods related to the preparation of stable oligonucleotide conjugates with gold particles by using thiol-functionalized biomolecules that had previously been shown to form strong gold-thiol bonds. Oligonucleotides with 5'-terminal alkanethiol functional groups as anchors can be bound to the surface of gold nanoparticles, and the resulting labels were robust and stable to both high and low temperature conditions [R. Elghanian, J. J. Storhoff, R. C. Mucic, R. L. Letsinger and C. A. Mirkin, *Selective colorimetric detection of polynucleotides based on the distance-dependent optical properties of gold nanoparticles. Science* 277 (1997), pp. 1078-1081], the entire contents of which are incorporated herein by reference. A cyclic dithiane-epiandrosterone disulfide linker has been developed for binding oligonucleotides to gold surfaces [R. Elghanian, J. J. Storhoff, R. C. Mucic, R. L. Letsinger and C. A. Mirkin, *Selective colorimetric detection of polynucleotides based on the distance-dependent optical properties of gold nanoparticles. Science* 277 (1997), pp. 1078-1081], the entire contents of which are incorporated herein by reference. Li et al. have reported a trithiol-capped oligonucleotide that can stabilize gold metal nanoparticles having diameters=100 nm, while retaining hybridization properties that are comparable to acyclic or dithiol-oligonucleotide modified particles [Z. Li, R. C. Jin, C. A. Mirkin and R. L. Letsinger, *Multiple thiol-anchor capped DNA-gold nanoparticle conjugates. Nucleic Acids Res.* 30 (2002), pp. 1558-1562], the entire contents of which are incorporated herein by reference.

In general silver nanoparticles cannot be effectively passivated by alkylthiol-modified oligonucleotides using the established experimental protocols that were developed for gold particles. One method of generating core-shell particles having a core of silver and a thin shell of gold has allowed silver nanoparticles to be readily functionalized with alkylthiol-oligonucleotides using the proven methods used to prepare pure gold particle-oligonucleotide conjugates. [Y. W. Cao, R. Jin and C. A. Mirkin, *DNA-modified core-shell Ag/Au nanoparticles. J. Am. Chem. Soc.* 123 (2001), pp. 7961-7962], the entire contents of which are incorporated herein by reference.

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6] the entire contents of which are incorporated herein by reference. After self-assembled monolayer (SAM) formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds.

Such bonding schemes have applications not only by providing a mechanism by which the nanoparticles can be controllably dispersed and delivered within a medium, but may also play a role in the formation of the encapsulated structures of the invention, as detailed above.

Spectral Range of Light Used for PEPST

A plasmonics enhanced effect can occur throughout the electromagnetic region provided the suitable nanostructures, nanoscale dimensions, metal types are used. Therefore, the PEPST concept can be utilized for the entire electromagnetic spectrum, i.e, energy, ranging from gamma rays and X rays throughout ultraviolet, visible, infrared, microwave and radio frequency energy. However, for practical reasons, visible and NIR light are used for silver and gold nanoparticles, since the plasmon resonances for silver and gold occur in the visible and NIR region, respectively. Especially for gold nanoparticles, the NIR region is very appropriate for the delivery of energy into a medium where otherwise optical scatter at shorter wavelengths would present a problem, such as for example in the treatment of waste water or the sterilization of food products having high concentrations of suspended solids.

Photon Excitation

There are several methods of the invention for using light to excite photoactivate compounds in the medium. One can use light having wavelengths within the so-called "window" (designed to penetrate any container holding the medium to be processed and/or to transmit through the medium). Moreover, while certain aspects of the invention prefer that the excitation light be nominally non-absorbing in the medium, due to the plasmonic advantages, the invention is still useful in mediums where there is considerable scatter and absorption. For example, in the above-noted, UV applications, the plasmonic enhanced PEPST probes could be introduced into the medium and UV light could be used as the activation source. While in the region of the medium near the surface, the PEPST probes may not play a dominant role, in regions deeper into the surface where the UV light has become attenuated, the PEPST probes will play a significant role in photoinitiation or photo-catalyst.

Figure 10:
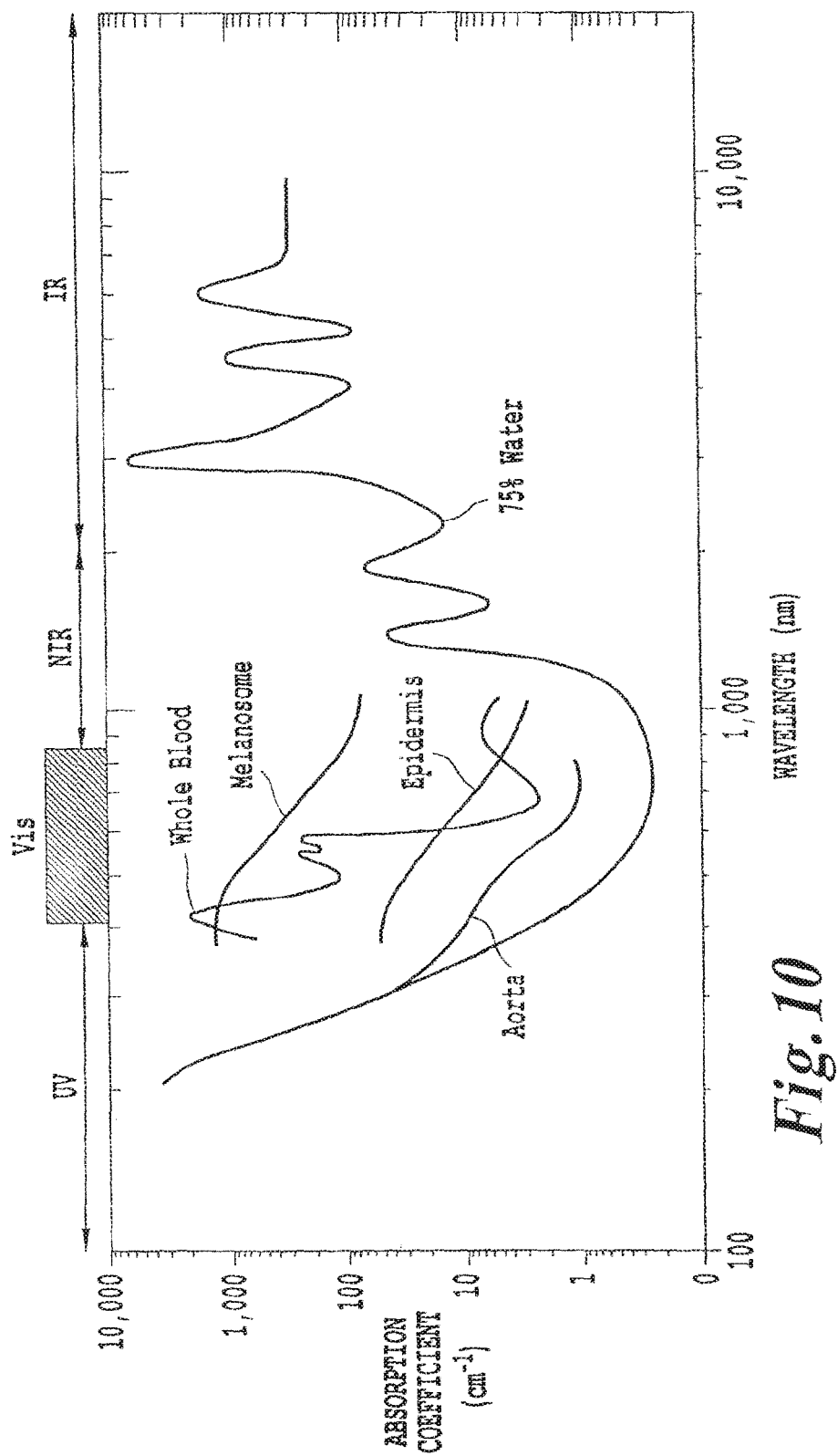
FIG. 10 is a representation of the "window" in hydrous medium.

The ability of light to penetrate the medium depends on absorption and scatter. Within the hydrous medium, a window extends from 600 to 1300 nm, from the orange/red region of the visible spectrum into the NIR. At the short-wavelength end, absorbing biomolecules become important, including DNA and the amino acids tryptophan and tyrosine. At the infrared (IR) end of the window, penetration is limited by the absorption properties of water. Within the window, scattering is dominant over absorption, and so the propagating light becomes diffuse, although not necessarily entering into the diffusion limit. FIG. 10 shows a diagram of the window for an hydrous medium. The following section discusses the use of one-photon and multi-photon techniques.

Light Excitation Methods: Single-Photon and Multi-Photon Excitation

Two methods can be used, one-photon or multi-photon excitation. If the two-photon technique is used, one can excite the PA molecules with light at 700-1000 nm, which can penetrate deep inside the medium, in order to excite molecules that absorb in the 350-500 nm spectral region. This approach can excite compounds, which absorb in the 290-350 nm spectral region and emit in the visible. With the one-photon method, the photo-activator (PA) molecules can directly absorb excitation light at 600-1300 nm. In this case we can design a system having additional aromatic rings or other conjugation to alter the ability to absorb at different wavelengths.

X Ray Excitation

Although X-ray can excite compounds in a medium non-invasively, X-ray is not easily absorbed by many of the compounds where energy modulation is desired. This invention provides a solution to this problem, by the providing of a molecular system that can absorb the X-ray energy and change that energy into other energies that can be used. More specifically, one example of a molecular system that can absorb and change the X-ray energy in this invention is the PEPST probes including nanoparticles (as described above).

In this embodiment, the invention uses X-rays for excitation. The advantage is the ability to excite molecules non-invasively since X-ray can penetrate deep in the medium. In one embodiment of the invention, a PA molecule (e.g., a photoinitiator) is bound to a molecular entity, referred to as an "energy modulation agent" that can interact with the X-rays, and then the emitted light that can be absorbed by the PA molecules. (FIG. 11)

PEPST Probes for X Ray Excitation

In the previous sections, the advantage of gold nanoparticles as plasmonics-active systems have been discussed. Furthermore, gold nanoparticles are also suitable energy modulation agent systems since they are biocompatible and have been shown to be a possible candidate for contrast agents for X-ray [Hainfeld et al. *The British Journal of radiology.* 79, 248, 2006], the entire contents of which are incorporated herein by reference. The concept of using high-Z materials for dose enhancement in cancer radiotherapy was advanced over 20 years ago. The use of gold nanoparticles as a dose enhancer seems more promising than the earlier attempts using microspheres and other materials for two primary reasons. First, gold has a higher Z number than iodine (I, Z=53) or gadolinium (Gd, Z=64), while showing little toxicity, up to at least 3% by weight, on either the rodent or human tumour cells. The gold nanoparticles were non-toxic to mice and were largely cleared from the body through the kidneys. This novel use of small gold nanoparticles permits material which may incidentally uptake some of these nanoparticles to remain safe for human consumption.

FIG. 12 shows a number of the various embodiments of PEPST probes that can be preferably used for X ray excitation of energy modulation agent-PA system. These probes comprise:

(A) PA molecules bound to energy modulation agent and to plasmonic metal nanoparticle;
(B) Plasmonic metal nanoparticle with energy modulation agent nanocap covered with PA molecules;
(C) PA-covered nanoparticle with plasmonic metal nanoparticles;
(D) Energy modulation agent-containing nanoparticle covered with PA molecules and plasmonic metal nanocap;
(E) Plasmonic metal nanoparticle core with energy modulation agent nanoshell covered with PA molecule; and
(F) PA molecule bound to energy modulation agent (attached to plasmonics metal nanoparticle) nanoparticle by detachable biochemical bond.

Examples of PEPST System Based on Energy Modulation Agent-PA

For purposes of simplification, the following discussion is centered on gold as the metal material and CdS as the energy modulation agent material (which can also be used as DNA stabilized CdS, see Ma et al. *Langmuir,* 23 (26), 12783-12787 (2007), the entire contents of which are incorporated herein by reference). However, it is to be understood that many other embodiments of metal material, energy modulation agent and PA molecule are possible within the bounds of the invention, and the following discussion is for exemplary purposes only.

In the embodiment of FIG. 12A, the PEPST system comprises gold nanoparticles, an energy modulation agent nanoparticle (e.g., CdS) linked to a PA drug molecule (e.g., psoralen). X ray is irradiated to CdS, which absorbs X rays

[Hua et al., *Rev. Sci. Instrum.*, 73, 1379, 2002, the entire contents of which are incorporated herein by reference] and emits CdS XEOL light (at 350-400 nm) that is plasmonics-enhanced by the gold nanoparticle. This enhanced XEOL light can be used to photoactivate PA molecules. In this case the nanostructure of the gold nanoparticle is designed to enhance the XEOL light at 350-400 nm.

In the embodiment of FIG. 12B, the PEPST system comprises a plasmonics-active metal (gold) nanoparticle with energy modulation agent nanocap (CdS) covered with PA molecules. X ray is irradiated to CdS, which absorbs X ray and emits XEOL light that is plasmonics-enhanced by the gold nanoparticle. This enhanced XEOL light is used to photoactivate the PA molecule.

In the embodiment of FIG. 12C, the PEPST system comprises a PA (e.g., psoralen)-covered CdS nanoparticle with smaller plasmonic metal (gold) nanoparticles. X ray is irradiated to CdS, which absorbs X ray and emits XEOL light that is plasmonics-enhanced by the gold nanoparticle. This enhanced XEOL light is used to photoactivate the PA molecule.

In the embodiment of FIG. 12D, the energy modulation agent core comprises CdS or CsCl nanoparticles covered with a nanocap of gold. X ray is irradiated to CdS or CsCl, which absorbs X ray [[Jaegle et al. *J. Appl. Phys.*, 81, 2406, 1997] and emits XEOL light that is plasmonics-enhanced by the gold nanocap structure. This enhanced XEOL light is used to photoactivate the PA molecule.

Similarly, the embodiment in FIG. 12E comprises a spherical gold core covered by a shell of CdS or CsCl. X ray is irradiated to CdS or CsCl material, which absorbs X ray [Jaegle et al. *J. Appl. Phys.*, 81, 2406, 1997 the entire contents of which are incorporated herein by reference] and emits XEOL light that is plasmonics-enhanced by the gold nanosphere. This enhanced XEOL light is used to photoactivate the PA molecule.

In the embodiment of FIG. 12F, the PEPST system comprises gold nanoparticles, and an energy modulation agent nanoparticle (e.g., CdS) linked to a PA drug molecule (e.g., psoralen) by a link that can be detached by radiation. X ray is irradiated to CdS, which absorbs X ray and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In alternative embodiments, the metal nanoparticles or single nanoshells are replaced by multi layers of nanoshells [Kun Chen. Yang Liu. Guillermo Ameer, Vadim Backman, *Optimal design of structured nanospheres for ultrasharp light-scattering resonances as molecular imaging multilabels. Journal of Biomedical Optics*, 10(2, 024005 (March/April 2005), the entire contents of which are incorporated herein by reference].

In other alternative embodiments the metal nanoparticles are covered with a layer (1-30 nm) of dielectric material (e.g. silica). The dielectric layer (or nanoshell) is designed to prevent quenching of the luminescence light emitted by the energy modulation agent (also referred to as EEC) molecule(s) due to direct contact of the metal with the energy modulation agent molecules. In yet other alternative embodiments, the energy modulation agent molecules or materials are bound to (or in proximity of) a metal nanoparticle via a spacer (linker). The spacer is designed to prevent quenching of the luminescence light emitted by the energy modulation agent molecules or materials.

Other Useable Materials

The energy modulation agent materials can include any materials that can absorb X ray and emit light in order to excite the PA molecule. The energy modulation agent materials include, but are not limited to:

metals (gold, silver, etc);
quantum dots;
semiconductor materials;
scintillation and phosphor materials;
materials that exhibit X-ray excited luminescence (XEOL);
organic solids, metal complexes, inorganic solids, crystals, rare earth materials (lanthanides), polymers, scintillators, phosphor materials, etc.; and
materials that exhibit excitonic properties.

Quantum dots, semiconductor nanostructures. Various materials related to quantum dots, semiconductor materials, etc. can be used as energy modulation agent systems. For example CdS-related nanostructures have been shown to exhibit X-ray excited luminescence in the UV-visible region [Hua et al. *Rev. Sci. Instrum.*, 73, 1379, 2002, the entire contents of which are incorporated herein by reference].

Scintillator materials as energy modulation agent systems. Various scintillator materials can be used as energy modulation agents since they absorb X-ray and emit luminescence emission, which can be used to excite the PA system. For example, single crystals of molybdates can be excited by X-ray and emit luminescence around 400 nm [Mirkhin et al. *Nuclear Instrum. Meth. In Physics Res. A*, 486, 295 (2002, the entire contents of which are incorporated herein by reference].

Solid materials as energy modulation agent systems: Various solid materials can be used as energy modulation agents due to their X-ray excited luminescence properties. For example CdS (or CsCl) exhibit luminescence when excited by soft X-ray [Jaegle et al, *J. Appl. Phys.*, 81, 2406, 1997, the entire contents of which are incorporated herein by reference].

XEOL materials: lanthanides or rare earth materials; see L. Soderholm, G. K. Liu, Mark R. Antonioc, F. W. Lytle, *X-ray excited optical luminescence .XEOL. detection of x-ray absorption fine structure .XAbZ. J. Chem. Phys.* 109, 6745, 1998, the entire contents of which are incorporated herein by reference or, Masashi Ishiia, Yoshihito Tanaka and Tetsuya Ishikawa, Shuji Komuro and Takitaro Morikawa, Yoshinobu Aoyagi. *Site-selective x-ray absorption fine structure analysis of an optically active center in Er-doped semiconductor thin film using x-ray-excited optical luminescence. Appl. Phys. Lett,* 78, 183, 200, the entire contents of which are incorporated herein by reference.

Figure 13A:
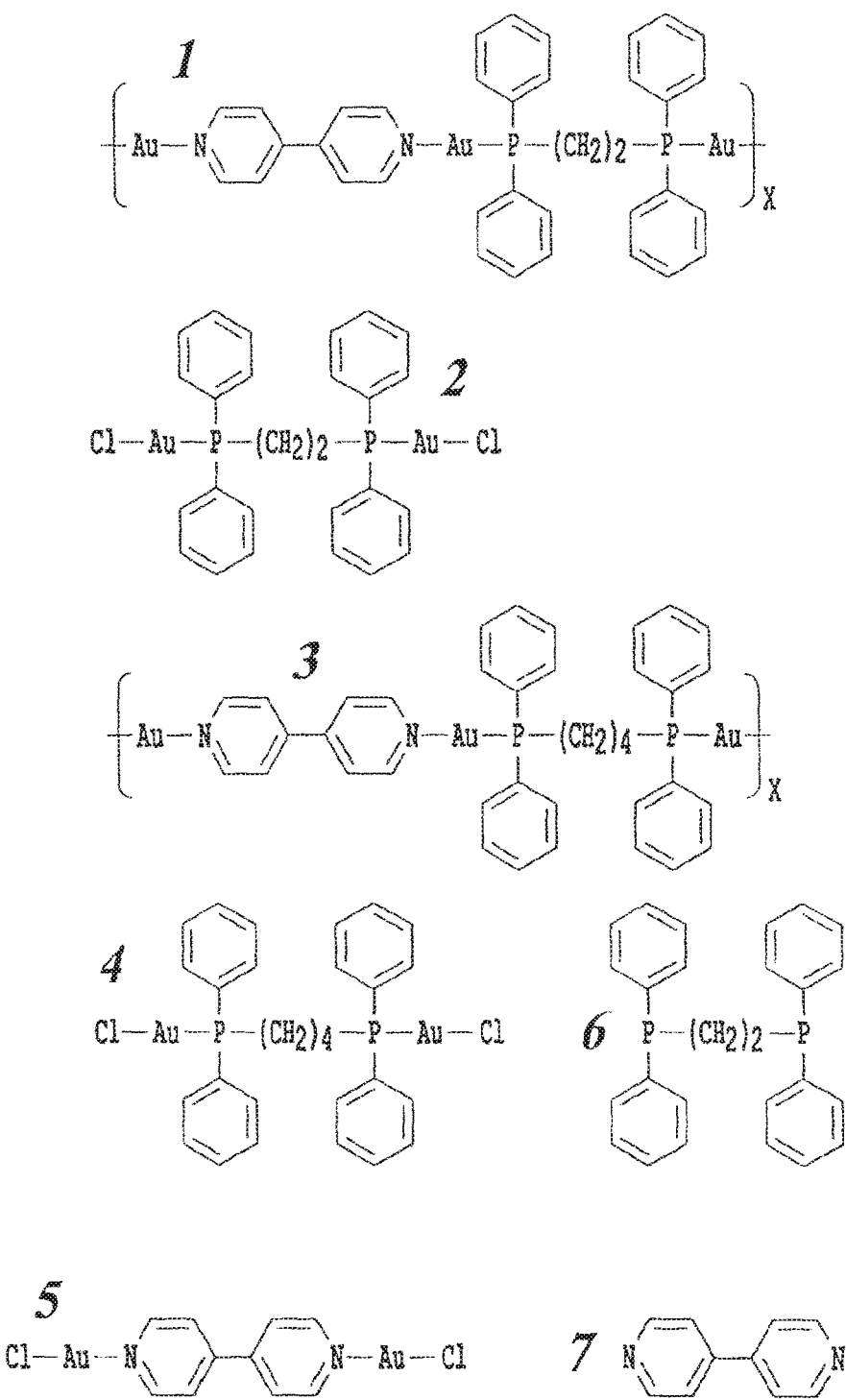
Figure 14:
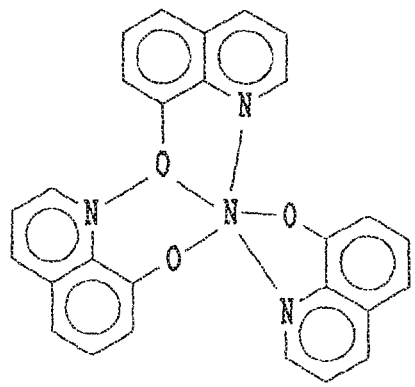
FIG. 14 shows the structure of a further embodiment of compound exhibiting XEOL, namely a tris-8-hydroxyquinoline-aluminum complex.

Some examples of metal complexes exhibiting XEOL which can be used as energy modulation agent systems are shown in FIGS. 13 and 14. Such structures can be modified by replacing the metal atom with metal nanoparticles in order to fabricate a plasmonics-enhance PEPST probe. In the invention, the experimental parameters including size, shape and metal type of the nano structure can be selected based upon the excitation radiation (NIR or X ray excitation), the photoactivation radiation (UVB), and/or the emission process from the energy modulation agent system (visible NIR).

Principle of Plasmonics-Enhancement Effect of the PEPST Probe Using X-Ray Excitation One embodiment of the basic PEPST probe embodiment comprises PA molecules bound to an energy modulation agent and to plasmonic metal (gold) nanoparticles. The metal nanoparticle can play 2 roles:

(A) Enhancement of the X-ray electromagnetic field
(B) Enhancement of the emission signal of the energy modulation agent system.

The X ray radiation, used to excite the energy modulation agent system, is amplified by the metal nanoparticle due to plasmon resonance. As a result the energy modulation agent system exhibits more emission light that is used to photo-activate the PA molecules and make them photoactive. In this case the metal nanoparticles are designed to exhibit strong plasmon resonance at or near the X ray wavelengths. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes described above.

Figure 15:
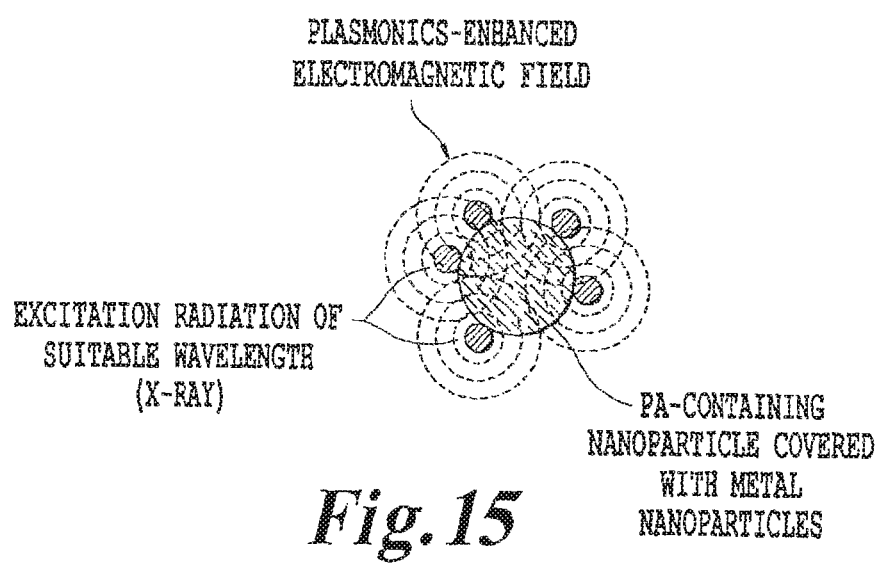
FIG. 15 is a representation of a plasmonics-enhanced mechanism for a photo-active energy modulation agent-PA probe of the invention.
Figure 18A:
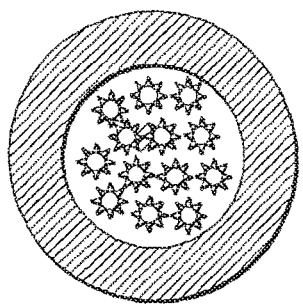
FIGS. 18A-18D provides a representation of the sequence for use of encapsulated photoactive agents.
Figure 18B:
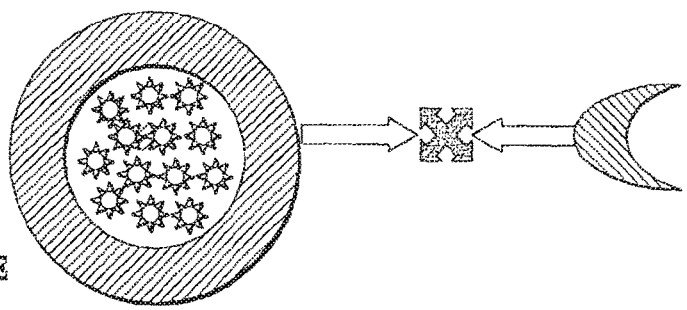
Figure 18C:
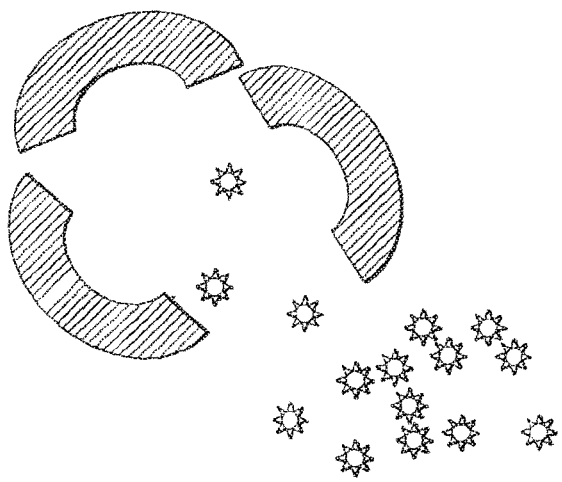
Figure 18D:
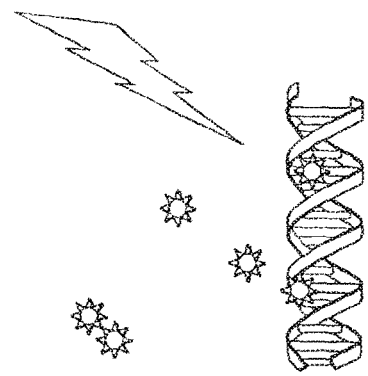

FIG. 15 illustrates the plasmonics-enhancement effect of the PEPST probe. X-ray used in medical diagnostic imaging has photon energies from approximately 10 to 150 keV, which is equivalent to wavelengths range from 1.2 to 0.0083 Angstroms. [λ(Angstrom)=12.4/E (keV)]. Soft X ray can go to 10 nm. The dimension of plasmonics-active nanoparticles usually have dimensions on the order or less than the wavelengths of the radiation used. Note that the approximate atomic radius of gold is approximately 0.15 nanometers. At the limit, for gold the smallest "nanoparticle" size is 0.14 nm (only 1 gold atom). A nanoparticle with size in the hundreds of nm will have approximately $10^6$-$10^7$ gold atoms. Therefore, the range of gold nanoparticles discussed in this invention can range from 1-$10^7$ gold atoms.

The gold nanoparticles can also enhance the energy modulation agent emission signal, which is use to excite the PA molecule. For psoralens, this spectral range is in the UVB region (320-400 nm). Silver or gold nanoparticles, nanoshell and nanocaps have been fabricated to exhibit strong plasmon resonance in this region. FIG. 16 shows excitation and emission fluorescence spectra of a psoralen compound (8-methoxypsoralen).

Nanoparticle Chain for Dual Plasmonics Effect

As discussed previously, there is the need to develop nanoparticle systems that can have dual (or multi) plasmonics resonance modes. FIG. 17 illustrates an embodiment of the invention PEPST probe having a chain of metal particles having different sizes and coupled to each other, which could exhibit such dual plasmonics-based enhancement. For example the parameters (size, metal type, structure, etc) of the larger nanoparticle (FIG. 17, left) can be tuned to NIR, VIS or UV light while the smaller particle (FIG. 17, right) can be tuned to X ray. There is also a coupling effect between these particles.

These nanoparticle chains are useful in providing plasmonics enhancement of both the incident radiation used (for example, x-ray activation of CdS) as well as plasmonics enhancement of the emitted radiation that will then activate the PA. Similar nanoparticles systems have been used as nanolens [*Self-Similar Chain of Metal Nanospheres as an Efficient Nanolens*, Kuiru Li, Mark I. Stockman, and David J. Bergman, *Physical Review Letter*. VOLUME 91. NUMBER 22, 227402-1, 2003, the entire contents of which are incorporated herein by reference].

Fabrication of Gold Nanoparticles:

The Frens method [Frens, G., *Controlled nucleation for the regulation of the particle size in monodisperse gold solutions*. Nature (London) Phys Sci., 1973, 241: p. 20-22, the entire contents of which are incorporated herein by reference] can be used in the invention to synthesize a solution of gold nanoparticles ranging in diameter from 8-10 nm. Briefly, $5.0 \times 10^{-6}$ mol of $HAuCl_4$ is dissolved in 19 ml of deionized water producing a faint yellowish solution. This solution is heated with vigorous stirring in a rotary evaporator for 45 minutes. 1 ml of 0.5% sodium citrate solution is added and the solution is stirred for an additional 30 minutes. The color of the solution gradually changed from the initial faint yellowish to clear, grey, purple and finally a tantalizing wine-red color similar to merlot. The sodium citrate used serves in a dual capacity, first acting as a reducing agent, and second, producing negative citrate ions that are adsorbed onto the gold nanoparticles introducing surface charge that repels the particles and preventing nanocluster formation.

Another method for synthesizing gold nanoparticles involves stabilization by horse spleen apoferritin (HSAF) has been reported using $NaBH_4$ or 3-(N-morpholino) propanesulfonic acid (MOPS) as the reducing agent [Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, Vol. 101, 1719-1729, 2007, the entire contents of which are incorporated herein by reference]. Gold sulfite ($Au_2S$) nanoparticles were prepared in the cavity of the cage-shaped protein, apoferritin. Apoferritin has a cavity, 7 nm in diameter, and the diameter of fabricated $Au_2S$ nanoparticles is about the same size with the cavity and size dispersion was small. [Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, Vol. 35 (2006), No. 10 p. 1192, the entire contents of which are incorporated herein by reference]. Thus, in one embodiment, the PA or energy modulation agent-PA compounds are encapsulated inside the apoferrtin shells.

Excitons in Solid Materials

Excitons are often defined as "quasiparticles" inside a solid material. In solid materials, such as semiconductors, molecular crystals and conjugated organic materials, light excitation at suitable wavelength (such as X ray, UV and visible radiation, etc) can excite electrons from the valence band to the conduction band. Through the Coulomb interaction, this newly formed conduction electron is attracted, to the positively charged hole it left behind in the valence band. As a result, the electron and hole together form a bound state called an exciton. (Note that this neutral bound complex is a "quasiparticle" that can behave as a boson—a particle with integer spin which obeys Bose-Einstein statistics: when the temperature of a boson gas drops below a certain value, a large number of bosons 'condense' into a single quantum state—this is a Bose-Einstein condensate (BEC). Exciton production is involved in X-ray excitation of a solid material. Wide band-gap materials are often employed for transformation of the x-ray to ultraviolet/visible photons in the fabrication of scintillators and phosphors [Martin Nikl. *Scintillation detectors for x-rays. Meas. Sci. Technol.* 17 (2006) R37-R54 the entire contents of which are incorporated herein by reference]. The theory of excitons is well known in materials research and in the fabrication and applications of semiconductors and other materials.

During the initial conversion a multi-step interaction of a high-energy X-ray photon with the lattice of the scintillator material occurs through the photoelectric effect and Compton scattering effect; for X-ray excitation below 100 keV photon energy the photoelectric effect is the main process. Many excitons (i.e., electron-hole pairs) are produced and thermally distributed in the conduction bands (electrons) and valence bands (holes). This first process occurs within less than 1 ps. In the subsequent transport process, the excitons migrate through the material where repeated trapping at defects may occur, leading to energy losses due to nonradiative recombination, etc. The final stage, luminescence, consists in consecutive trapping of the electron-hole pairs at the luminescent centers and their radiative recombination. The electron-hole pairs can be trapped at the defects and recombine, producing luminescent. Luminescent dopants can also be used as traps for exciton.

Exciton Traps

Exciton traps can be produced using impurities in the crystal host matrix. In impure crystals with dipolar guest molecules, electron trap states may arise when an electron is localized on a neighbor of the impurity molecule. Such traps have been observed in anthracene doped with carbazole [Kadshchuk. A. K., Ostapenko. N. I., Skryshevskii. Yu. A., Sugakov, V. I. and Susokolova, T. O., *Mol. Cryst. and Liq. Cryst.*, 201, 167 (1991) the entire contents of which are incorporated herein by reference]. The formation of these traps is due to the interaction of the dipole moment of the impurity with charge carrier. When the concentration of the dopant (or impurities) is increased, spectra exhibit additional structure of spectrum due to the trapping of carriers on clusters of impurity molecules. Sometimes, impurities and dopants are not required: The electron or exciton can also be trapped on a structural defect in such crystals due to the electrostatic interaction with reoriented dipole moment of disturbed crystal molecules [S. V. Izvekov. V. I. Sugakov. *Exciton and Electron Traps on Structural Defects in Molecular Crystals with Dipolar Molecules, Physica Scripta.* Vol. T66, 255-257, 1996]. One can design structural defects in molecular crystals that serve as exciton traps. The development of GaAs/AlGaAs nanostructures and use of nanofabrication technologies can permit engineered exciton traps with novel quantum mechanical properties in materials to be used in the invention.

Design, Fabrication and Operation of EIP Probes

FIG. 18A-D shows various embodiments of EIP probes that can be designed:

(A) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have structural defects that serve as traps for excitons.

(B) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have impurities or dopant molecules that serve as traps for excitons.

EIP Probes with Tunable Emission:

The probes as described above in (B) provide the capability to tune the energy conversion from an X ray excitation source into a wavelength of interest to excite the PA molecules. In 1976, D'Silva et al demonstrated that polynuclear aromatic hydrocarbons (PAH) molecules doped in a frozen n-alkane solids could be excited by X-ray and produce luminescence at visible wavelengths characteristics of their luminescence spectra. [A. P. D'Silva, G. J. Oestreich, and V. A. Fassel, *X-ray excited optical luminescence of polynuclear aromatic hydrocarbons. Anal. Chem.;* 1976; 48(6) pp 915-917, the entire contents of which are incorporated herein by reference]. Tunable EIP probes can be designed to contain such luminescent dopants such as highly luminescent PAHs exhibiting luminescence emission in the range of 300-400 nm suitable to activate psoralen. One embodiment of the EIP with tunable emission includes a solid matrix (semiconductors, glass, quartz, conjugated polymers, etc) doped with naphthalene, phenanthrene, pyrene or other compounds exhibiting luminescence (fluorescence) in the 300-400 nm range [T. Vo-Dinh. *Multicomponent analysis by synchronous luminescence spectrometry Anal. Chem.;* 1978; 50(3) pp 396-401 the entire contents of which are incorporated herein by reference]. The EEC matrix could be a semiconductor material, preferably transparent at optical wavelength of interest (excitation and emission).

Figure 19:
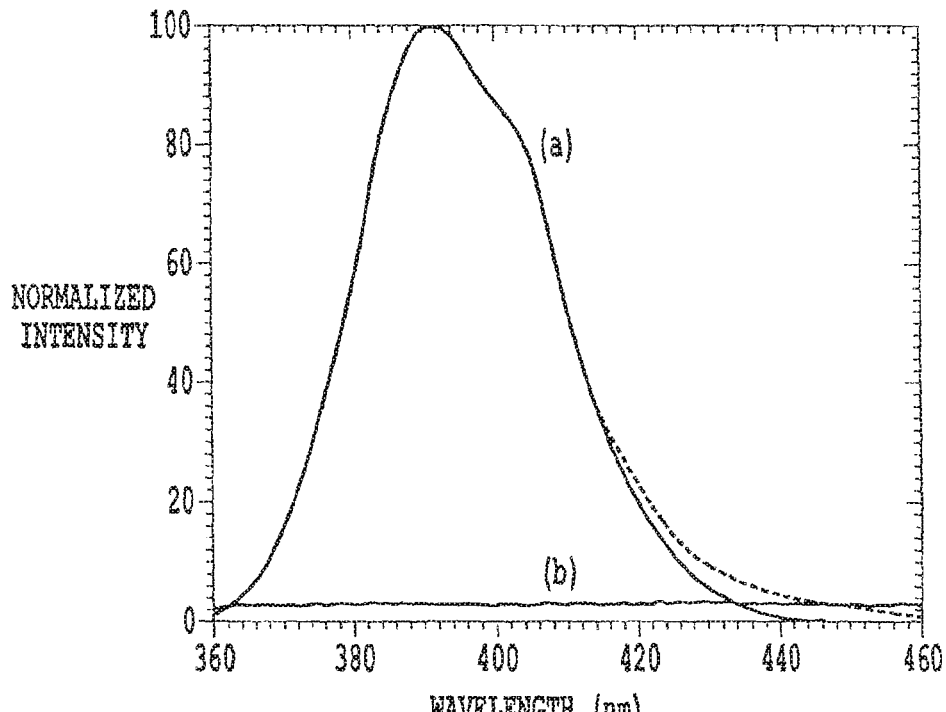
FIG. 19 is a graph showing the XEOL of Eu doped in BaFBr matrix.

Other dopant species such as rare earth materials can also be used as dopants. FIG. 19 shows the X ray excitation optical luminescence (XEOL) of Europium doped in a matrix of BaFBr, emitting at 370-420 nm. U.S. Patent Application Publication No. 2007/0063154 (hereby incorporated by reference) describes these and other nanocomposite materials (and methods of making them) suitable for XEOL.

Figure 20:
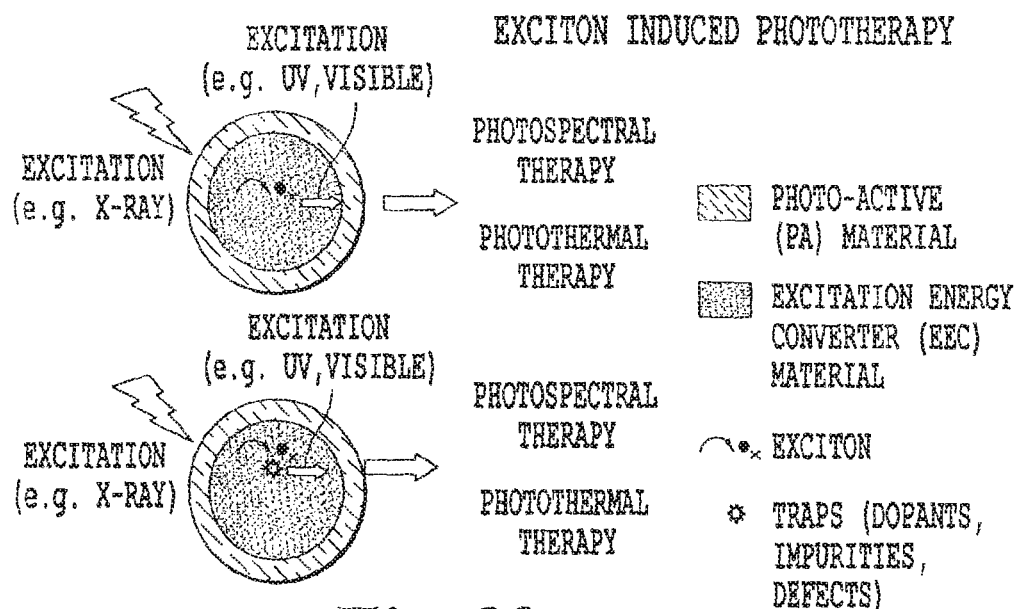
FIG. 20 shows various embodiments of EIP probes of the invention.

FIG. 20 shows various embodiments of EIP probes that can be designed:

(A) probe comprising PA molecules bound around the energy modulation agent particle or embedded in a shell around an energy modulation agent particle that can produce excitons under radiative excitation at a suitable wavelength (e.g., X-ray). In this embodiment, the energy modulation agent materials have structural defects that serve as traps for excitons.

(A) probe comprising PA molecules bound around the energy modulation agent particle or embedded in a shell around an energy modulation agent particle that can produce excitons under radiative excitation at a suitable wavelength (e.g., X-ray). In this embodiment, the energy modulation agent materials have impurities or dopant molecules that serve as traps for excitons.

A fundamental key concept in photophysics is the formation of new quasiparticles from admixtures of strongly-coupled states. Such mixed states can have unusual properties possessed by neither original particle. The coupling between excitons and plasmons can be either weak or strong. When the light-matter interaction cannot be considered as a perturbation, the system is in the strong coupling regime. A strong coupling between a surface plasmon (SP) mode and organic excitons occurs has been shown; the organic semiconductor used was a concentrated cyanine dye in a polymer matrix deposited on a silver film [Ref J. Bellessa, * C. Bonnand, and J. C. Plenet. J. Mugnier. *Strong Coupling between Surface Plasmons and Excitons in an Organic Semiconductor. Phys. Rev. Lett,* 93 (3), 036404-1, 2004, the entire contents of which are incorporated herein by reference]. Other work ahs described the photophysical properties of excitons in hybrid complexes consisting of semiconductor and metal nanoparticles. The interaction between individual nanoparticles can produce an enhancement or suppression of emission. Enhanced emission comes from electric field amplified by the plasmon resonance, whereas emission suppression is a result of energy transfer from semiconductor to metal nanoparticles. [Alexander O. Govorov. Garnett W. Bryant, ‡ Wei Zhang, Timur Skeini. Jaebeom Lee.§ Nicholas A. Kotov, Joseph M. Slocik, and Rajesh R. Naik. *Exciton-Plasmon Interaction and Hybrid Excitons in Semiconductor-Metal Nanoparticle Assemblies. Nano Lett.,* Vol. 6. No. 5, 984, 2006, the entire contents of which are incorporated herein by reference]. Other work has described a theory for the interactions between excitonic states and surface electromagnetic modes in small-diameter (<1 nm) semiconducting single-walled carbon nanotubes (CNs). [I. V. Bondarev, K. Tatur and L. M. Woods, *Strong exciton-*

*plasmon coupling in semiconducting carbon nanotube*, the entire contents of which are incorporated herein by reference].

Other work has reported about the synthesis and optical properties of a composite metal-insulator-semiconductor nanowire system which consists of a wet-chemically grown silver wire core surrounded by a $SiO_2$ shell of controlled thickness, followed by an outer shell of highly luminescent CdSe nanocrystals [Yuri Fedutik, Vasily Temnov, Ulrike Woggon, Elena Ustinovich, and Mikhail Artemyev, *Exciton-Plasmon Interaction in a Composite Metal-Insulator-Semiconductor Nanowire System. J. Am. Chem. Soc.,* 129 (48), 14939-14945, 2007, the entire contents of which are incorporated herein by reference]. For a $SiO_2$ spacer thickness of ~15 nm, they observed an efficient excitation of surface plasmons by excitonic emission of CdSe nanocrystals. For small d, well below 10 nm, the emission is strongly suppressed (PL quenching), in agreement with the expected dominance of the dipole-dipole interaction with the damped mirror dipole [G. W. Ford and W. H. Weber, *Electromagnetic interactions of molecules with metal surfaces,"* Phys. Rep. 113, 195-287 (1984), the entire contents of which are incorporated herein by reference]. For nanowire lengths up to ~10 μm, the composite metal-insulator-semiconductor nanowires (($Ag)SiO_2$)CdSe act as a waveguide for 1D-surface plasmons at optical frequencies with efficient photon out coupling at the nanowire tips, which is promising for efficient exciton-plasmon-photon conversion and surface plasmon guiding on a submicron scale in the visible spectral range.

Experiments on colloidal solutions of Ag nanoparticles covered with J-aggregates demonstrated the possibility of using the strong scattering cross section and the enhanced field associated with surface plasmon to generate stimulated emission from J-aggregate excitons with very low excitation powers. [Gregory A. Wurtz, * Paul R. Evans. William Hendren, Ronald Atkinson, Wayne Dickson, Robert J. Pollard, and Anatoly V. Zayats, *Molecular Plasmonics with Tunable Exciton-Plasmon Coupling Strength in J-Aggregate Hybridized Au Nanorod Assemblies, Nano Lett.,* Vol. 7, No. 5, 1297, 2007, the entire contents of which are incorporated herein by reference]. Their coupling to surface plasmons excitations therefore provides a particularly attractive approach for creating low-powered optical devices. This process can lead to efficient X-ray coupling for phototherapy. In addition, the coupling of J-aggregates with plasmonics structures presents genuine fundamental interest in the creation of mixed plasmon-exciton states.

Design, Fabrication and Operation of EPEP Probes

Figure 21A:
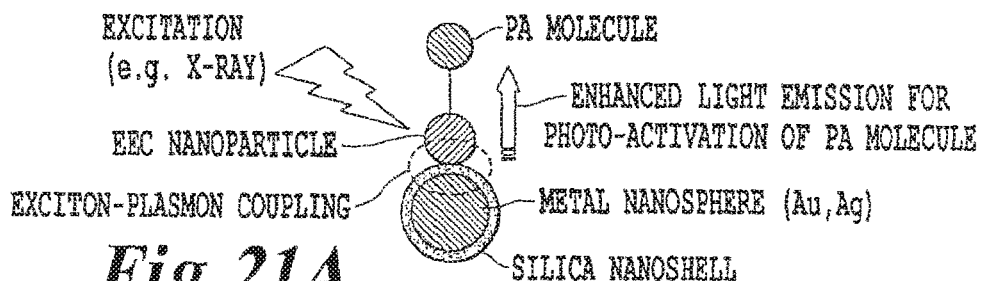
FIG. 21A-21B show further embodiments of EIP probes of the invention.
Figure 21B:
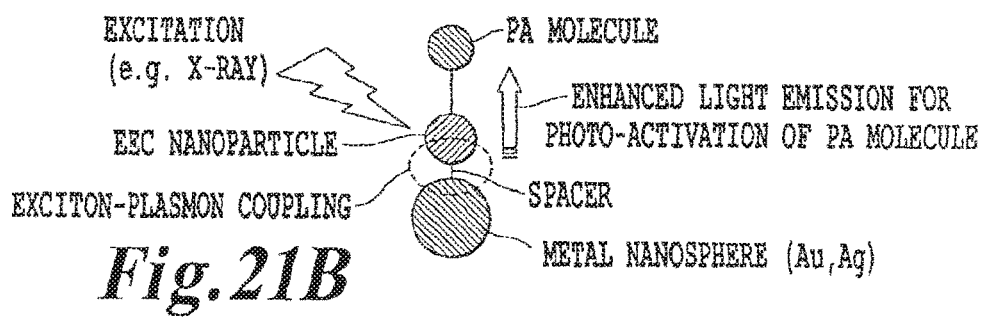

FIG. 21 shows various embodiments of EPEP probes of the invention showing the exciton-plasmon coupling:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle covered with a nanoshell of silica (or other dielectric material). The silica layer (or nanoshell) (see FIG. 25A and FIG. 25B; layer nanoshell in white between energy modulation material and metal nanostructures) is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle via a spacer (linker). The spacer is designed to prevent quenching of the luminescence light emitted by the energy modulation agent particle excited by X-ray.

Figure 22A:
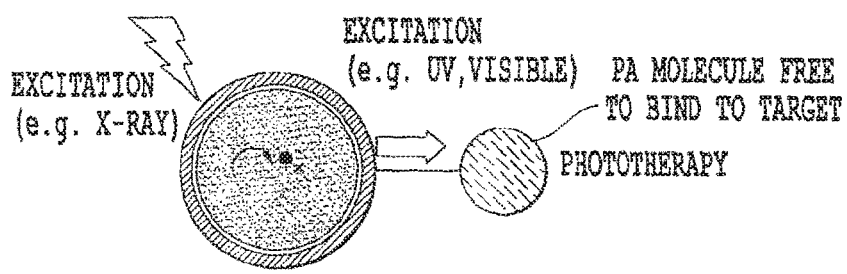
FIG. 22A-22C show further embodiments of schematic designs of EIP probes.
Figure 22B:
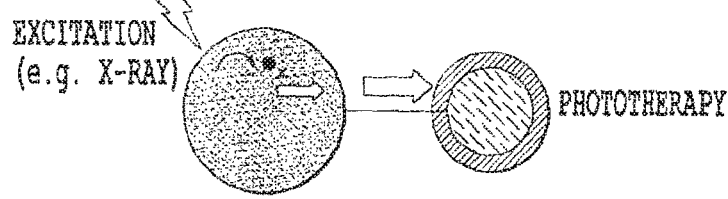
Figure 22C:
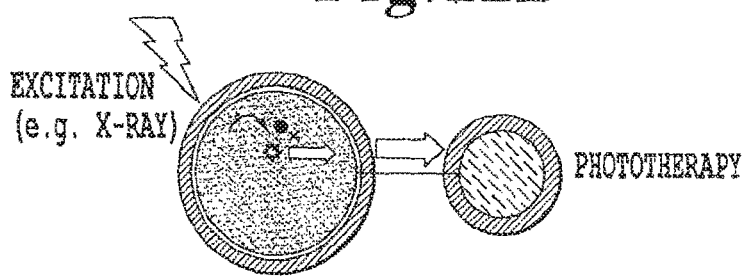

FIG. 22 shows yet further embodiments of EPEP probes of the invention:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of separate nanostructures (nano islands, nanorods, nanocubes, etc. . . . ) of metal (Au, Ag). The silica layer (or other dielectric material) is designed to prevent quenching of the luminescence light emitted by the EEC (also referred to as energy modulation agent) particle excited by X-ray. The metal nanostructures (Au, Ag, etc) are designed to induce plasmons that enhance the X ray excitation that subsequently leads to an increase in the EEC light emission, ultimately enhancing the efficiency of photoactivation. i.e. phototherapy. The structure of the nanoparticle can also be designed such that the plasmonics effect also enhance the energy modulation agent emission light. These processes are due to strong coupling between excitons (in the energy modulation agent materials and plasmons in the metal nanostructures).

(B) probe comprising a group of PA molecules in a particle bound (through a linker, which can be fixed or detachable) to an energy modulation agent particle that can produce excitons under radiative excitation at a suitable wavelength (e.g., X-ray). The PA-containing particle is covered with a layer of metallic nanostructures (Au, Ag). The metal nanostructures (Au, Ag, etc) are designed to induce plasmons that enhance the energy modulation agent light emission, ultimately enhancing the efficiency of photoactivation, i.e. phototherapy.

(C) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of metallic nanostructures (Au, Ag). The silica layer (or other dielectric material) is designed to prevent quenching of the luminescence light emitted by the energy modulation agent particle excited by X-ray. The metal nanostructures (Au, Ag, etc) are designed to induce plasmons that enhance the X ray excitation that subsequently leads to an increase in the energy modulation agent light emission, ultimately enhancing the efficiency of photoactivation. In addition, the PA-containing particle is covered with a layer of metallic nanostructures (Au, Ag). The metal nanostructures (Au, Ag, etc) are designed to induce plasmons that enhance the EEC light emission, ultimately enhancing the efficiency of photoactivation.

Hybrid EPEP Nano-Superstructures

EPEP probes can also comprise hybrid self-assembled superstructures made of biological and abiotic nanoscale components, which can offer versatile molecular constructs with a spectrum of unique electronic, surface properties and photospectral properties for use in phototherapy.

Biopolymers and nanoparticles can be integrated in superstructures, which offer unique functionalities because the physical properties of inorganic nanomaterials and the chemical flexibility/specificity of polymers can be used. Noteworthy are complex systems combining two types of excitations common in nanomaterials, such as excitons and plasmons leading to coupled excitations. Molecular constructs comprising building blocks including metal, semiconductor nanoparticles (NPs), nanorods (NRs) or nanowires (NWs) can produce EPEP probes with an assortment of photonic properties and enhancement interactions that are fundamentally important for the field of phototherapy. Some examples of assemblies of some NW nanostructures and NPs have been reported in biosensing. Nanoscale superstructures made from CdTe nanowires (NWs) and metal nanoparticles (NPs) are prepared via bioconjugation reactions. Prototypical biomolecules, such as D-biotin and streptavidin pair, were utilized to connect NPs and NWs in solution. It was found that Au NPs form a dense shell around a CdTe NW. The superstructure demonstrated unusual optical effects related to the long-distance interaction of the semiconductor and noble metal nanocolloids. The NW?NP complex showed 5-fold enhancement of luminescence intensity and a blue shift of the emission peak as compared to unconjugated NW. [Jaebeom Lee, † Alexander O. Govorov. John Dulka, and Nicholas A. Kotov, *Bioconjugates of CdTe Nanowires and Au Nanoparticles: Plasmon-Exciton Interactions, Luminescence Enhancement, and Collective Effects. Nano Lett.*, Vol. 4, No. 12, 2323, 2004, the entire contents of which are incorporated herein by reference].

Figure 23A:
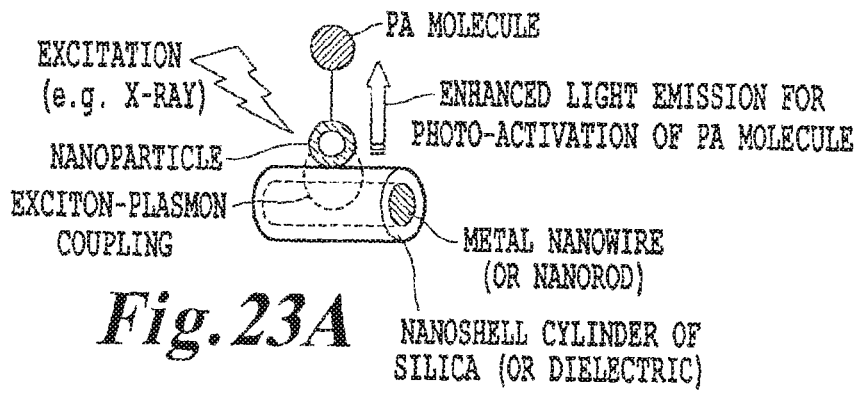
FIGS. 23A and 23B are representations of various embodiments of basic EPEP probes.
Figure 23B:
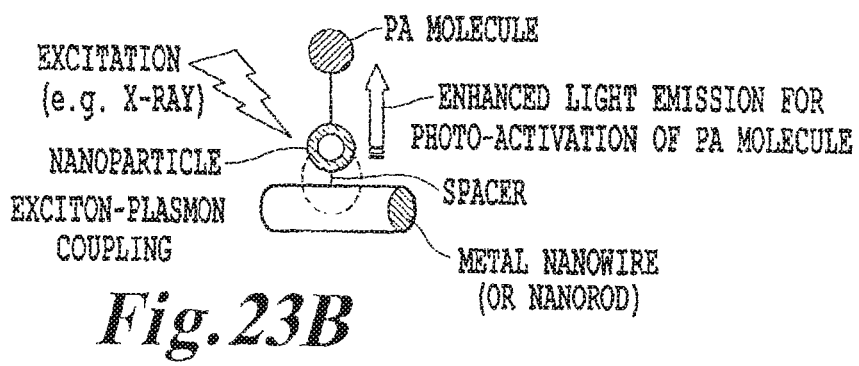

FIG. 23 shows various embodiments of EPEP probes of the invention comprising superstructures of NPs, NWs and NRs:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanowire (or nanorod) covered with a nanoshell cylinder of silica (or other dielectric material). The silica nanoshells cylinder is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect and/or the exciton-plasmon coupling (EPC) effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticles via a spacer (linker). The spacer is designed to prevent quenching of the luminescence light emitted by the energy modulation agent particle excited by X-ray. Same effect as above in (A).

Figure 24:
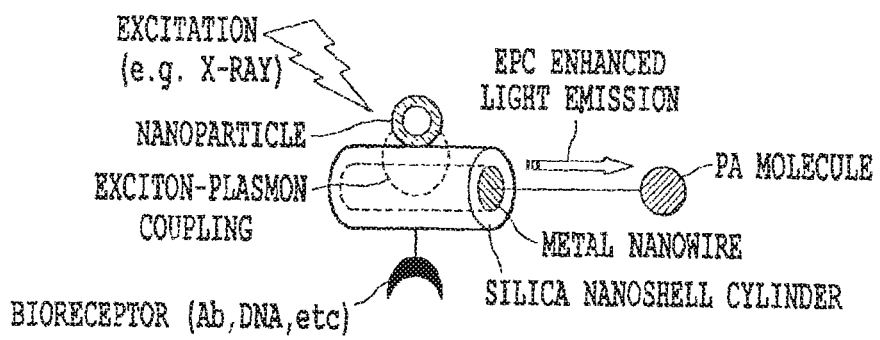
FIG. 24 is a representation of one embodiment of EPEP probes having NPs, NWs and NR.
Figure 25:
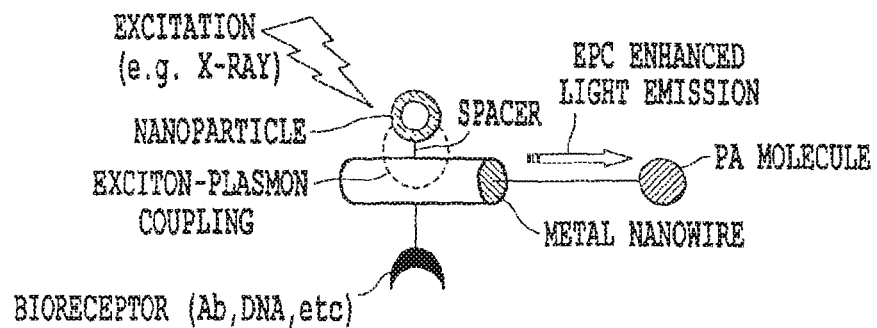
FIG. 25 is a representation of one embodiment of EPEP probes having NPs, NWs, NRs and bioreceptors.

FIGS. 24 and 25 shows another set of embodiments of EPEP probes of the invention comprising superstructures of NPs, NWs and NRs and bioreceptors (antibodies, DNA, surface cell receptors, etc.). The use of bioreceptors to target tumor cells has been discussed previously above in relation to PEPST probes. Note that in this embodiment the PA molecules are attached along the NW axis in order to be excited by the emitting light form the NWs.

Figure 26:
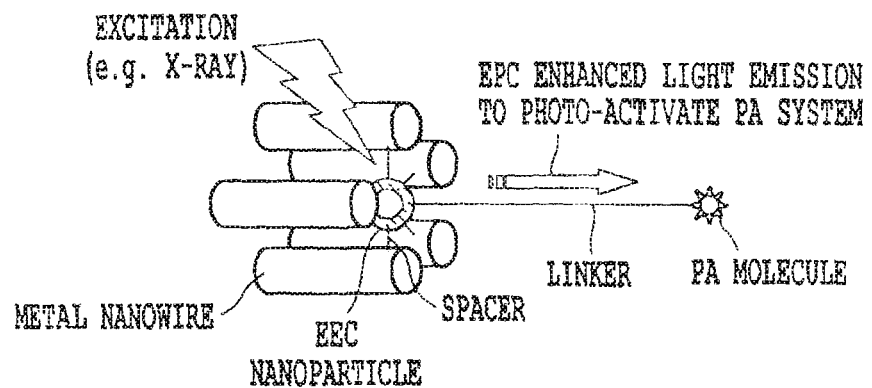
FIG. 26 is a representation of an embodiment of EPEP probes having NPs and multiple NWs.

FIG. 26 shows another embodiment of EPEP probes of the invention including superstructures of NPs linked to multiple NWs.

For some embodiments, by adding metal nanostructures designed to interact specifically with the excitons in the energy modulation agent system, there are significant improvements:

(1) an additional radiative pathway from exciton to photon conversion is introduced (2) the metal nanostructures can be designed to amplify (due to the plasmonics effect) the excitation radiation (e.g., X-ray) and/or the emission radiation (e.g, UV or visible) to excite the photo-active (PA) molecule, thereby enhancing the PA effectiveness.

Figure 4:
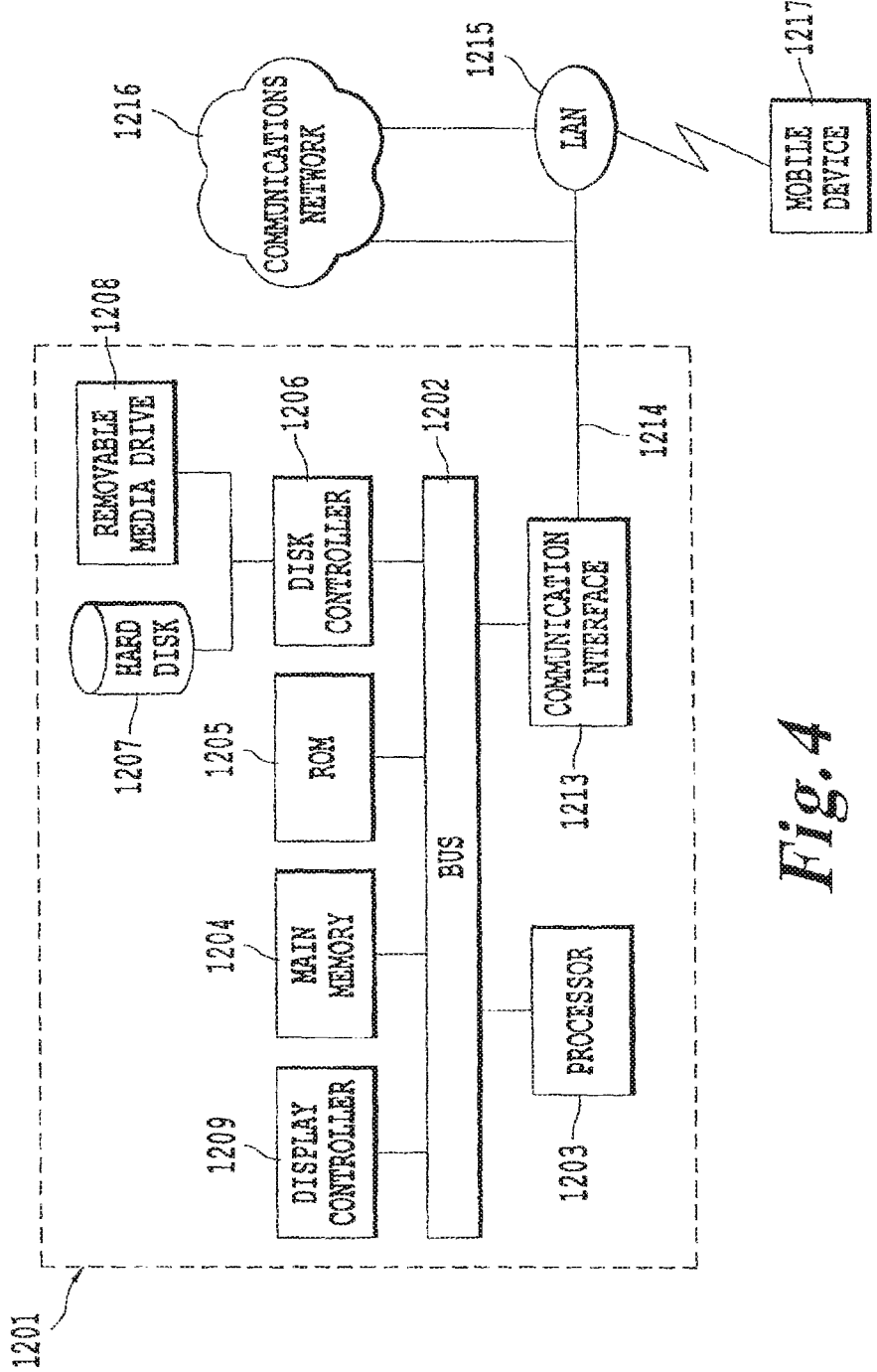
FIG. 4 illustrates an exemplary computer system for implementing various embodiments of the invention.

Various metallic nanostructures that can be used in EPEP probe embodiments of the invention are the same as those illustrated in FIG. 4 for the PEPST probes.

EPEP Probes with Microresonators

In one embodiment, the energy modulation agent system can be designed to serve also as a microresonator having micron or submicron size. Prior work has described a resonant microcavity and, more particularly, to a resonant microcavity which produces a strong light-matter interaction [M. Lipson; L. C. Kimerling; Lionel C. Resonant microcavities. U.S. Pat. No. 6,627,923, 2000, the entire contents of which are incorporated herein by reference]. A resonant microcavity, typically, is formed in a substrate, such as silicon, and has dimensions that are on the order of microns or fractions of microns. The resonant microcavity contains optically-active matter (i.e., luminescent material) and reflectors which confine light in the optically-active matter. The confined light interacts with the optically-active matter to produce a light-matter interaction. The light-matter interaction in a microcavity can be characterized as strong or weak. Weak interactions do not alter energy levels in the matter, whereas strong interactions alter energy levels in the matter. In strong light-matter interaction arrangements, the confined light can be made to resonate with these energy level transitions to change properties of the microcavity.

Experimental Methods

Preparation of Nanoparticles (Ag, Au)

There are numerous methods to prepare metal nanoparticles for EPEP or PEPST probes. Procedures for preparing gold and silver colloids include electroexplosion, electrodeposition, gas phase condensation, electrochemical methods, and solution-phase chemical methods. Although the methodologies for preparing homogeneous-sized spherical colloidal gold populations 2-40 nm in diameter are well known [N. R. Jana, L. Gearheart and C. J. Murphy, *Seeding growth for size control of* 5-40 *nm diameter gold nanoparticles. Langmuir* 17 (2001), pp. 6782-6786 the entire contents of which are incorporated herein by reference], and particles of this size are commercially available. An effective chemical reduction method for preparing populations of silver particles (with homogeneous optical scattering properties) or gold particles (with improved control of size and shape monodispersity) is based on the use of small-diameter uniform-sized gold particles as nucleation centers for the further growth of silver or gold layers.

A widely used approach involves citrate reduction of a gold salt to produce 12-20 nm size gold particles with a relatively narrow size distribution. One commonly used method for producing smaller gold particles is described in Brust, M.; Walker, M.; Bethell, D.; Schifrin. D. J.; Whyman, R. *Chem. Commun.* 1994, 801, the entire contents of which are incorporated herein by reference. This method is based on borohydride reduction of gold salt in the presence of an alkanethiol capping agent to produce 1-3 nm particles. Nanoparticle sizes can be controlled between 2 and 5 nm by varying the thiol concentration, [Hostetler, M. J.; Wingate, J. E; Zhong, C. J.; Harris, J. E.; Vachet, R. W.; Clark, M. R.; Londono, J. D.; Green, S. J; Stokes. J. J; Wignall, G. D.; Glish, G. L.; Porter. M. D.; Evans, N. D.; Murray, R. W. *Langmuir* 1998, 14, 17 the entire contents of which are incorporated herein by reference]. Phosphine-stabilized gold clusters have also been produced and subsequently converted to thiol-capped clusters by ligand exchange in order to improve their stability [Schmid, G.; Pfeil, R.; Boese, R.; Bandrmann, F.; Meyer, S.; Calls, G. H. M; van der Velden, J. W. A. *Chem. Ber.* 1981, 114, 3634; Warner, M. G.; Reed. S. M.; Hutchison, J. E. *Chem. Mater.* 2000, 12, 3316, the entire contents of which are incorporated herein by reference] and phosphine-stabilized monodispersed gold particles were prepared using a similar protocol to the Brust method [Weare, W. W; Reed, S. M.; Warner, M. G.; Hutchison, J. E. *J. Am. Chem. Soc.* 2000, 122, 12890, the entire contents of which are incorporated herein by reference]. See also: Ziyi Zhong, Benoit Male, Keith B. Luong, John H. T., *More Recent Progress in the Preparation of Au Nanostructures, Properties, and Applications, Analytical Letters* 2003. Vol. 36 Issue 15, p 3097-3118, the entire contents of which are incorporated herein by reference.

Fabrication of Nanoparticle of Metal Coated with Nanoshells of Dyes

The fabrication of metal nanoparticles coated with nanoshells of dye molecules can be performed using the method described in Akito Masuhara, Satoshi Ohhashi, Hitoshi Kasai; Shuji Okada. *FABRICATION AND OPTICAL PROPERTIES OF NANOCOMPLEXES COMPOSED OF METAL NANOPARTICLES AND ORGANIC DYES. Journal of Nonlinear Optical Physics & Materials* Vol. 13. Nos. 3 & 4 (2004) 587-592, the entire contents of which are incorporated herein by reference. Nanocomplexes composed of Ag or Au as a core and 3-carboxlymethyl-5-[2-(3-octadecyl-2-benzoselenazolinylidene)ethylidene]rhodanine (MCSe) or copper (II) phthalocyanine (CuPc) as a shell are prepared by the co-reprecipitation method. In the case of Ag-MCSe nanocomplexes, 0.5 mM acetone solution of MCSe are injected into 10 ml of Ag nanoparticle water dispersion, prepared by the reduction of $AgNO_3$ using $NaBH_4$: Au-MCSe nanocomplexes are also fabricated in a similar manner. A water dispersion of Au nanoparticles was prepared by the reduction of $HAuCl_4$ using sodium citrate. Subsequently, 2 M $NH_4OH$ (50 μl) was added and the mixture was thermally treated at 50° C. This amine treatment often stimulates the J-aggregate formation of MCSe.6 Ag—CuPc and Au—CuPc nanocomplexes were also fabricated in the same manner: 1 mM 1-methyl-2-pyrrolidinone (NMP) solution of CuPc (200 μl) was injected into a water dispersion (10 ml) of Ag or Au nanoparticles.

Preparation of Silver Nanoparticles

Silver (or gold) colloids were prepared according to the standard Lee-Meisel method: 200 mL of $10^{-3}$ M $AgNO_3$ aqueous solution was boiled under vigorous stirring, then 5 mL of 35-mM sodium citrate solution were added and the resulting mixture was kept boiling for 1 h. This procedure was reported to yield ~$10^{11}$ particles/mL of homogenously sized colloidal particles with a diameter of ~35-50 nm and an absorption maximum at 390 nm. The colloidal solutions were stored at 4° C. and protected from room light. Further dilutions of the colloidal solutions were carried out using distilled water.

Fabrication/Preparation of Metal Nanocaps

One approach has involved the use of nanospheres spin-coated on a solid support in order to produce and control the desired roughness. The nanostructured support is subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex nanospheres are commercially available in a wide variety of sizes. The shapes of these materials are very regular and their size can be selected for optimal enhancement. These materials comprise isolated dielectric nanospheres (30-nm diameter) coated with silver producing systems of half-nanoshells, referred to as nanocaps.

Fabrication of Gold Nanoshells

Gold nanoshells have been prepared using the method described in Hirsch L R, Stafford R J, Bankson J A, Sershen S R, Price R E, Hazle J D, Halas N J, West J L (2003) *Nanoshell-mediated near infrared thermal therapy of tumors under MR Guidance*. Proc Natl Acad Sci 100:13549-13554. This method uses a mechanism involving nucleation and then successive growth of gold nanoparticles around a silica dielectric core. Gold nanoparticles, the seed, prepared as described above using the Frens method, were used to grow the gold shell. Silica nanoparticles (100 nm) used for the core of the nanoshells were monodispersed in solution of 1% APTES in EtOH. The gold "seed" colloid synthesized using the Frens method were grown onto the surface of silica nanoparticles via molecular linkage of amine groups. The "seed" covers the aminated silica nanoparticle surface, first as a discontinuous gold metal layer gradually growing forming a continuous gold shell.

Commercial Applications

In the following commercial applications of the invention described here, the energy modulation agents 3 (e.g., luminescing particles or photon emitters) are provided and distributed into a medium 4 for deactivation or activation of agents in the medium to produce a physical, chemical, or biological change in the medium. In one embodiment, plasmonics agents as described above are added to the medium. The plasmonics agents can enhance both the applied initiation energy such that the enhanced initiation energy activates the at least one activatable agent which produces a change in the medium when activated and can enhance light converted by the energy modulation agents.

Examples of luminescing particles can include gold particles (such as for example the nanoparticles of gold described above), BaFBr:Eu particles, CdSe particles, $Y_2O_3$:$Eu^{3+}$ particles, and/or other known stimulated luminescent materials such as for example $ZnS:Mn^{2+}$; $ZnS:Mn^{2+}$, $Yb^{3+}$, $Y_2O_3:Eu^{3+}$; $BaFBr:Tb_{3+}$; and $YF_3:Tb^{3+}$.

In one embodiment of the invention described here, other potentially useful luminescing particles (or energy modulation agents) include carbon nanotubes as described for example by Wang et al. in "Electromagnetic excitation of nano-carbon in vacuum," in OPTICS EXPRESS, Vol. 13, No. 10, May 10, 2005, the entire contents of which are incorporated herein by reference. Such carbon nanotubes show both black body emission and discrete line-type emissions in the visible when exposed to microwave irradiation.

Other potentially useful luminescing particles for the invention described here include the chemiluminescent reactions/species described by Asian et al. in "Multicolor Microwave-Triggered Metal-Enhanced Chemiluminescence," in J. AM. CHEM. SOC. published on Web Sep. 23, 2006, the entire contents of which are incorporated herein by reference. These chemiluminescent reactions/species are formed with silver nanoparticles which enhance the chemiluminescent reactions when exposed to microwave radiation. Asian et al. utilized chemiluminescent species from commercial glow sticks where for example hydrogen peroxide oxidizes phenyl oxalate ester to a peroxyacid ester and phenol. The unstable peroxyacid ester decomposes to a peroxy compound and phenol, the process chemically inducing an electronic excited state responsible for the light emission. While these chemiluminescent species will have a limited lifetime, there use in curing applications for the invention described here is still viable where the cure process is a one-time occurrence, and the external microwave source accelerates the cure by accelerated visible light production.

The luminescent wavelength and/or efficiency of the luminescent particles often depend on the size of the particle. Particle sizes in the nanometer size range for the invention described here exhibit stronger luminescence in many cases, as described in U.S. Pat. Appl. Publ. No. 2007/0063154, whose entire contents are incorporated herein by reference. Further, in one embodiment of the invention described here, the luminescing particles can be combined with molecular complexes such as poly(ethylene glycol), vitamin B12, or DNA, which serves to mitigate against coagulation of the luminescing particles (especially the nanoparticles) and serves to make the luminescing particles biocompatible. More specifically, one recipe for the synthesis of CdSe nanocrystals is given here from U.S. Pat. Appl. Publ. No. 2007/0063154. Accordingly, citrate-stabilized CdSe nanocrystals suitable for the invention described here can be prepared according to the following procedure:

To 45 ml of water are added 0.05 g sodium citrate (Fluka) and 2 ml of $4\times10^{-2}$ M cadmium perchlorate (Aldrich). The pH is adjusted to 9.0 by 0.1 M NaOH (Alfa). The solution is bubbled with nitrogen for 10 minutes, and then 2 ml of $1\times10^{-2}$ M N,N-dimethylselenourea (Alfa) is added. The mixture is heated in a conventional 900-watt microwave oven for 50 seconds. In this recipe, the Cd:Se molar ratio is 4:1, which leads to CdSe nanoparticles with ~4.0 nm diameter; by increasing the Cd concentration it is possible to synthesize smaller CdSe nanoparticles.

Further, the luminescing particles for the invention described here can be coated with insulator materials such as for example silica which will reduce the likelihood of any chemical interaction between the luminescing particles and the medium. For biological applications of inorganic nanoparticles, one of the major limiting factors is their toxicity. Generally speaking, all semiconductor nanoparticles are more or less toxic. For biomedical applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable energy modulation agents which would seem the most biocompatible are zinc sulfide, ZnS:$Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$. $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers are also suitable as energy modulation agents: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

While many of the energy modulation agents of the invention are down conversion agents (i.e. where higher energy excitation produces lower energy emission). U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 including the ZnS as well as $Er^{3+}$ doped $BaTiO_3$ nanoparticles and $Yb^{3+}$ doped $CsMnCl_3$ are suitable in various embodiments of the invention.

Further materials specified for up conversion include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}MnTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\le1$, and $0<y\le1$). Complex compounds of the above-described semiconductors are also contemplated for use in the invention—e.g. $(M_{1-z}N_z)_{1-x}M_{n_x}A_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\le1$, $0<y\le1$, $0<z\le1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z\le1$, $o<q\le1$).

Indeed, some nanoparticles such as ZnS:$Tb^{3+}$, $Er^{3+}$; ZnS: $Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^+$ are known in the art to have two functions, capable of functioning for both down-conversion luminescence and upconversion luminescence.

To reduce the toxicity or to make these nanoparticles bio-inert or biocompatible, one embodiment of the invention described here coats these nanoparticles with silica. Silica is used as a coating material in a wide range of industrial colloid products from paints and magnetic fluids to high-quality paper coatings. Further, silica is both chemically and biologically inert and also is optically transparent. In the following recipe (from M. A. Correa-Duarte, M. Giesig, and L. M. Liz-Marzan, *Stabilization of CdS semiconductor nanoparticles against photodegradation by a silica coating procedure*, Chem. Phys. Lett., 1998, 286: 497, the entire contents of which is explicitly incorporated herein by reference in its entirety), citrate-stabilized CdTe:Mn 2+/$SiO_2$ nanocrystals suitable for the invention described here can be prepared with a silica coating:

(1) To a CdTe:Mn 2+ nanoparticle solution (50 ml), a freshly prepared aqueous solution of 3-(mercaptopropyl) trimethoxysilane (MPS) (0.5 ml, 1 mM) (Sigma) is added under vigorous stirring. The function of MPS is that its mercapto group can directly bond to the surface Cd sites of CdTe, while leaving the silane groups pointing toward solution from where silicate ions approach the particle surface; (2) Addition of 2 ml of sodium silicate (Alfa) solution at pH of 10.5 under vigorous stirring; (3) The resulting dispersion (pH~8.5) is allowed to stand for 5 days, so that silica slowly polymerizes onto the particle surface; and (4) Transfer of the dispersion to ethanol so that the excess dissolved silicate can precipitate out, increasing the silica shell thickness.

Alternatively, as shown in FIG. 3C and FIG. 3D, luminescing particles in encapsulated structures 10 could be placed in the vicinity of the medium. In one embodiment for the invention described here, luminescing particles are coated on the interior of quartz or glass tubes 9 and sealed. In another embodiment, luminescing particles could be coated on the surface of spheres or tubes, and afterwards encapsulated with silica (or other suitable passivation layer) using a vapor deposition or sputtering process or spin-on glass process of the solution process described above to make the encapsulation structures 10 which may be part of re-entrant structures extending from walls of a container (as in FIG. 3C) or which may be part of a fluidized bed structure (as in FIG. 3D). In another embodiment, the plasmonics agents are fixed to an outer surface of the glass tubes 9. External light applied to the tubes and scattered to the outer surfaces is enhanced at the plasmonics agents permitting more efficient treatment of the medium without necessarily having to use energy modulation agents.

In the either configuration, the medium to be treated would flow by the encapsulated structures 10, or flow along with encapsulated structures 6, and the separation distance between the encapsulated structures 6, 10 would be set a distance smaller than the UV penetration depth in the medium.

A suitable light source (such as one of the x-ray sources discussed above) can be used to stimulate the luminescing particles in the encapsulated structures 10. In one embodiment of the invention described here, the concentration of luminescing particles in the medium or the spacing between the encapsulated structures 10 is set such that luminescing particles are separated from each other in the medium by less than a UV depth of penetration into the medium. Higher concentrations are certainly usable and will generate higher UV fluxes should the energy source have enough intensity to "light" all the luminescing particles.

For a relatively unclouded aqueous medium, solar UV-B irradiance decreases to 1% after penetration into the water samples between 0.2 m and 1 m, whereas UV-A penetrates on the order of several meters. For such mediums, the concentration of luminescing particles is more determined by the time needed for the intended UV flux to produce deactivation or activation of an agent in the medium, rather than having to be set based on a concentration of luminescent particles where the medium itself does not occlude the UV stimulated emission from penetrating throughout the medium. The placement of the luminescent particles in the medium and in the vicinity of the medium is not restricted by the optical density of the medium.

Based on published data of an average of 5.2 spontaneous photons emitted from BaFBr:$Eu^{2+}$ for every keV of X-ray absorbed (M. Thoms, H. von Seggern, *Method for the determination of photostimulable defect center concentrations, production rates, and effective formation energies, J. Appl. Phys.* 1994, 75: 4658-4661, the entire contents of which is herein explicitly incorporated by reference in its entirety.), one expects that about 50 photons are emitted from a CdTe nanoparticle for each 50 keV X-ray absorbed.

Based on the results in U.S. Pat. Appl. Publ. No. 2007/0063154 for X-ray spectra of CdTe/BaFBr:$Eu^{2+}$ nanocomposites prepared using a concentration of 0.8 ml L-cysteine stabilized CdTe particle solution in 0.2 g BaFBr:$Eu^{2+}$ phosphor. As the X-ray irradiation time increases, the X-ray luminescence intensity of $Eu^{2+}$ at 390 nm increases in intensity. This phenomenon has been discussed in W. Chen, S. P. Wang, S. Westcott, J. Zhang, A. G. Joly, and D. E. McCready, *Structure and luminescence of BaFBr:$Eu^{2+}$ and BaFBr:$Eu^{2}$, $Tb^{3+}$ phosphors and thin films*, J. Appl. Phys. 2005, 97: 083506, the entire contents of these references are herein incorporated by reference in their entirety.

Hence, in one embodiment of the invention, a minimum baseline concentration of about $10^9$ nanoparticles per $cm^3$ for 200 nm diameter particles is expected to be sufficient for UV emission to produce a change in the medium. The invention is not limited to this concentration range, but rather this range is given as an illustrative example. Indeed, higher concentrations will increase the UV emission per unit time and provide faster reactions, which in general would be considered more useful in industrial applications where product throughput is a concern.

Sterilization and Cold Pasteurization of Fluids

Table 1 included below shows appropriate intensities for germicidal destruction.

TABLE 1

| Germicidal energies needed to destroy | |
|---|---|
| Approximate intensity ($\mu W/cm^2$) required for 99% destruction of microorganisms: | |
| Bacteria | 10 400 |
| Protozoa (single celled organism) | 105 000 |
| Paramecium (slipper shaped protozoa) | 200 000 |
| Chlorella ( unicellular fresh-water alga) | 13 000 |
| Flagellate(protozoan or alga with flagella) | 22 000 |
| Sporozoan (parasitic protozoans) | 100 000 |
| Virus | 8 000 |

Accordingly, the energy modulation agents (or luminescing particles) of the invention (as discussed above with regard to FIGS. 3B and 3C) can be provided on the interior of sealed quartz or glass tubes or can be provided coated on the surface of spheres or tubes, and further encapsulated with a silica or passivation layer. Plasmonics agents can be formed with the energy modulation agents. In either configuration for the invention described here, a medium could flow by the encapsulated structures 6, 10 with a separation distance between the encapsulated structures or the quartz or glass tubes being made smaller than the UV penetration depth.

For example, it is known that ultraviolet (UV) with a wavelength of 254 nm tends to inactivate most types of microorganisms. Most juices are opaque to UV due to the high-suspended solids in them and hence the conventional UV treatment, usually used for water treatment, cannot be used for treating juices. In order to make the process efficient, a thin film reactor constructed from glass has been used with the juice flowing along the inner surface of a vertical glass tube as a thin film. See "Ultraviolet Treatment of Orange Juice" by Tran et al. published in Innovative Food Science & Emerging Technologies (Volume 5, Issue 4, December 2004, Pages 495-502), the entire contents of which are incorporated herein by reference. Tran et al. reported therein decimal reduction doses required for the reconstitute orange juices (OJ; 10.5° Brix) were 87±7 and 119=17 mJ/cm$^2$ for the standard aerobic plate count (APC) and yeast and moulds, respectively. In that article, the shelf life of fresh squeezed orange juice was extended to 5 days with a limited exposure of UV (73.8 mJ/cm$^2$). The effect of UV on the concentration of Vitamin C was investigated using both HPLC and titration methods of measurements. The degradation of Vitamin C was 17% under high UV exposure of 100 mJ/cm$^2$, which was similar to that usually found in thermal sterilization. Enzyme pectin methylesterase (PME) activity, which is the major cause of cloud loss of juices, was also measured. The energy required for UV treatment of orange juice (2.0 kW h/m$^3$) was much smaller than that required in thermal treatment (82 kW h/m$^3$). The color and pH of the juice were not significantly influenced by the treatment.

The invention described herein offers advantages over this approach in that the energy modulation agents can be placed inside fixtures such as quartz or glass (encapsulation structures 8) within the orange juice (or other fluid medium) and irradiated with x-rays (or other penetrating radiation) through for example a plastic or aluminum container 9 to activate the energy modulation agents 3 and 6 in the orange juice. As such, the expense and fragility of a thin film reactor constructed from glass of other similar structure is avoided.

While discussed with regard to orange juice, any other medium to be sterilized including food products, medical products and cosmetic products could be treated using the technique of the invention described herein.

Sterilization of Medical and Pharmaceutical Articles

As noted above, medical bottle caps need to be sterilized between the base cap material and the seal material which contacts to the base of the medical bottle. Steam autoclaves are insufficient for this purpose as once glued, the steam is unable to penetrate into the glue seam.

Gamma irradiation has been used conventionally to sterilize medical bottle caps and other medical, pharmaceutical, and cosmetic articles such as surgical disposables (e.g., surgical bandages, dressings, gauge pads, nappies, delivery kits, and etc.), metallic products (e.g., surgical blades, implants, aluminum caps, containers, etc.), and plastic and rubber Items (e.g., petri-dish, centrifuge tube, blood collection sets, scalp vein sets, shunt valves, rubber gloves, contraceptive devices, gowns, wraps covers, sheets, etc.). The invention would be applicable for the sterilization of any "interior" surfaces of these and other products.

In one embodiment of the invention described herein, UV luminescent particles would be included in an adhesive layer when the seal material is applied to the bottle cap. X-ray irradiation would then be capable of curing the adhesive (if for example the adhesive were a photosensitive adhesive as discussed below in greater detail) and would produce within the adhesive medium UV radiation for direct sterilization or for the production of singlet oxygen or ozone for biological germicide. Additionally, plasmonics agents can be included to enhance the effect of the incident radiation or the internally generated radiation.

While illustrated here with regard to medical bottle caps, other adhesively constructed devices could benefit from these procedures in which the adhesive medium is cured and/or sterilized during activation of energy modulation agents 3 and 6.

Sterilization of Blood Products

U.S. Pat. No. 6,087,141 (the entire contents of which are incorporated herein by reference) describes an ultraviolet light actived psoralen process for sterilization of blood transfusion products. Here, the invention can be applied for example in the equipment shown in FIGS. 3C and 3D for the treatment of or the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine. 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. These photoactivatable agents are introduced into the blood product (or a patient's blood stream). A penetrating energy is applied to the blood product (or to the patient). The energy modulation agents (either included in the blood product) or in encapsulated structures 10 generate secondary light such as UV light which activates the photoactivatable agents in the blood products.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof. The incorporated by reference U.S. Ser. No. 11/935,655 describes more specifically that photoactivatable agents may be stimulated by an energy source such as irradiation, resonance energy transfer, exciton migration electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the present invention administers a photoactivatable agent to a patient, stimulates the photoactivatable agent to induce cell damage, and generates an auto Vaccine effect. In one further preferred embodiment, the photoactivatable agent is stimulated via a resonance energy transfer.

Waste Water Detoxification

Photocatalysis has also been used as tertiary treatment for wastewater to comply with the regulatory discharge limits and to oxidize persistent compounds that have not been oxidized in the biological treatment. Photocatalysis has being applied to the elimination of several pollutants (e.g., alkanes, alkenes, phenols, aromatics, pesticides) with great success. In many cases, total mineralization of the organic compounds has been observed. Several photocatalysts, such as CdS, $Fe_2O_3$, ZnO, $WO_3$, and ZnS, have been studied, but the best results have been achieved with $TiO_2$ $P_{25}$. These photocatalyst are usable for the invention described here.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

It is known that photocatalysis can be used for waste water reduction remediation. U.S. Pat. No. 5,118,422 (the entire contents of which are incorporated herein by reference) to Cooper et al. describe an ultraviolet driven photocatalytic post-treatment technique for purifying a water feedstock containing an oxidizable contaminant compound. In this work, the water feedstock was mixed with photocatalytic semiconductor particles (e.g., $TiO_2$, ZnO, CdS, CdSe, $SnO_2$, $SrTiO_3$, $WO_3$, $Fe_2O_3$, and $Ta_2O_5$ particles) having a particle size in the range of about 0.01 to about 1.0 micron and in an amount of between about 0.01% and about 0.2% by weight of the water. The water including the semiconductor mixture is exposed to band-gap photons for a time sufficient to effect an oxidation of the oxidizable contaminant to purify the water. Crossflow membrane filtration was used to separate the purified water from the semiconductor particles. Cooper et al. show that the organic impurity carbon content of simulated reclamation waters at nominal 40 PPM level were reduced to parts per billion using a recirculation batch reactor.

Cooper et al. identified that one important aspect of the photocatalytic process is the adsorption of the organic molecules onto the extremely large surface area presented by the finely divided powders dispersed in the water. Cooper et al. further indicated that, in photoelectrochemical applications, advantage is taken of the fact that the solid phase (a metal oxide semiconductor) is also photo-active and that the generated charge carriers are directly involved in the organic oxidation. The adsorption of the band-gap photon by the semiconductor particle results in the formation of an electron ($e^-$)/hole($h^+$) pair. Cooper et al. explain that the electrons generated in the conduction band react with solution oxygen forming the dioxygen anion ($O_2$) species which subsequently undergo further reactions resulting in the production of the powerfully oxidizing hydroxyl radical species, OH. These powerful oxidants are known to oxidize organic compounds by themselves. Additionally, Cooper et al. explain that the strongly oxidizing holes generated in the valence band have sufficient energy to oxidize all organic bonds.

In the reactor of Cooper et al., turbulence is necessary in order to ensure that the waste water contaminants and the photocatalytic titania particles are exposed to the UV light. Cooper et al. explain that the most basic considerations of photocatalyst light adsorption and its relationship to convective mixing. For a 0.1 wt % photocatalyst loading, experiments have shown that 90% of the light is absorbed within 0.08 cm. This is primarily due to the large UV absorption coefficient of the photocatalyst and therefore, most of the photoelectrochemistry occurs within this illuminated region. By operating the reactor of Cooper et al. with a Reynolds number (Re) of 4000, a significant portion of the photoactive region is ensured of being within the well mixed turbulent zone.

Santos et al. have reported in "Photocatalysis as a tertiary treatment for petroleum refinery wastewaters" published in Braz. J. Chem. Eng. vol. 23, No. 4, 2006 (the entire contents of which are incorporated herein by reference), photocatalysis for tertiary treatment for petroleum refinery wastewaters which satisfactorily reduced the amount of pollutants to the level of the regulatory discharge limits and oxidized persistent compounds that had not been oxidized in the biological treatment. The treatment sequence used by the refinery (REDUC/PETROBRAS, a Brazilian oil refinery) is oil/water separation followed by a biological treatment. Although the process efficiency in terms of biological oxygen demand (BOD) removal is high, a residual and persistent COD and a phenol content remains. The refining capacity of the refinery is 41,000 $m^3$/day, generating 1,100 $m^3$/h of wastewater, which are discharged directly into the Guanabara Bay (Rio de Janeiro). Treating the residual and persistent COD remains a priority.

Santos et al. conducted a first set of experiments carried out in an open 250 mL reactor containing 60 mL of wastewater. In the second set of experiments, a Pyrex® annular reactor containing 550 mL of wastewater was used (De Paoli and Rodrigues, 1978), as shown in FIG. 1. The reaction mixtures inside the reactors were maintained in suspension by magnetic stirring. In all experiments, air was continuously bubbled through the suspensions. A 250 W Phillips HPL-N medium pressure mercury vapor lamp (with its outer bulb removed) was used as the UV-light source (radiant flux of 108 $J \cdot m^{-2} \cdot s^{-1}$ at 8>254 nm). In one set of experiments, the lamp was positioned above the surface of the liquid at a fixed height (12 cm). In the second set, the lamp was inserted into the well. All experiments by Santos et al. were performed at 25±1° C. The catalyst concentration ranged from 0.5 to 5.5 g $L^{-1}$ and the initial pH ranged from 3.5 to 9.

In the invention described herein, luminescing particles or other energy modulation agents would be placed inside quartz or glass fixtures within the waste water or would be placed on silica encapsulated structures within the waste water which, like the photocatalytic $TiO_2$, could be entrained in the waste water during the irradiation. Additionally, the plasmonics agents can be included to enhance the effect of the incident radiation or the internally generated radiation.

Upon irradiation with x-rays (or other penetrating radiation) through for example a plastic or aluminum container, activation of the luminescing particles (i.e., energy modulation agents) would generate UV light in nearby presence of the photocatalytic agent. In other words for the invention described herein, the luminescent particles or other energy modulation agents are mixed along with the photocatalytic semiconductor particles in the waste water fluid stream, and the exterior activation energy source penetrates the container (e.g., a plastic or aluminum container) and irradiates the bulk of the waste water, producing UV light throughout the waste water which in turn drives the photocatalytic reactions. In one embodiment, the plasmonics agents are complexed with the luminescent particles or other energy modulation agents prior to being added to the fluid stream.

As such, the invention described herein offers a number to advantages over that described above, including the elimination of expensive holding tanks for the waste water, the avoidance of having to pump the wastewater at higher pressures or flowrates to produce sufficient turbulence, and the generation of UV light throughout the wastewater to thereby provide faster bulk processing of the waste water.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

Workers have found that UV irradiation could realize an effective graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photo-grafting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of luminescing particles or other energy modulation agents in dispersion in the fluid medium being used for photostimulation. Additionally, the plasmonics agents can be included to enhance the effect of the incident radiation or the internally generated radiation. In one embodiment, the plasmonics agents are complexed with the luminescent particles or other energy modulation agents prior to being added to the fluid medium.

Upon irradiation with x-rays (or other penetrating radiation) through for example a plastic or aluminum container, activation of the luminescing particles (i.e., energy modulation agents) would generate UV light throughout the volume of the medium (eliminating any shadowing effects) and permitting batch or bulk type processing to occur in parallel throughout the container.

In other examples, the interior generation of light inside a bulk medium may serve to stimulate a chemical or biological process either by direct interaction of the light with activatable agents in the medium or the indirect generation of heat which the invention described here by way of dispersed energy modulation agents would provide a controlled and uniform way to heat a vat of material in a biological or chemical process.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Wanting to stop a fermentation is all good in and of itself. But unfortunately, there is really no practical way to successfully stop a fermentation dead in its tracks. Additives such as sulphite and sorbate can be added to stabilize a fermented product and stop additional fermentation. Many winemakers will turn to sulfites such as that found in Sodium Bisulfite or Campden tablets for the answer. But, these two items are not capable of reliably killing enough of the yeast to guarantee a complete stop of the activity—at least not at normal doses that leave the wine still drinkable.

Once the bulk of the sulfites from either of these ingredients dissipate from the wine into the air—as sulfites do—there is a very strong chance that the remaining few live yeast cells will start multiplying and fermenting again if given enough time. This usually happens at a most inconvenient time, like after the wine has been bottled and stowed away.

Potassium sorbate is another ingredient that many winemakers consider when trying to stop a wine from fermenting any further. There is a lot of misunderstanding surrounding this product. It is typically called for by home wine making books when sweetening a wine. This is a situation where the fermentation has already completed and is ready for bottling. One adds the potassium sorbate along with the sugar that is added for sweetening.

The potassium sorbate stops the yeast from fermenting the newly added sugar. So, many winemakers assume potassium sorbate can stop an active fermentation as well, but, potassium sorbate does not kill the yeast at all, but rather it makes the yeast sterile. In other words, it impairs the yeast's ability to reproduce itself. But, it does not hinder the yeast's ability to ferment sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above for liquid pasteurization could be used for the invention described here. For non-liquid products, energy modulation agents with little and preferably no toxicity (e.g. Fe oxides or titanium oxides) could be added. Here, the concentration of these additives would likely be limited by any unexpected changes in taste.

Photoactivated Cross-Linking and Curing of Polymers

In this application, luminescing particles (or energy modulation agents) are provided and distributed into an uncured polymer based medium for the activation of photosensitive agents in the medium to promote cross-linking and curing of the polymer based medium. Additionally, the plasmonics agents can be included to enhance the effect of the incident radiation or the internally generated radiation. In one embodiment, the plasmonics agents are complexed with the luminescent particles or other energy modulation agents prior to being added to the polymer.

As noted above, for adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the luminescing particles (or energy modulation agents) are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with for example carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silicone resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinvlphenyl)dimethylsilyl, (vinylbenzyl)dimethylsilyl, and (vinylphenethyl)dimethylsilyl.

The photoinitiator component of the invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4, 6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis (.eta..sup.5-2,4-cyclopentadien-1-yl)-bis[2,6-difluoro-3-(1H-pyrrol-1-yl)phenyl]titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 um. Other Q-CEL products are shown below in tabular form. Another commercially available hollow glass microsphere is sold by Kish under the trade name SPHERI-CEL. SPHEREICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCH-LITE tradename.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescing particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are luminescing particles. These luminescing particle containing compositions can then be applied to surfaces of objects to be fixed together or to surfaces where a hard coating is desired or cast in a curable form for the production of molded objects. The luminescing particles in these compositions upon activation will produce radiant light for photoactivated cure of the luminescing particle containing polymer composition. The density of luminescing particles in these compositions will depend on the "light transparency" of the luminescing particle containing composition. Where these compositions contain a significant amount of the inorganic filler as discussed above, the concentration of luminescing particles can be reduced for example as compared to a composition with a black color pigment where the light transparency will be significantly reduced.

One advantage of the invention described here as seen from this example is that now color pigments can be included in the light curable resins without significant compromise in the cured product performance. These color pigments may include one or more colored pigments well known to those of ordinary skill in the art. Such pigments are generally metal oxides and include, but are not limited to, titanium dioxide, iron oxides, organic complexes, mica, talc and quartz. One pigment may be used, or a combination of two or more pigments may be utilized. Different colors can be obtained by choosing proper pigments and combining them in a similar fashion as set forth in the following examples with the necessary adjustments, common in the paint industry, being made. Accordingly, in one embodiment of the invention, these color pigments including carbon black may also be included as an optically opaque materials to limit the propagation of internally generated light from the point of generation.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular. Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the luminescing particles (or energy modulation agents) described above are added to these Bach et al. compositions, optionally including in one embodiment various color pigments. Due to the fact that the exterior energy source penetrates throughout the entirety of the Bach et al. compositions, thicker surface coatings can be realized. Further, the coatings can be applied to intricate surfaces having for example been prepared with recesses or protrusions. Curing with the recesses and around the protrusions without being limited by conventional UV shading will likely provide enhanced adherence of the surface coating to the work piece.

Moreover, in one embodiment of the invention, an external energy source of the initiation energy can be directed to a structural element in which a gap (or crack) therein was filled with an uncured radiation-curable medium (such as those described above). The internally generated light will cure the uncured radiation-curable medium in the gap (or crack) thereby providing a repair to the structure being irradiated.

Presently, there is available commercial epoxy systems which utilize epoxy resin injection for the structural restoration of concrete. Epoxy injection is very often the only alternative to complete replacement of a structure. It therefore results in great cost savings. Besides filling the cracks, epoxy injection is known to protect rebar in the concrete and to stop water leakage. Commercially, the epoxy injection resin provides a system for welding cracks which restores the original strength and loading originally designed into the concrete. Typically, low viscosity resins are pressure injected into the cracks. Often holes are drilled near or into the cracks to provide a conduit for pumping the resin into the cracks.

It, however, takes time for the resin to penetrate into the thinner, even hair line cracks. Unfortunately, time is limited in the present commercial systems due to the fact that the resins are premixed with hardeners whose time to cure sets an upper limit for how long the low viscosity resin can flow into the cracks. Furthermore, time to complete repair is an issue in many industrial repairs as the hardener is usually present in a concentration high enough to have the resin set for example in twenty four (24) hours. Moreover, with traditional resin methods, it is not possible to induce curing at specific regions of interest since all the areas of the resin will be cured The present invention offers a number of advantages. Firstly, the resin of the present invention will be a photactivated resin which will not substantially cure until the x-ray source generates internal light to activate the photoinitiators. This provides more flexibility in pumping and waiting for complete crack fill. Secondly, once the photoactivatable resin is in place, its cure is then activated, and the cure occurs at a rate not controlled by the convention hardening reaction. Thirdly, the x-ray penetration through the concrete and the crack region will provide a more uniform mechanism for cure of the resins, with the deep cracks being as likely to fully cure as the narrow cracks which may extend deeper into the material. Furthermore, the present invention allows the possibility to cure only the specific areas of interest, i.e., where the X-ray is irradiated.

In another embodiment of the present invention, the external energy source can be a directed or focused beam of the initiation energy which cures an uncured radiation-curable medium to produce a patterned element. In this embodiment, the structure holding or at least partially enclosing the uncured radiation-curable medium can be a structure opaque to visible light. In this manner, the uncured radiation-curable medium (which normally would be photoactivated upon exposure to ambient light) can be transported without premature curing. In this embodiment, the curing would be activated for example by directed one or several focused beams of x-rays whose overlap generates regions in the structure holding or at least partially enclosing the uncured radiation-curable medium where the generated UV or visible light from the energy modulation agents in the medium would be of sufficient intensity to activate the photoinitiators. In this manner, precise three-dimensional and two-dimensional patterning can be performed. In a similar embodiment, upconverting energy modulation agents could be used when the structure is transmissive of for example infrared or microwave frequencies. The initiation energy from, for example IR lasers, would be directed and focused into the structure holding or at least partially enclosing the uncured radiation-curable medium.

As an example in another embodiment, a patterned element such as a device (such as plug to close a specific internal hole or path ways) can be fabricated (e.g., cured) inside structures (e.g., building materials, man-made or natural underground storage tank, internal organs of human body, etc) using energy excitation (e.g., X ray) from the outside of such structures. Another application of this technique would involve the fabrication of orthopedic structures inside the body, where the curable resin was introduced locally at the point of the orthopedic structure to be formed and a directed or focused x-ray beam cured the structure.

Accordingly, in another embodiment of the present invention, there is provided a method (and associated system) for producing a patterned element inside a structure. The method places inside the structure a radiation curable medium including at least one of a plasmonics agent and an energy modulation agent. The energy modulation agent is configured to emit light into the medium upon interaction with an initiation energy. The method applies to the medium the initiation energy from a directed or focused energy source. The applied initiation energy interacts with the plasmonics agent or the energy modulation agent to generate light at local regions inside the structure to cure locally the radiation curable medium.

As noted above, this method can form for the patterned element a plug to close a hole or pathway in the structure such as for example holes or pathways in a building material, a man-made or natural underground storage tank, or an internal organ in a human or animal body. The method can form for the patterned element a prosthetic device at a local point in the body of a human or animal.

The method can further localize the curing by placing in the radiation curable medium optically dense materials (such as the color pigments discussed above) to reduce propagation of the generated light from the point of generation.

Computer-Assisted Control

In one embodiment of the invention, there is provided a computer implemented system for designing and selecting suitable combinations of initiation energy source, energy modulation agent, and activatable agent. For example, the computer system 5 can include a central processing unit (CPU) having a storage medium on which is provided: a database of excitable compounds, a first computation module for a photoactivatable agent or energy transfer agent, and a second computation module predicting the requisite energy flux needed to sufficiently activate the or energy transfer agent or photoactivatable agent.

FIG. 4 illustrates a computer system 1201 for implementing various embodiments of the invention. The computer system 1201 may be used as the computer system 5 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203. The pointing device, for example, may be a mouse, a trackball, or a pointing stick for communicating direction information and command selections to the processor 1203 and for controlling cursor movement on the display. In addition, a printer may provide printed listings of data stored and/or generated by the computer system 1201.

The computer system 1201 performs a portion or all of the processing steps of the invention (such as for example those described in relation to FIG. 5) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The exemplary energy spectrum previously noted in FIG. 1 may also be used in this computer-implemented system.

The reagents and chemicals useful for methods and systems of the invention may be packaged in kits to facilitate application of the invention. In one exemplary embodiment, a kit would comprise at least one activatable agent capable of producing a predetermined cellular change, at least one energy modulation agent capable of activating the at least one activatable agent when energized, at least one plasmonics agent that can enhance applied initiation energy such that the enhanced initiation energy activates the at least one activatable agent which produces a change in the medium when activated, and containers suitable for storing the agents in stable form, and further comprising instructions for administering the at least one activatable agent and at least one energy modulation agent to a medium, and for applying an initiation energy from an initiation energy source to activate the activatable agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

System Implementation

In one embodiment of the invention, there is provided a first system for producing a change in a medium disposed in an artificial container. The first system includes a mechanism configured to supply in the medium at least one of a plasmonics agent and an activatable agent. The plasmonics agent enhances or modifies energy in a vicinity of itself. In one example, the plasmonics agent enhances or modifies the applied initiation energy such that the enhanced initiation energy produces directly or indirectly the change in the medium. The system includes an initiation energy source configured to apply an initiation energy through the artificial container to the medium to activate the at least one activatable agent in the medium.

In one embodiment, the energy modulation agent converts the applied initiation energy and produces light at an energy different from the applied initiation energy. The plasmonics agent can enhance the light from the at least one energy modulation agent. In one embodiment, the applied initiation energy source is an external initiation energy source. In one embodiment, the applied initiation energy source is a source that is at least partially in a container holding the medium.

The medium in one embodiment is substantially transparent to the initiation energy. For example, if the medium is a liquid or fluid food product such as orange juice which has a substantial amount of suspended solids, then UV light for example as described above and even visible light will be substantially absorbed and/or scattered by the orange juice medium. Furthermore, microwave energy will likewise be absorbed by this medium. However, an initiation energy source such as an X-ray source will essentially transmit entirely through for example an orange juice medium. The effect is the medium can now be totally illuminated with the external initiation energy source.

Other sources and tuned to specific wavelengths may also be used as the initiation energy source. These sources would take advantage of an "optical window" in the medium where for example a particular wavelength of light would not be absorbed. Water selectively scatters and absorbs certain wavelengths of visible light. The long wavelengths of the light spectrum—red, yellow, and orange—can penetrate to approximately 15, 30, and 50 meters (49, 98, and 164 feet), respectively, while the short wavelengths of the light spectrum—violet, blue and green—can penetrate further. Thus, for many aqueous based systems, non-high energy X-ray sources may not be needed. In those situations, energy modulation agents and plasmonics agents would be added whose interaction with the incident light would produce for example photoactivation of catalysts in the aqueous medium. Light produced from the energy modulation agent can also be enhanced by the plasmonics agents in the medium.

Accordingly, depending on the medium and the energy modulation agent and the activatable agent, the initiation energy source can include at least one of an X-ray source, a gamma ray source, an electron beam source, an UV radiation source, a visible and infrared source, a microwave source, or a radio wave source. The initiation energy source can then be an energy source emitting one of electromagnetic energy, acoustic energy, or thermal energy. The initiation energy source can then be an energy source emitting a wavelength whose depth of penetration penetrates throughout the medium. The initiation energy in one embodiment may be scattered or absorbed in the medium, but the plasmonics agents make useful the remnant light. The medium to be effected can be a medium to be fermented, sterilized, or cold pasteurized. The medium to be effected can include bacteria, viruses, yeasts, and fungi.

The activatable agents can be photoactivatable agents such as the photocages (described elsewhere) such that upon exposure to the initiation energy source, the photocage disassociates rendering an active agent available. The activatable agents can include agents such as psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. The activatable agents can include photocatalysts such as $TiO_2$, ZnO, CdS, CdSe, $SnO_2$, $SrTiO_3$, $WO_3$, $Fe_2O_3$, and $Ta_2O_5$ particles.

The first system can include a mechanism configured to provide in the medium at least one energy modulation agent which converts the initiation energy to an activation energy for activation of the activatable agent(s). The energy modulation agent(s) can be a photon emitter such a phosphorescent compounds, chemiluminescent compounds, and bioluminescent compounds. The energy modulation agent(s) can be up conversion or down conversion agents. The energy modulation agent(s) can be luminescent particles which emit light upon exposure to said initiation energy. The energy modulation agent(s) can be nanotubes, nanoparticles, chemiluminiscent particles, and bioluminescent particles, and mixtures thereof. The luminescent particles can be nanoparticles of semiconducting or metallic materials. The luminescent particles can be chemiluminescent particles which show enhanced chemiluminescence upon exposure to microwaves.

The first system can include a mechanism configured to provide in the medium plasmonics-agents including metal nanostructures such as for example nanospheres, nanorods, nanocubes, nanopyramids, nanoshells, multi-layer nanoshells, and combinations thereof. The form and structure of these plasmonics-agents can include the probe structures detailed above.

Depending on the initiation energy source, the system can include a container for the medium that is permeable to the applied initiation energy. For example, for an X-ray source, the container can be made of aluminum, quartz, glass, or plastic. For a microwave source, the container can be made of quartz, glass, or plastic. Furthermore, the container can be a container which receives and transmits the initiation energy to fluid products to pasteurize the fluid products, or can be a container which receives and transmits the initiation energy to fluid products to remediate contaminants in the fluid products.

In another embodiment of the invention, there is provided a second system for curing a radiation-curable medium. The second system includes a mechanism configured to supply an uncured radiation-curable medium including at least one plasmonics agent and at least one activatable agent which produces a change in the radiation-curable medium when activated, and further includes an applied initiation energy source configured to apply initiation energy to a composition including the uncured radiation-curable medium, the plasmonics agent, and the energy modulation agent. The energy modulation agent as described above absorbs the initiation energy and converts the initiation energy to an activation energy capable of curing the uncured medium (i.e., promoting polymerization of polymers in the uncured medium). The plasmonics agent enhances the applied initiation energy such that the enhanced initiation energy directly or indirectly cures the medium by polymerization of polymers in the medium. For example, the plasmonics agent can enhance the activation energy light such that enhanced light activates the at least one photoactivatable agent to polymerize polymers in the medium. In another example, activation of the energy modulation gaent produces a light which activates the at least one photoactivatable agent to polymerize polymers in the medium.

The second system has attributes similar to the first system described above and can further permit the at least one activatable agent to include a photoinitiator such as one of benzoin, substituted benzoins, alkyl ester substituted benzoins, Michler's ketone, dialkoxyacetophenones, diethoxyacetophenone, benzophenone, substituted benzophenones, acetophenone, substituted acetophenones, xanthone, substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators, non-fluorene-carboxylic acid peroxyesters and mixtures thereof.

The second system can also include a mechanism configured to provide in the medium plasmonics-agents including metal nanostructures such as for example nanospheres, nanorods, nanocubes, nanopyramids, nanoshells, multi-layer nanoshells, and combinations thereof. The form and structure of these plasmonics-agents can include the probe structures detailed above.

The second system can include a container for the uncured radiation-curable medium that is permeable to the applied initiation energy. The container can be configured to contain the uncured radiation-curable medium or to hold a mold of the uncured radiation-curable medium. The container as before can be an aluminum container, a quartz container, a glass container, or a plastic container, depending on the applied initiation energy.

In one embodiment, an energy source (e.g., an external energy source) is configured to irradiate the uncured radiation-curable medium in a joint region (or regions) adhering one region of a utensil to another region of the utensil. In another embodiment, the energy source is configured to irradiate the joint regions and thereby induce sterilization of the joint regions due to the production of internal UV light inside the joint regions. In another embodiment, the energy source is configured to irradiate a surface coating. In another embodiment, the energy source is configured to irradiate a mold of the radiation-curable medium.

The radiation-curable medium in the surface coating or in the mold or in other medium can include color pigments to add color to a finished cured product. The radiation-curable medium in the surface coating or in the mold or in another medium can include fumed silica to promote strength and enhance distribution of the internally generated light. The radiation-curable medium in the surface coating or in the mold or in another medium can include a moisture cure promoter to supplement the cure.

The second system provides one mechanism for production of novel radiation-cured articles, which include a radiation-cured medium, at least one plasmonics agent, and at least one energy modulation agent distributed throughout the medium. The energy modulation agent being a substance which is capable of converting an applied energy to light capable of producing a cure for the radiation-cured medium. The plasmonics agent enhances the applied initiation energy such that the enhanced initiation energy activates the energy modulation agents. Light produced from the energy modulation agent can also be enhanced by the plasmonics agents in the medium. The article can include luminescent particles such as for example nanotubes, nanoparticles, chemiluminiscent particles, and bioluminescent particles, and mixtures thereof. The article can include nanoparticles of semiconducting or metallic materials. The article can include chemiluminescent particles. The article can include color pigments or fumed silica. The article can include plasmonics-agents including metal nanostructures such as for example nanospheres, nanorods, nanocubes, nanopyramids, nanoshells, multi-layer nanoshells, and combinations thereof. The form and structure of these plasmonics-agents can include the probe structures detailed above.

In another embodiment of the invention, there is provided a third system for producing a change in a medium disposed in an artificial container. The third system includes a mechanism configured to provide to the medium 1) an activatable agent and 2) at least one of a plasmonics agent and an energy modulation agent. The energy modulation agent converts an initiation energy to an activation energy which then activates the at least one activatable agent. The third system further includes an applied initiation energy source configured to apply the initiation energy through the artificial container to activate the at least one activatable agent in the medium. The plasmonics agent enhances or modifies an energy in a vicinity of itself. In one example, the plasmonics agent enhances or modifies the applied initiation energy such that the enhanced initiation energy produces directly or indirectly the change in the medium.

The third system has similar attributes to the first and second systems described above, and further includes encapsulated structures including at least one of the energy modulation agent and the plasmonics agent. The encapsulated structures can include nanoparticles of the energy modulation agent encapsulated with a passivation layer or can include sealed quartz or glass tubes having the energy modulation agent inside. The encapsulated structures can include sealed tubes having the plasmonics agent disposed on an outside of the sealed tube (which may or may not be exposed directly to the medium).

In another embodiment of the invention, there is provided a fourth system for producing a photo-stimulated change in a medium disposed in an artificial container. The fourth system includes a mechanism configured to provide in the medium at least one of a plasmonics agent and an energy modulation agent. The energy modulation agent converts an initiation energy to an activation energy which then produces the photo-stimulated change. The fourth system further includes an initiation energy source configured to apply the initiation energy to the medium to activate the at least one energy modulation agent in the medium. The plasmonics agent enhances or modifies an energy in a vicinity of itself. In one example, the plasmonics agent enhances or modifies the applied initiation energy such that the enhanced initiation energy produces directly or indirectly the change in the medium. The system can include encapsulated structures including therein the energy modulation agent. The encapsulated structures can include nanoparticles of the energy modulation agent encapsulated with a passivation layer. The encapsulated structures can include sealed tubes having the plasmonics agent disposed on an outside of the sealed tube (which may or may not be exposed directly to the medium).

The fourth system can include a container which receives and transmits the initiation energy to products within the medium. The products can include plastics, where the activation energy alters the surface structure of the plastics. The products can include polylactic acid (PLA) plastics and polyhydroxyalkanoates (PHA) plastics. In this embodiment, the activation energy can photo-graft a molecular species onto a surface of the plastics.

Sterilization Methods and System Components

Optical techniques have been often used in sterilization procedures to render unwanted or harmful waterborne microorganisms incapable of reproducing using ultraviolet light (specifically the spectral area of UV-C, 200 to 280 nm range). Ultraviolet light in the UV-C is considered the most lethal range as a germicidal disinfectant (capable of altering a living microorganism's DNA, and keeping the microorganism from reproducing). UV-C, with 264 nanometers being the peak germicidal wavelength, is known as the germicidal spectrum. Although the UV-C method is simple and effective, it is not particularly effective in samples (gas, liquids, particulates) enclosed on containers which do not transmit UV light. The present invention provides techniques and systems that can use externally applied radiation such as X-ray for sterilization. While illustrated below with respect to X-ray irradiation, and as discussed above, other suitable forms of energy could be used provided the containers and medium to be sterilized was sufficiently transparent for the medium to be thoroughly irradiated. Examples of alternative sources and materials for upconverting luminescence to higher energies have been discussed above.

FIGS. 27-44 show various embodiments of sterilization systems and probes that can be used with X ray excitation. These systems are applicable in a number of the applications discussed above and as well as in other sterilization areas. The systems could thus be used in the waste water detoxification, blood sterilization, cold pasteurization, and photo-deactivation commercial applications discussed in the sections above. These systems (like FIGS. 3B-3D) show the use of artificial containers in which the medium to be treated is disposed.

Figure 27:
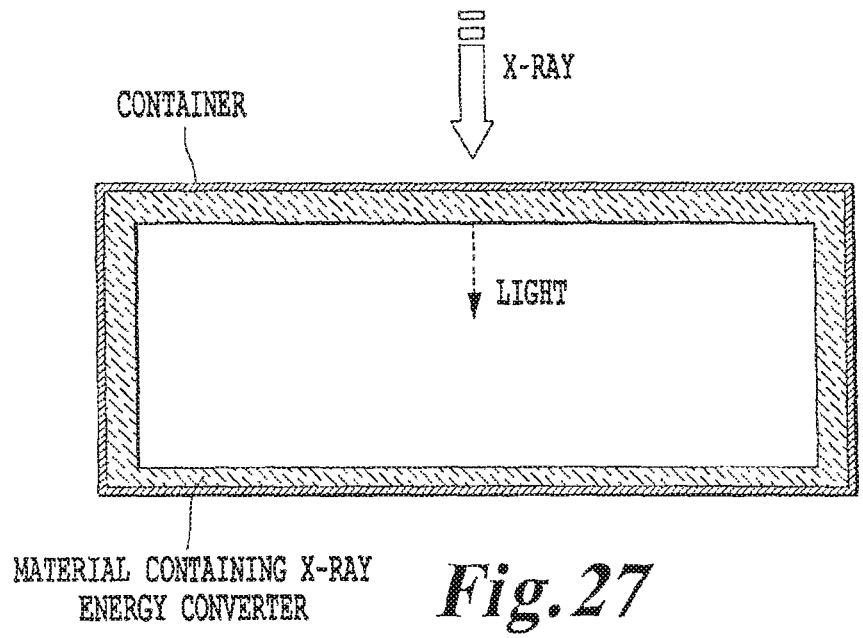
FIG. 27 is a representation of an embodiment of a sterilization system of the invention.

FIG. 27 shows one embodiment of a sterilization system of the invention that includes: a container and a material containing an X-ray energy converter. The container holds a sample to be sterilized (e.g., liquid, gas, or particulates). X-ray radiation, capable of penetrating the container wall, excites the material containing the X-ray excitation energy converter (EEC), which is configured to emit emission light. The EEC material is selected such that the emitted or luminescence light occurs in a spectral region that can be used for sterilization (e.g., the ultraviolet spectral range).

Figure 28:
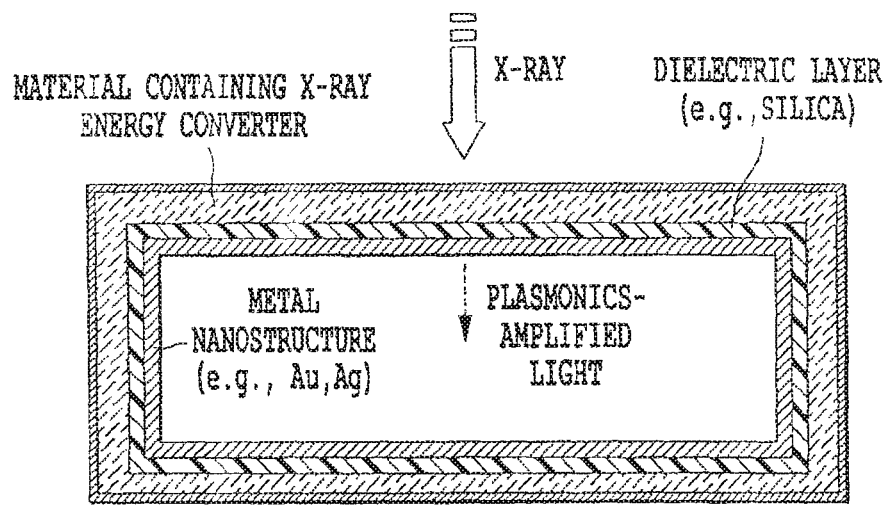
FIG. 28 is a representation of another embodiment of a sterilization system of the invention that utilizes plasmonics.

FIG. 28 shows one embodiment of another sterilization system of the invention that utilizes plasmonics and includes: a container, a material containing an X-ray energy converter, a dielectric layer (e.g., silica), and a metal nanostructure (e.g., Au, Ag). The container holds a sample to be sterilized (e.g., liquid, gas, or particulates). X-ray radiation, capable of penetrating the container wall, excites the material containing the X-ray excitation energy converter (EEC), which in turn emits emission light. The EEC material is selected such that the emitted or luminescence light occurs in a spectral region that can be used for sterilization (e.g., an ultraviolet spectral range). The metal nanostructure is designed to amplify the luminescence light due to the plasmonics enhancement effect discussed above. The dielectric layer is designed to separate the material of the X-ray energy converter from the metal nanostructure in order to minimize or prevent possible quenching of the luminescence. The optimal thickness of the dielectric layer is about 1 to 5 nm such that the dielectric layer does not significantly alter the plasmonics effect.

Figure 29:
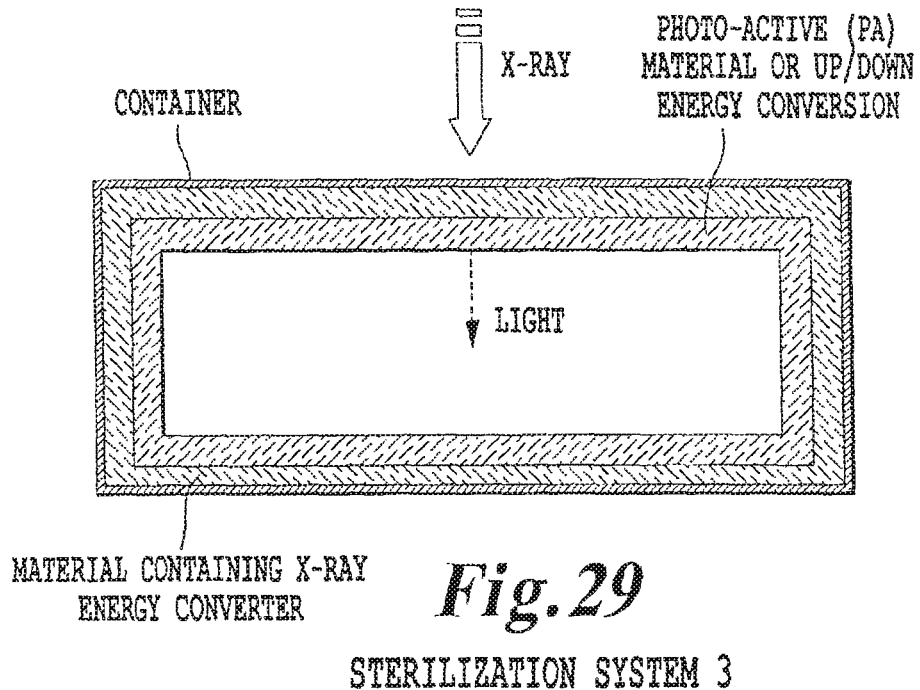
FIG. 29 is a representation of another embodiment of a sterilization system of the invention that utilizes a photoactive material.

FIG. 29 shows another embodiment of a sterilization system of the invention that includes: a container, a material containing an X-ray energy converter, and a photo-active (PA) material. X-ray radiation, capable of penetrating the container wall, excites the material containing the X-ray excitation energy converter (EEC), which in turn emits luminescence light. The EEC material is selected such that the emitted or luminescence light occurs in the spectral region that can be used to further excite the photo-active (PA) material. The photo-active material can be used for sterilization-purpose emission light (e.g., luminescence) following excitation by the EEC luminescence light. Alternatively the PA material is replaced by or is a material that has the property of up/down energy conversion of the EEC emission light in order to produce radiation at appropriate wavelengths for sterilization purposes (e.g., UV light to kill bacteria).

Figure 30:
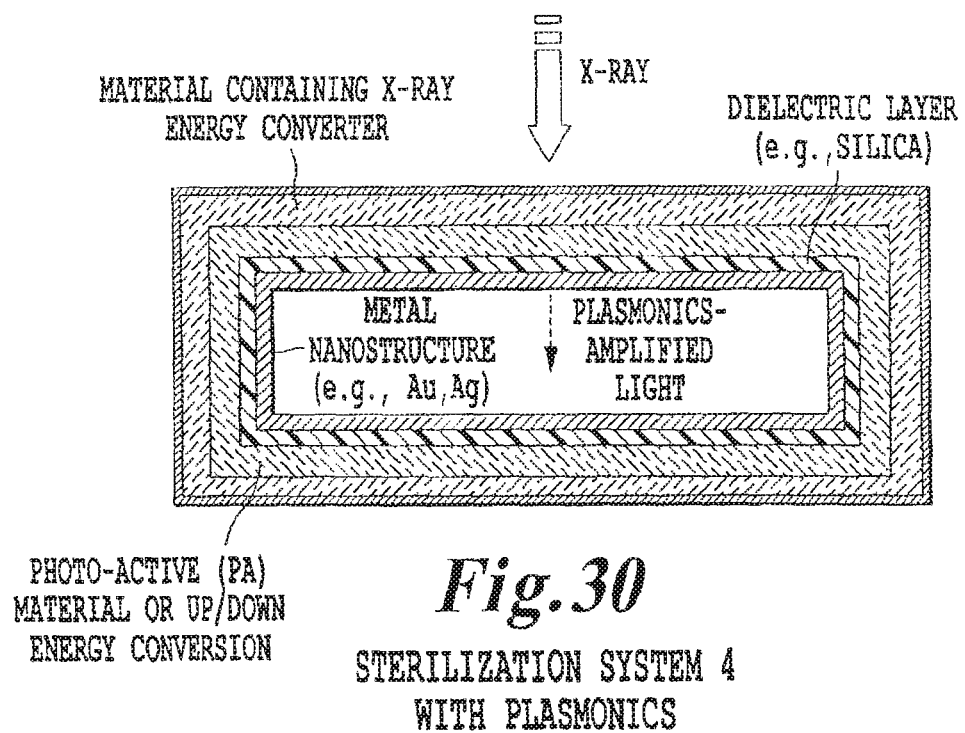
FIG. 30 is a representation of another embodiment of a sterilization system of the invention that utilizes a photoactive material and a dielectric medium.

FIG. 30 shows another embodiment of a sterilization system of the invention that includes: a container, a material including an X-ray energy converter, a dielectric layer (e.g., silica), a metal nanostructure (e.g., Au, Ag), and a photo-active (PA) material. X-ray radiation, capable of penetrating the container wall, excites the material containing the X-ray excitation energy converter (EEC), which in turn emits emission light. The EEC material is selected such that the emitted or luminescence light occurs in a spectral region that can be used to further excite a photo-active (PA) material. The photo-active material can be used for sterilization purpose emission light (e.g., luminescence) following excitation by the EEC luminescence light. Alternatively the PA material is replaced by or is a material that has the property of up/down energy conversion of the EEC emission light in order to produce radiation at appropriate wavelengths for sterilization purposes (e.g., UV light to kill bacteria). The metal nanostructure in this embodiment is designed to amplify the luminescence light due to the plasmonics enhancement effect. The dielectric layer is designed to separate the material containing X-ray energy converter and the metal nanostructure in order to prevent or minimize possible quenching of the luminescence.

Figure 31:
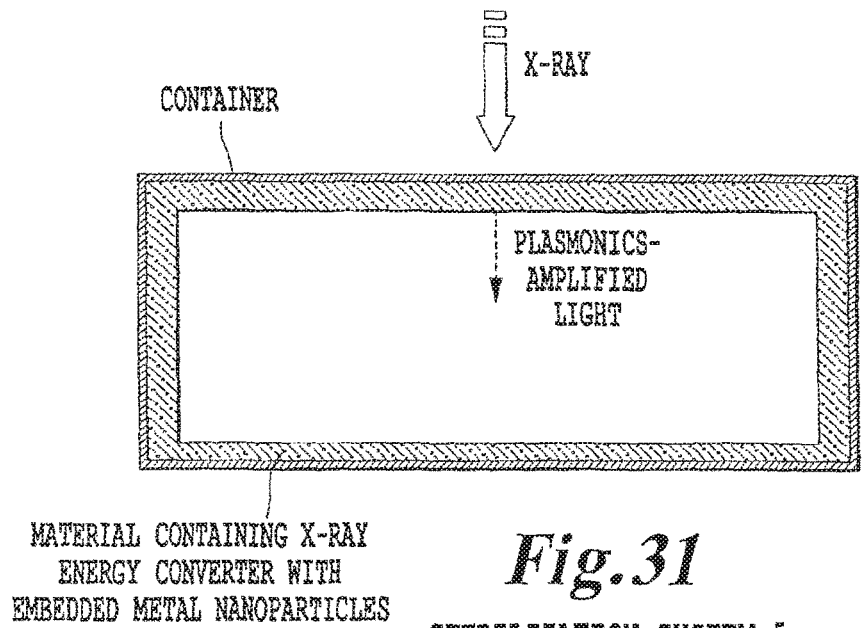
FIG. 31 is a representation of another embodiment of a sterilization system of the invention that utilizes an X-ray energy converter with embedded metal nanoparticles serving as a plasmonics function.

FIG. 31 shows another embodiment of a sterilization system of the invention that includes: a container and a material including an X-ray energy converter with embedded metal nanoparticles included as part of the walls of the container. The container holds a sample to be sterilized which can be a liquid, a gas, or particulates. The X-ray radiation, capable of penetrating the container wall, excites the material containing the X-ray excitation energy converter (EEC), which in turn emits emission light. The EEC material is selected such that the emitted or luminescence light occurs in a spectral region that can be used for sterilization (e.g., the ultraviolet spectral range). In this embodiment, the EEC material is contained in a matrix that also has metallic nanoparticles (1-100 nm diameter). The metallic nanoparticles serve as plasmonics-active systems that are designed to enhance the EEC emission light.

Figure 32:
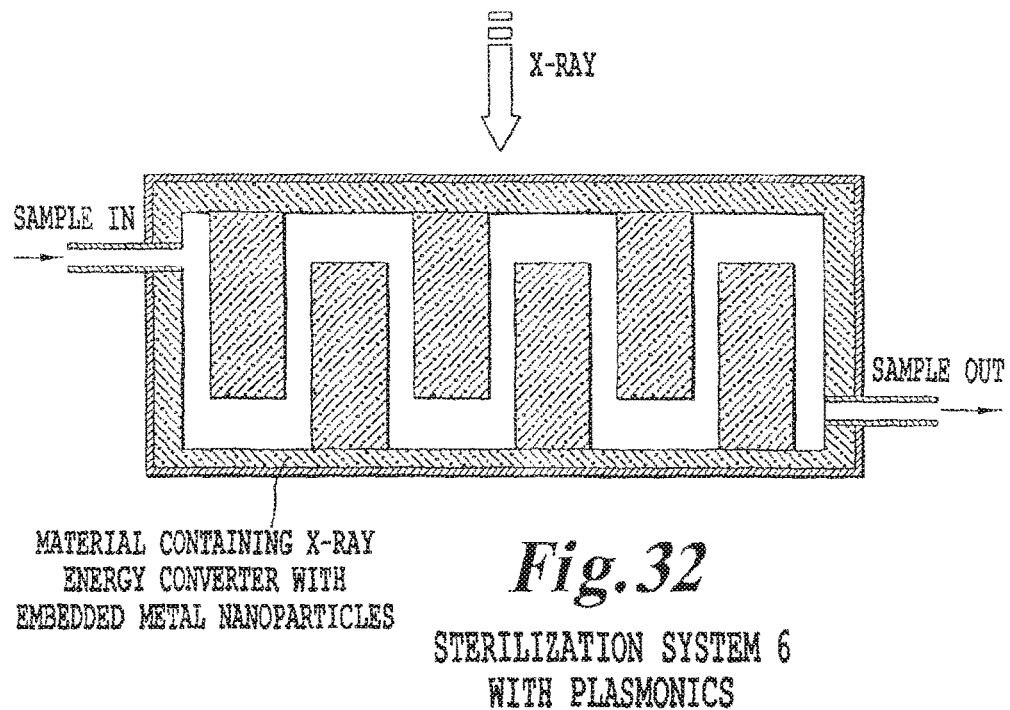
FIG. 32 is a representation of another embodiment of a sterilization system of the invention that utilizes embedded metal nanoparticles incorporated on re-entrant structures inside where a medium to be sterilized will flow.

FIG. 32 shows another embodiment of a sterilization system of the invention that includes: a container and a material including an X-ray energy converter with embedded metal nanoparticles included as part of the walls of the container and included on re-entrant structures. This embodiment is designed such that a sample flow can have maximum contact with the walls (including the re-entrant structures) of the sterilization system. The sample flowing through the container can be liquid, gas, or particulates. X-ray radiation, capable of penetrating the container wall, excites the material containing the X-ray excitation energy converter (EEC), which in turn emits emission light. The EEC material is selected such that the emitted or luminescence light occurs in a spectral region that can be used for sterilization (e.g., the ultraviolet spectral range). In this embodiment, the EEC material is contained in a matrix that also has metallic nanoparticles (1-100 nm diameter). The metallic nanoparticles serve has plasmonics-active systems that are designed to enhance the EEC emission light.

Figure 33:
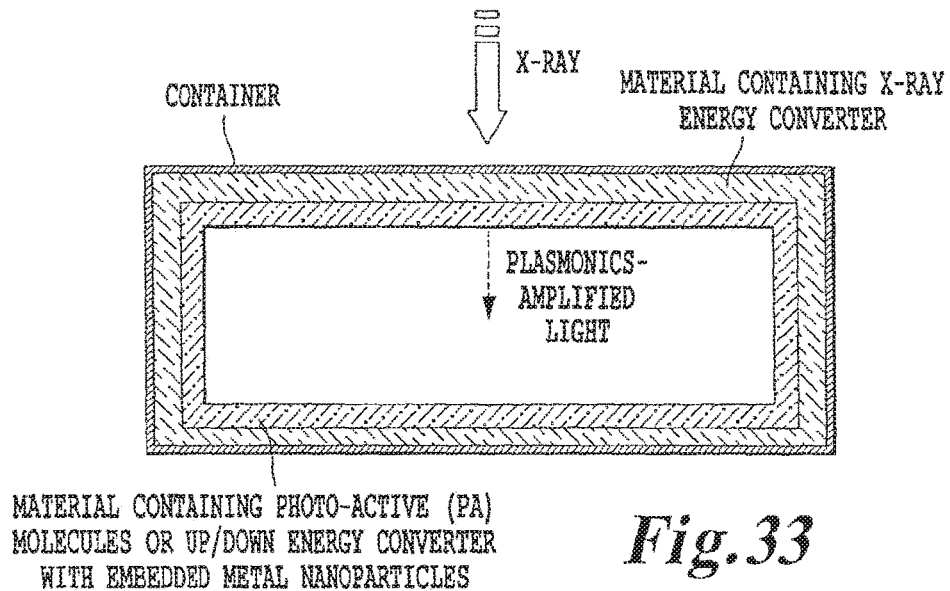
FIG. 33 is a representation of another embodiment of a sterilization system of the invention that utilizes an X-ray energy converter with the embedded metal nanoparticles of FIG. 31 included on an inside layer of a container where a medium to be sterilized will flow.

FIG. 33 shows another embodiment of a sterilization system of the invention that includes: a container, a material including an X-ray energy converter, and a photo-active material. The container holds a sample to be sterilized which can be a liquid, a gas, or particulates. X-ray radiation, capable of penetrating the container wall, excites the material containing X-ray excitation energy converter (EEC), which in turn emits emission light. The EEC material is selected such that the emitted or luminescence light occurs in the spectral region that can be used to further excite a photo-active (PA) material. The photo-active material can be used for sterilization purpose emission light (e.g., luminescence) following excitation by the EEC luminescence light. Alternatively the PA material is replaced by or is a material that has the property of up/down energy conversion of the EEC emission light in order to produce radiation at appropriate wavelengths for sterilization purposes (e.g., UV light to kill bacteria). In this embodiment, the PA material (or up/down energy conversion material) is contained in a matrix that also has metallic nanoparticles (1-100 nm diameter). The metallic nanoparticles serve has plasmonics-active systems that are designed to enhance the emission light.

Figure 34:
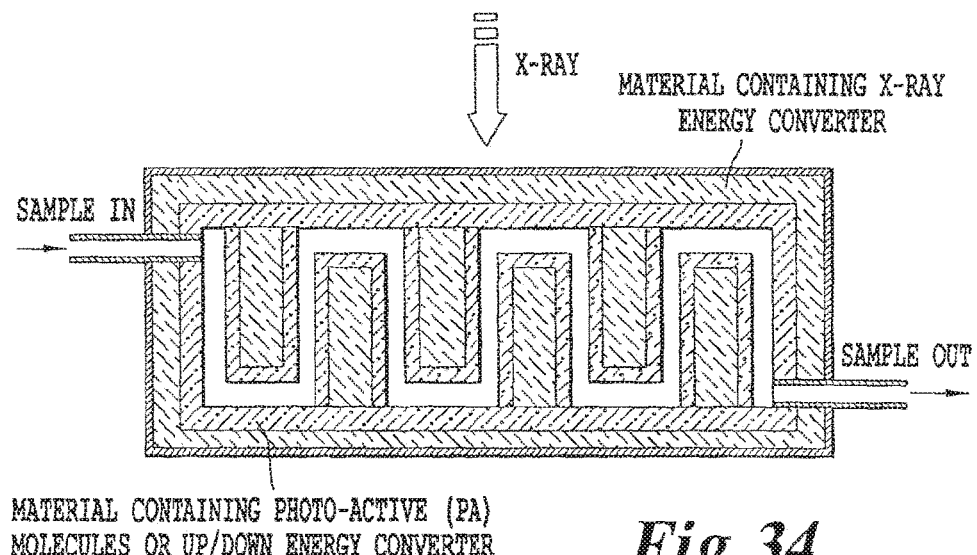
FIG. 34 is a representation of another embodiment of a sterilization system of the invention that utilizes embedded metal nanoparticles incorporated on re-entrant wall structures inside where a medium to be sterilized will flow.

FIG. 34 shows another embodiment of a sterilization system of the invention that includes: a container, a material including an X-ray energy converter with embedded metal nanoparticles included on an inside layer on the walls of the container and included on re-entrant structures, and a photo-active material. The container holds a sample to be sterilized which can be a liquid, a gas, or particulates. This embodiment is designed such that a sample flow can have frequent contact with the walls of the sterilization system. X-ray radiation, capable of penetrating the container wall, excites the material containing X-ray excitation energy converter (EEC), which in turn emits emission light. The EEC material is selected such that the emitted or luminescence light occurs in the spectral region that can be used to further excite a photo-active (PA) material. The photo-active material can be used for sterilization-purpose emission light (e.g., luminescence) following excitation by the EEC luminescence light. Alternatively, the PA material is replaced by or is a material that has the property of up/down energy conversion of the EEC emission light in order to produce radiation at appropriate wavelengths for sterilization purposes (e.g., UV light to kill bacteria). In this embodiment, the PA material (or up/down energy conversion material) is contained in a matrix that also has metallic nanoparticles (1-100 nm diameter). The metallic nanoparticles serve has plasmonics-active systems that are designed to enhance the emission light.

Figure 35:
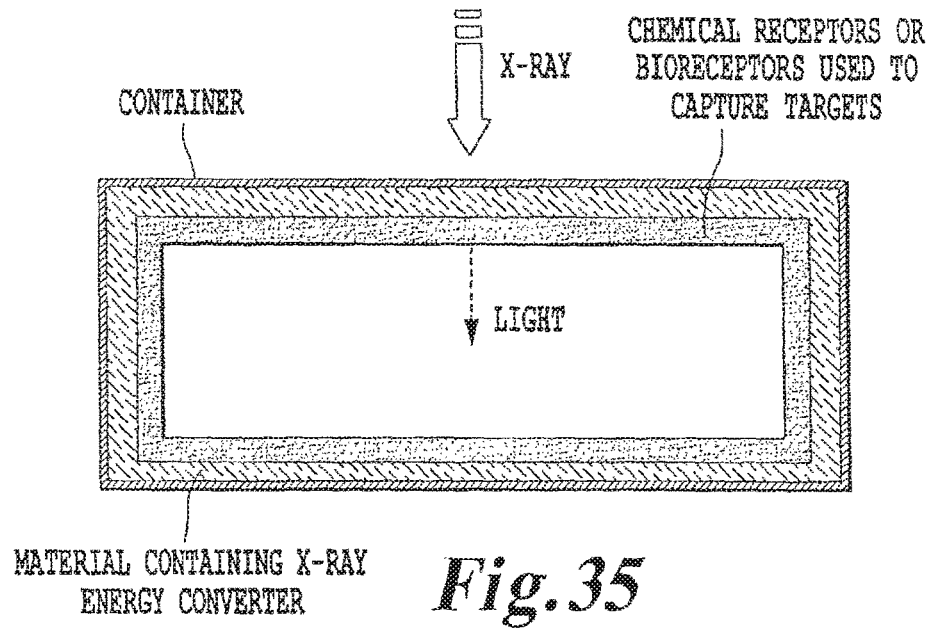
FIG. 35 is a representation of another embodiment of a sterilization system of the invention that utilizes chemical receptors on an inside of a container where a medium to be sterilized will flow.

FIG. 35 shows another embodiment of a sterilization system of the invention that includes: a container, a material including an X-ray energy converter, and chemical receptors or bioreceptors used to capture targets. The container holds a sample to be sterilized which can be a liquid, a gas, or particulates. X-ray radiation, capable of penetrating the container wall, excites the material containing X-ray excitation energy converter (EEC), which in turn emits emission light. The EEC material is selected such that the emitted or luminescence light occurs in a spectral region that can be used for sterilization (e.g., the ultraviolet spectral range). The layer of chemical receptors (e.g., ligands specific to chemical groups) or bioreceptors (e.g., antibodies, surface cell receptors) is used to capture biochemical targets of interest. In this embodiment, the specific target compounds are selectively bound to the surface and are more effectively irradiated by the emission light.

Figure 36:
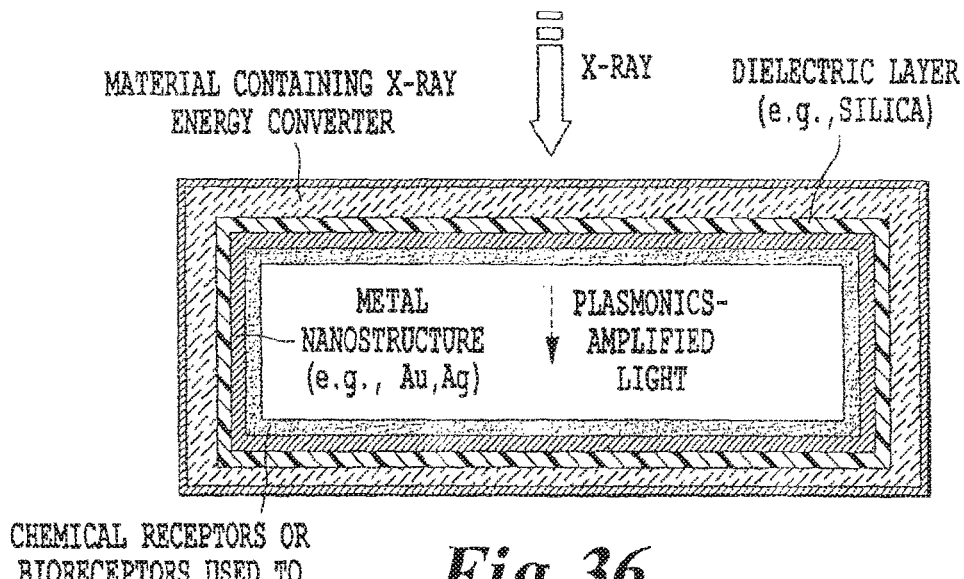
FIG. 36 is a representation of another embodiment of a sterilization system of the invention that utilizes embedded metal nanoparticles in one layer and chemical receptors in another more interior layer on an inside of a container where a medium to be sterilized will flow.

FIG. 36 shows another embodiment of a sterilization system of the invention that includes: a container, a material including an X-ray energy converter, a dielectric layer (e.g., silica), metal nanostructures (e.g., Au, Ag), and chemical receptors or bioreceptors used to capture targets. The sample inside the container can be liquid, gas, or particulates. X-ray radiation, capable of penetrating the container wall, excites the material containing X-ray excitation energy converter (EEC), which in turn emits emission light. The EEC material is selected such that the emitted or luminescence light occurs in a spectral region that can be used for sterilization (e.g., the ultraviolet spectral range). The metal nanostructure is designed to amplify the luminescence (or emitted) light due to the plasmonics enhancement effect. The dielectric layer is designed to separate the material containing X-ray energy converter and the metal nanostructure in order to prevent or minimize possible quenching of the luminescence. The optimal thickness of the dielectric layer is about 1 to 5 nm such that the dielectric layer does not significantly affect the plasmonics effect. The layer of chemical receptors (e.g., ligands specific to chemical groups) or bioreceptors (e.g., antibodies, surface cell receptors) is used to capture biochemical targets of interest. In this embodiment, the specific target compounds are selectively bound to the surface and are more effectively irradiated by the emission light.

Figure 37:
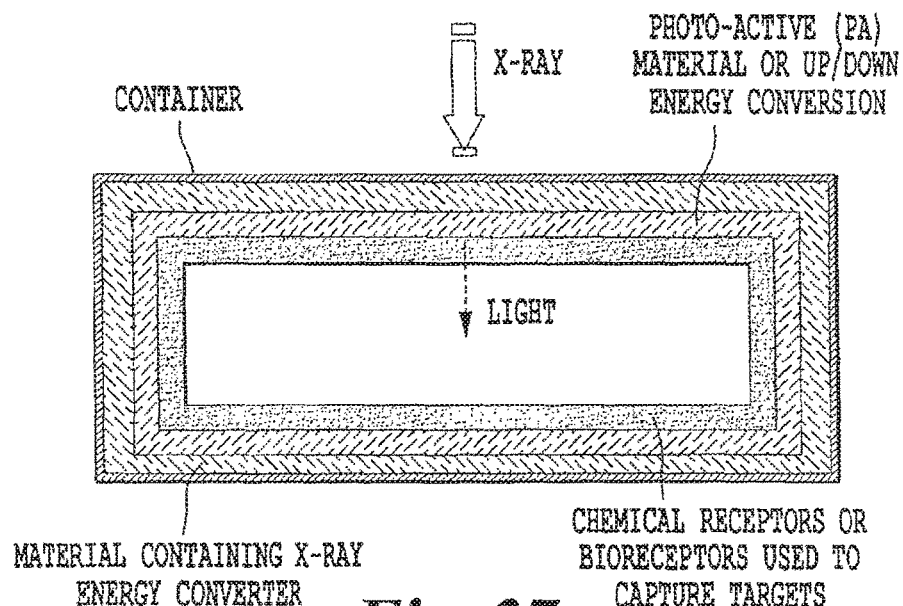
FIG. 37 is a representation of another embodiment of a sterilization system of the invention that utilizes a photo-active material and chemical receptors on an inside of a container where a medium to be sterilized will flow.

FIG. 37 shows another embodiment of a sterilization system of the invention that includes: a container, a material including an X-ray energy converter, a photo-active (PA) material, and chemical receptors or bioreceptors used to capture targets. X-ray radiation, capable of penetrating the container wall, excites the material containing X-ray excitation energy converter (EEC), which in turn emits luminescence light. The EEC material is selected such that the emitted or luminescence light occurs in a spectral region that can be used to further excite a photo-active (PA) material. The photo-active material can be used for sterilization-purpose emission light (e.g., luminescence) following excitation by the EEC luminescence light. The layer of chemical receptors (e.g., ligands specific to chemical groups) or bioreceptors (e.g., antibodies, surface cell receptors) is used to capture biochemical targets of interest. In this embodiment, the specific target compounds are selectively bound to the surface and are more effectively irradiated by the emission light. Alternatively, the PA material is replaced by or is a material that has the property of up/down energy conversion of the EEC emission light in order to produce radiation at appropriate wavelengths for sterilization purposes (e.g., UV light to kill bacteria).

Figure 38:
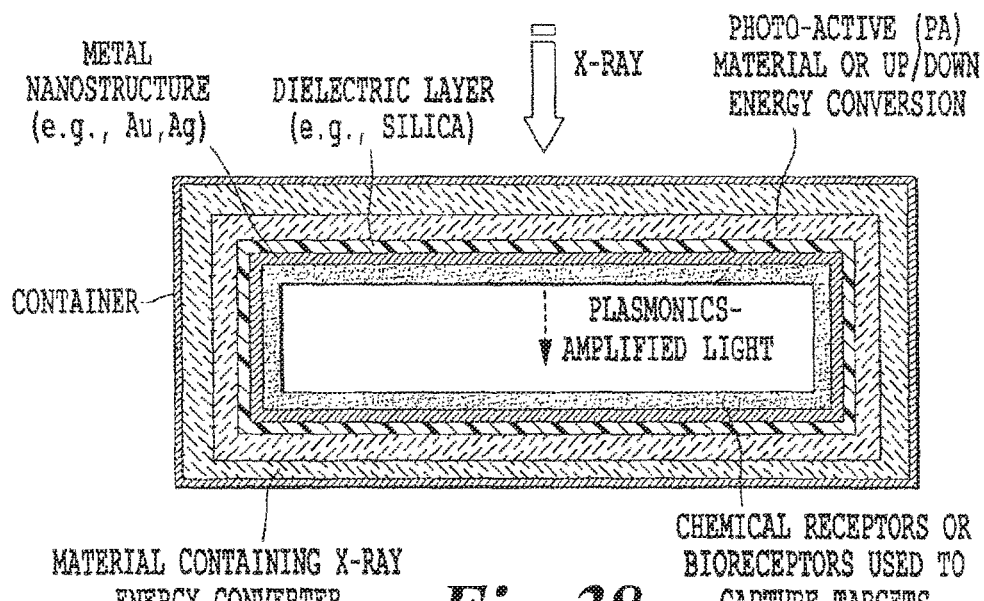
FIG. 38 is a representation of another embodiment of a sterilization system of the invention that utilizes a photo-active material, a dielectric layer in conjunction with embedded metal nanoparticles, and chemical receptors on a surface of the probe inside of a container where a medium to be sterilized will flow.

FIG. 38 shows another embodiment of a sterilization system of the invention that includes: a container, a material including an X-ray energy converter, a photo-active (PA) material, a metal nanostructure (e.g., Au, Ag), a dielectric layer (e.g., silica), and chemical receptors or bioreceptors used to capture targets. X-ray radiation, capable of penetrating the container wall, excites the material containing X-ray excitation energy converter (EEC), which in turn emits emission light. The EEC material is selected such that the emitted or luminescence light occurs in a spectral region that can be used to further excite a photo-active (PA) material. The photo-active material can be used for sterilization-purpose emission light (e.g., luminescence) following excitation by the EEC luminescence light. Alternatively, the PA material is replaced by or is a material that has the property of up/down energy conversion of the EEC emission light in order to produce radiation at appropriate wavelengths for sterilization purposes (e.g., UV light to kill bacteria). The metal nanostructure is designed to amplify the luminescence light due to the plasmonics enhancement effect. The dielectric layer is designed to separate the material containing X-ray energy converter and the metal manostructure in order to prevent or minimize possible quenching of the luminescence. The layer of chemical receptors (e.g., ligands specific to chemical groups) or bioreceptors (e.g., antibodies, surface cell receptors) is used to capture biochemical targets of interest. In this embodiment, the specific target compounds are selectively bound to the surface and are more effectively irradiated by the emission light.

The invention can use these chemical receptors and bioreceptors on interior walls contacting the medium to be sterilized in the other systems shown herein.

Figure 39:
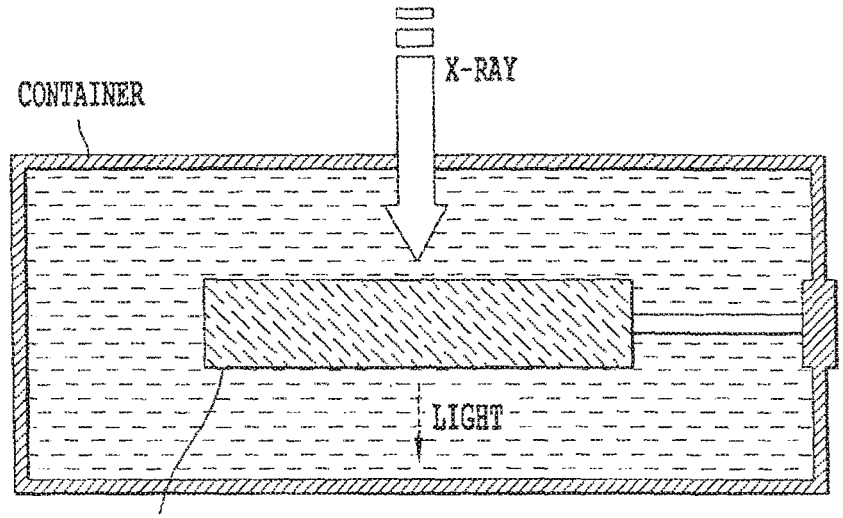
FIG. 39 is a representation of an embodiment of a sterilization probe system of the invention.

FIG. 39 shows an embodiment of a sterilization probe system of the invention that includes a container which can hold the medium to be sterilized and a probe made of material containing an X-ray energy converter. The sample inside the container can be liquid, gas, or particulates. X-ray radiation, capable of penetrating the container wall, excites the probe having the material containing X-ray excitation energy converter (EEC), which in turn emits emission light. The EEC material is selected such that the emitted or luminescence light occurs in a spectral region that can be used for sterilization (e.g., the ultraviolet spectral range). The probe can be removed and reinserted into the container and reused.

Figure 40:
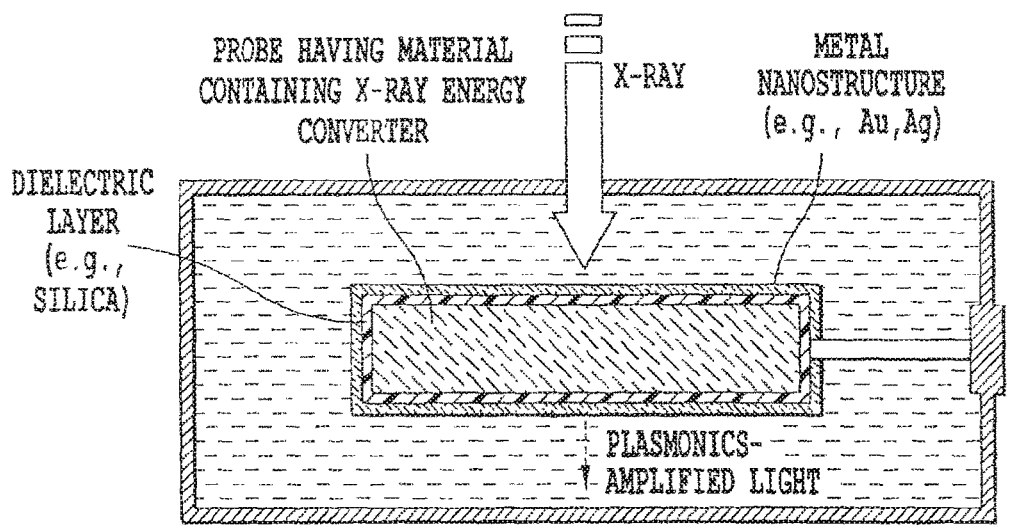
FIG. 40 is a representation of another embodiment of a sterilization probe system of the invention that utilizes a dielectric layer in conjunction with embedded metal nanoparticles.

FIG. 40 shows an embodiment of a sterilization probe system of the invention that includes a container which can hold the medium to be sterilized, a probe made of material containing an X-ray energy converter, a dielectric layer (e.g., silica), and a metal manostructure (e.g., Au, Ag). The sample inside the container can be liquid, gas, or particulates. X-ray radiation, capable of penetrating the container wall, excites the probe having a material containing X-ray excitation energy converter (EEC), which in turn emits emission light. The EEC material is selected such that the emitted or luminescence light occurs in a spectral region that can be used for sterilization (e.g., the ultraviolet spectral range). The metal nanostructure is designed to amplify the luminescence light due to the plasmonics enhancement effect. The dielectric layer is designed to separate the material containing the X-ray energy converter and the metal nanostructure in order to prevent or minimize possible quenching of the luminescence. The optimal thickness of the dielectric layer is about 1 to 5 nm such that the dielectric layer does not significantly alter the plasmonics effect. The probe can be removed and reinserted into the container and reused.

Figure 41:
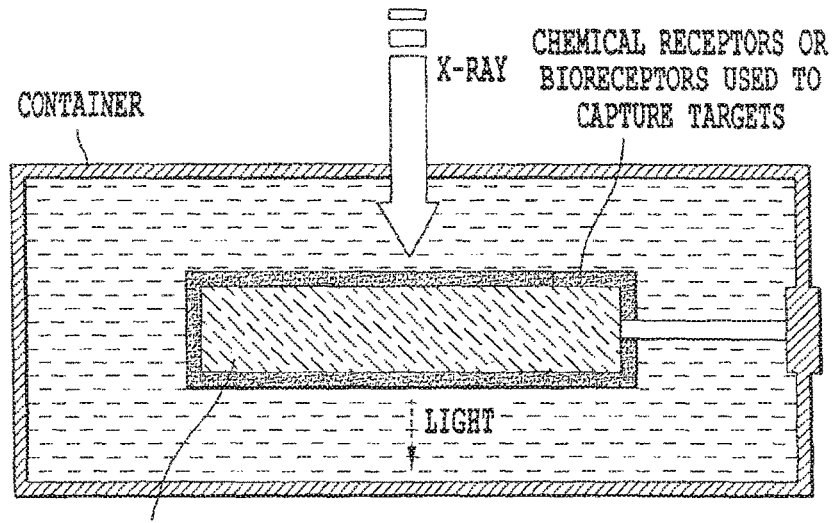
FIG. 41 is a representation of another embodiment of a sterilization probe system of the invention that utilizes an X-ray energy converter and chemical receptors on a surface of the probe inside of a container where a medium to be sterilized will flow.

FIG. 41 shows an embodiment of a sterilization probe system of the invention that includes a container which can hold the medium to be sterilized, a probe made of material containing an X-ray energy converter, and chemical receptors or bioreceptors used to capture targets. The sample inside the container can be liquid, gas, or particulates. X-ray radiation, capable of penetrating the container wall, excites the probe having a material containing X-ray excitation energy converter (EEC), which in turn emits emission light. The EEC material is selected such that the emitted or luminescence light occurs in a spectral region that can be used for sterilization (e.g., ultraviolet spectral range). The layer of chemical receptors (e.g., ligands specific to chemical groups) or bioreceptors (e.g., antibodies, surface cell receptors) is used to capture biochemical targets of interest. In this embodiment, the specific target compounds are selectively bound to the surface of the probe and are more effectively irradiated by the emission light. The probe can be removed and reinserted into the container and reused.

Figure 42:
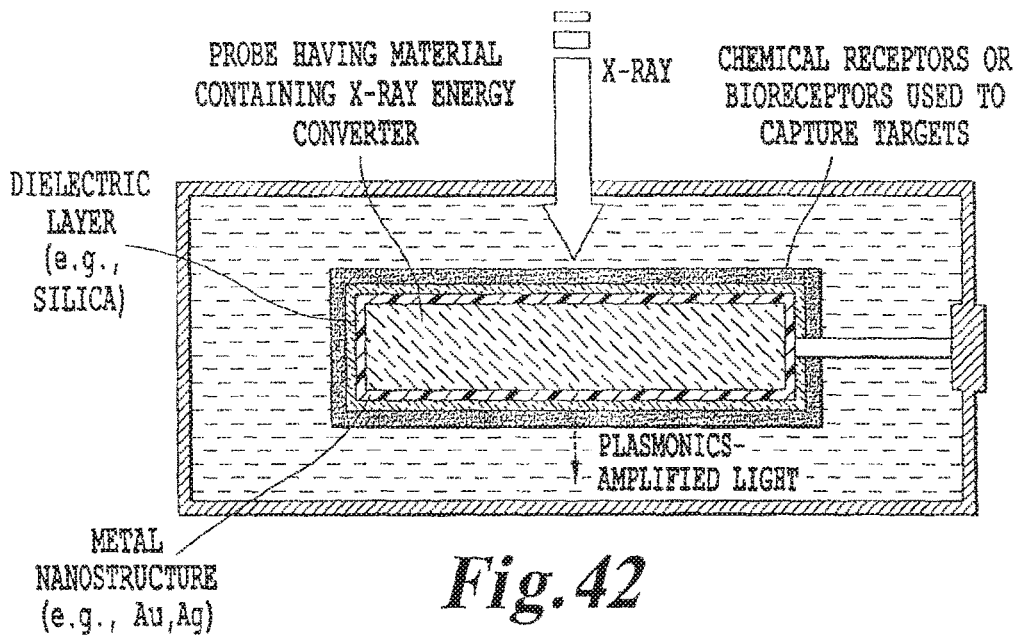
FIG. 42 is a representation of another embodiment of a sterilization probe system of the invention that utilizes an X-ray energy converter and further a dielectric layer in conjunction with embedded metal nanoparticles on a surface of the probe inside of a container where a medium to be sterilized will flow.
Figure 43A:
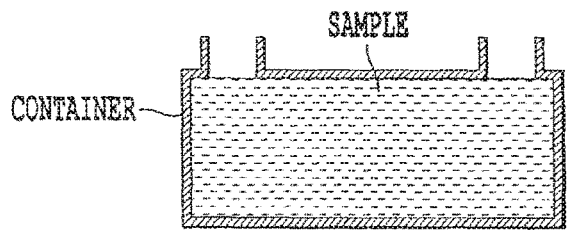
FIGS. 43A-43D are representations of another embodiment of a sterilization system of the invention that utilizes paramagnetic core materials.
Figure 43B:
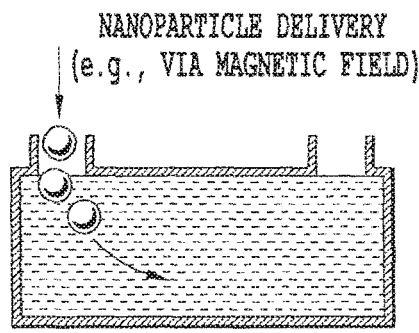
Figure 43C:
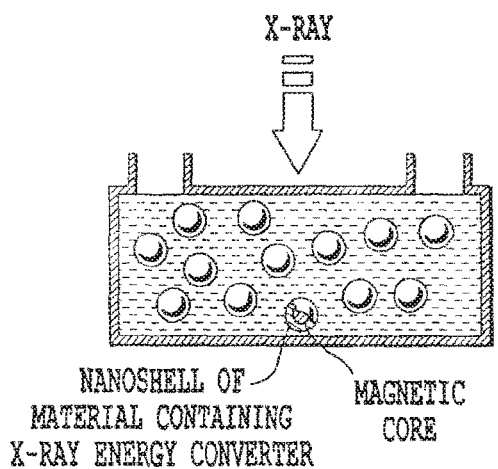
Figure 43D:
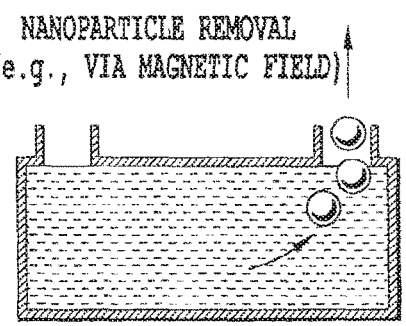

FIG. 42 shows an embodiment of a sterilization probe system of the invention that includes a container which can hold the medium to be sterilized, a probe made of material containing an X-ray energy converter, a dielectric layer (e.g., silica), and a metal manostructure (e.g., Au, Ag). The sample inside the container can be liquid, gas, or particulates. X-ray radiation, capable of penetrating the container wall, excites the probe having a material containing X-ray excitation energy converter (EEC), which in turn emits emission light. The EEC material is selected such that the emitted or luminescence light occurs in a spectral region that can be used for sterilization (e.g., the ultraviolet spectral range). The metal nanostructure is designed to amplify the luminescence light due to the plasmonics enhancement effect. The dielectric layer is designed to separate the material containing the X-ray energy converter and the metal nanostructure in order to prevent possible quenching of the luminescence. The optimal thickness of the dielectric layer is about 1 to 5 nm such that the dielectric layer does not significantly affect the plasmonics effect. The layer of chemical receptors (e.g., ligands specific to chemical groups) or bioreceptors (e.g., antibodies, surface cell receptors) is used to capture biochemical targets of interest. In this embodiment, the specific target compounds are selectively bound to the surface of the probe and are more effectively irradiated by the emission light. The probe can be removed and reinserted into the container and reused.

FIG. 43 shows an embodiment of a sterilization probe system of the invention that includes a container which can hold the medium to be sterilized, nanoparticles having 1) a paramagnetic core and 2) a shell having material containing an X-ray energy converter. The sample inside the container can be liquid, gas, or particulates. The nanoparticles, which have a paramagnetic core covered with a nanoshell of material containing the X-ray energy converter, can be delivered into the container using an externally applied magnetic field. The X-ray radiation, capable of penetrating the container wall, excites the nanoparticle shell which contains X-ray excitation energy converter (EEC) material, which in turn emits emission light. The EEC material is selected such that the emitted or luminescence light occurs in a spectral region that can be used for sterilization (e.g., the ultraviolet spectral range). After the sterilization is completed, the nanoparticles can be removed from the container using an externally applied magnetic field. The magnetic filed unit serves as a mechanism to introduce and collect the magnetic naonoparticles. The nanoparticles can be reinserted into the container and reused. In another embodiment, the nanoparticles can be also covered with a layer of chemical receptors (e.g., ligands specific to chemical groups) or bioreceptors (e.g., antibodies, surface cell receptors). That layer is used to capture biochemical targets of interest. In this embodiment, the specific target compounds are selectively bound to the surface of the probe and are more effectively irradiated by the emission light.

FIG. 44 shows examples of plasmonics probes with a paramagnetic core. In FIG. 44A, the magnetic core is surrounded by a metal layer which is in turn surrounded by a dielectric layer. In FIG. 44B, the magnetic core is surrounded by an X-ray excitation energy converter (EEC) material which is in turn surrounded by a dielectric layer. Metal nanoparticles are attached to the dielectric. In FIG. 44C, the magnetic core is surrounded by a metal layer which is in turn surrounded by a dielectric layer. An X-ray excitation energy converter (EEC) material is formed as a partial cap on the dielectric layer. In FIG. 44D, the magnetic core is surrounded by an X-ray excitation energy converter (EEC) material which is in turn surrounded by a dielectric layer. A metal layer is formed as a partial cap on the dielectric layer. In FIG. 44E, the magnetic core is surrounded by a metal layer which is in turn surrounded by a dielectric layer, which is in turn surrounded by an X-ray excitation energy converter (EEC) material. In FIG. 44F, the magnetic core is surrounded by an X-ray excitation energy converter (EEC) material which is in turn surrounded by a dielectric layer, which is in turn surrounded by a metal layer. In FIG. 44G, the magnetic core is surrounded by an X-ray excitation energy converter (EEC) material which is in turn surrounded by a dielectric layer, which is in turn surrounded by a metal layer and which in turn is surrounded by a chemical receptor layer.

Design and Fabrication of Plasmonics-Active Materials and Surfaces

The plasmonics-active surfaces and probes in the embodiments described above can be prepared using one of the following procedures to produce nanostructures of metal or thin layers of metal that exhibit plasmonics properties.

For nanostructures produced on metal electrode systems, electrochemical cells using silver electrodes and other metal electrodes have been used to produce nanostructured morphology on the surface of electrodes for SERS studies (Pettinger B., U. Wenneng and H. Wetzel, *Surface-plasmon enhanced Raman-scattering frequency and . . . Ag and Cu electrodes,* 1980, Surf. Sci., 101, 409; Fleishman M., P. R. Graves, and J. Robinson. The Raman-*Spectroscopy of the . . . hydride and platinum-electrodes,* 1985, J. Electroanal. Chem., 182, 87). The fabrication procedures described in these references (which are incorporated in their entirety herein by reference) are applicable to the invention. Silver at an electrode is oxidized by the reaction Ag - - - >Ag++e$^-$ during the first half of the cycle. During the reduction half cycle, a roughened silver surface is reproduced by the reaction Ag++e$^-$ - - - >Ag. This oxidation-reduction procedure generally produces surface protrusions in the size range of 25 to 500 nm on the electrode surface. The working electrode can then be generally placed in a position such that the laser excitation can be focused onto its surface, and the Raman scattered light can be efficiently collected by appropriate optics. A strong SERS signals appear in general only after an electrochemical oxidation-reduction cycle, often referred to as "activation cycle," is performed on the metal electrode. The fabrication procedures described in these references (which are incorporated in their entirety herein by reference) for the respective electrodes are applicable to the invention.

Other metal electrodes such as platinum (Loo B H., *Surface-enhanced Raman-spectroscopy of platinum,* 1983, J. Phys. Chem., 87, 3003) have also been investigated as plasmonics substrates. Experimental factors such as the influence of laser illumination of copper electrodes during oxidation/reduction treatment on SERS signals of pyridine and benzotriazole have been investigated (Thierry D. and C. Leygraf. *The influence of photoalteration on surface-enhanced. Raman scattering from copper electrodes,* 1985, Surface Sci., 149, 592). Beer, K. D.; Tanner. W.; Garrell, R L. in *J. Electroanal.* Chem. 1989, 258, 313-325, have investigated the ex-situ versus in-situ electrode roughening procedures for SERS on gold and silver electrode surfaces. The fabrication procedures described in these references (which are incorporated in their entirety herein by reference) for the respective electrodes are applicable to the invention.

For chemically, electrochemically etched metal and other roughened surfaces, chemical etching procedures can also be used to produce plasmonics active metal surfaces (Miller S. K., A. Baiker, M. Meier, and A. Wokaun, *Surface-enhanced Raman scattering and the preparation of copper substrates for catalytic studies,* 1984, J. Chem. Soc. Farad. Trans. 1, 80, 1305). In one procedure, copper foil is etched for 40 min. in 2 mol. dm$^{-3}$ nitric acid at room temperature. Another procedure includes sandblasting copper foil with Al$_2$O$_3$ at 4 bar pressure and subsequently etching for 2 min. SEM pictures of the metal surfaces indicate that both etching procedures can produce surface roughness on the 10 to 100 nm scale. Electrochemically roughened silver oxide substrates have been developed to detect vapor of chemical nerve agent simulants (Taranenko N., J. P. Alarie, D. L. Stokes, and T. Vo Dinh, *Surface-Enhanced Raman Detection of Nerve Agent Simulant (DMMP and DIMP) Vapor on Electrochemically Prepared Silver Oxide Substrates,* 1996, J. Raman Spectr., 27, 379-384). These procedures are consistent and similar to electroplating methods. The fabrication procedures described in these references (which are incorporated in their entirety herein by reference) are applicable to the invention.

For metallic nanostructures on solid substrates, a variety of procedures to coat solid substrates with metal nanostructures have been described previously [Vo-Dinh, *Surface-Enhanced Raman Spectroscopy Using Metallic Nanostructures,* 1998, Trends in Analytical Chemistry, 17, 557 (1998)]. These procedures can be used to produce plasmonics-active surfaces and embodiments. The fabrication procedures described in this reference (which is incorporated in its entirety herein by reference) are applicable to the invention.

In various embodiments of the invention, the interior walls can also have an appropriate protective coating that is optically transparent to the emitting light used for sterilization.

For metal nanoparticle island films, the simplest metallic nanostructure can be produced by evaporating a thin layer (e.g., less than 10 nm thickness) of a metal such as silver directly onto a solid base support. Under these conditions, the silver layer forms nanoparticles on the support in the form of isolated metal islands. Upon an increase of the deposited silver thickness, the particles would start to coalesce and form a continuous film. The size and shape of the metal nanoparticles can be influenced by varying the thickness of metal deposited (as measured by a quartz crystal monitor perpendicular to the evaporation source). SERS measurements using silver nanoparticle island films were compared with those obtained with other nanostructures materials. SERS from copper and zinc phthalocyanine complexes from silver and indium island films were reported (Jennings C., R. Aroca, A. M. Hor, and R. O. Loutfy, *Surface-enhanced Raman scattering from copper and zinc phihalocyanine complexes by silver and indium island films,* 1984, Anal. Chem., 56, 203). The silver and indium films were vacuum-evaporated (p<$10^{-6}$ Torr) onto tin oxide glass slides and then coated with copper and zinc phthalocyanine complexes in a vacuum system at a base pressure of $5\times10^{-7}$ Torr. Metal thickness was about 7.5 nm on the substrates in order to produce metal nanoparticle islands. Another alternative method involves sputter deposited thin films of metals as plasmonics substrates (Ni F., R. Sheng, and T. M. Cotton. *Flow-injection analysis and real-time . . . bases by surface-enhanced Raman-spectroscopy,* 1990, Anal. Chem., 62, 1958). The fabrication procedures described in these references (which are incorporated in their entirety herein by reference) are applicable to the invention.

For metal-coated nanosphere substrates, one of the earlier difficulties in the development of the SERS technique for analytical applications had been the production of surfaces or media that had an easily controlled protrusion size (roughness) and reproducible structures. One approach has involved the use of nanospheres applied onto a solid surface (e.g., container wall) in order to produce and control the desired roughness. The nanostructured support is subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex spheres are commercially available in a wide variety of sizes. The shapes of these materials are very regular and their size can be selected for optimal enhancement. The effect of the sphere size and metal layer thickness have indicated that, for each sphere size, there is an optimum silver layer thickness for which the maximum SERS signal is observed (Moody R. L., T. Vo Dinh, and W. H. Fletcher, *Investigation of Experimental Parameters for Surface-Enhanced Raman Spectroscopy,* 1987, Appl. Spectr., 41, 966). The silver-coated nanospheres were found to be among the most strongly enhancing substrates investigated, with enhancement factors comparable to or greater than those found for electrochemically roughened surfaces. The fabrication procedures described in this reference (which is incorporated in its entirety herein by reference) are applicable to the invention.

For metal-coated alumina nanoparticles, SERS studies have shown that nanoparticles with irregular shapes can also be used (instead of regularly shaped nanospheres) to spin-coat solid substrates. For instance, alumina appears to be one of the most efficient materials for the production of plasmonics-active substrates. The preparation of the substrate is similar to that with fumed silica (Bello J. M. D. L. Stokes and T. Vo Dinh, *Silver-Coated Aluminum as a New Medium for Surface-Enhanced Raman Scattering Analysis,* 1989, Appl. Spectrosc., 43, 1325). One important advantage of alumina over Teflon or latex nanospheres is its very low cost. The alumina surface consists of randomly distributed surface agglomerates and protrusions in the 10 to 100 nm range. These structures produce large electromagnetic fields on the surface when the incident photon energy is in resonance with the localized surface plasmons. Alumina-based substrates, due to their efficiency, low cost and simplicity for preparation, have led to a wide variety of practical applications. Furthermore, the reproducibility of alumina-based SERS substrates is excellent; the relative standard deviation was found to be less than 5% (Sutherland, *A Portable Surface-Enhanced Raman Spectrometer,* Instrumentation Science & Technology, Volume 22, Issue 3 Aug. 1994, pages 231-239). The fabrication procedures described in these references (which are incorporated in their entirety herein by reference) are applicable to the invention.

For silver-coated titanium dioxide nanoparticles, titanium dioxide is an alternate material that can be used to produce the nanostructure roughness when coated on surfaces. The procedures to prepare these substrates are similar to that used for nanospheres and alumina particles. Titanium dioxide materials are first deposited on glass and cellulose substrates and then coated with a 50 to 100 nm layer of silver by thermal evaporation as described previously. Prior to deposition, titanium dioxide is prepared as a suspension in water (10% concentration by weight). The silver-coated titanium oxide surfaces obtained by this method provide efficient plasmonics-active substrates (See U.S. Pat. No. 7,267,948 whose entire contents are incorporated herein by reference). Titanium dioxide provides the necessary surface nanosized roughness for the plasmonics effect. Limits of detection of various compounds are in the part per billion (ppb) levels and demonstrate the analytical usefulness of this substrate for trace analysis.

For silver-coated silica nanoparticles, another type of substrate that is quite plasmonics active and easy to prepare is the fumed silica-based substrate (Alak A., and T. Vo Dinh, *Silver-Coated Fumed Silica as New Substrate Materials for Surface-Enhanced Raman Scattering,* 1989, Anal. Chem., 61, 656). Fumed silica has been used as a thickening agent in various industrial processes, including coating and cosmetics preparations. In the preparation of plasmonics, the selection of the appropriate types of fumed silica is important. Fumed silica is manufactured in different grades, which vary with respect to surface area, particle diameter, and degree of compression. The fumed silica particles are suspended in a 10% water solution and coated onto a glass plate or filter paper. The substrate is then coated with a 50 to 100 nm layer of silver by thermal evaporation. With this type of substrate, the fumed silica material, which has nano-sized structures, provides a rough surface effect for the plasmonics process. The fabrication procedures described in this reference (which is incorporated in its entirety herein by reference) are applicable to the invention.

Plasmonica-active surfaces can be fabricated using lithographic techniques to produce controlled surface roughness have been investigated (Liao P. F., and M. B. Stern, *Surface-enhanced Raman scattering on gold and aluminum particle arrays*, 1982, Opt. Lett., 7, 483). These surfaces include uniform arrays of isolated silver nanoparticles which are uniform in shape and size. These surfaces produce a Raman enhancement on the order of 107 and have been used to test the electromagnetic model of SERS. The effectiveness of crossed-grating plasmonics substrates has been compared to that of $CaF_2$ roughened film, island film, and etched quartz (Vo Dinh T., M. Meier, and A. Wokaun. 1986, *Surface Enhanced Raman Spectroscopy with Silver Particles on Stochastic Post Substrates*, Anal. Chim. Acta, 181, 139). The fabrication procedures described in these references (which are incorporated in their entirety herein by reference) are applicable to the invention.

Plasma-etched substrates can also be used in the invention. It is often difficult to produce periodic structures over large areas by lithographic techniques. The procedure using etched quartz posts avoids this difficulty by using an island film as an etch mask on a $SiO_2$ substrate (Enlow P. D., M. C. Buncick, R. J. Warmack, and T. Vo Dinh, *Detection of Nitro polynuclear Aromatic Compounds by Surface Enhanced Raman Spectroscopy*, 1986, Anal. Chem., 58, 1119). The preparation of $SiO_2$ prolate nanorods is a multistep operation that involves plasma etching of $SiO_2$ with a silver island film as an etch mask. Since fused quartz is etched much more slowly than is thermally deposited quartz, a 500 nm layer of $SiO_2$ is first thermally evaporated onto fused quartz, at a rate of 0.1 to 0.2 nm/s. The resulting crystalline quartz is annealed to the fused quartz for 45 min. at approximately 950° C. A 5 nm silver layer is then evaporated onto the thermal $SiO_2$ layer and the substrate is flash heated for 20 s at 500° C. This heating causes the thin silver layer to bead up into small globules, which act as etch masks. The substrate is then etched for 30 to 60 min. in a $CHF_3$ plasma to produce submicron prolate $SiO_2$ posts, which are then coated with a continuous 80 nm silver layer at normal evaporation angle. Another method includes varying the angle of evaporation in order to produce silver nanoparticles on the tips of the quartz posts (Vo Dinh T., M. Meier, and A. Wokaun, *Surface Enhanced Raman Spectroscopy with Silver Particles on Stochastic Post Substrates*, 1986, Anal. Chim. Acta, 181, 139). The fabrication procedures described in these references (which are incorporated in their entirety herein by reference) are applicable to the invention.

Metal-coated cellulose substrates can also be used in the invention. These substrates can be used as (disposable) inner linings of containers. Direct metal coating of special filter papers coated with silver could provide useful substrates. Certain types of micropore filter papers coated with a thin layer of evaporated silver appear to provide efficient plasmonics-active substrates. Scanning electron micrographs of these cellulosic materials have shown that these surfaces consist of fibrous 10 nm strands with numerous tendrils that provide the necessary protrusions required for the SERS enhancement.

Silver membranes can also be used in the invention. These membranes can be also used in the inner lining of containers. One of the simplest types of solid substrates is a silver membrane used for air particulate sampling (Vo Dinh T., 1989, *Surface-Enhanced Raman Spectrometry, in Chemical Analysis of Polycyclic Aromatic Compounds*, Wiley, T. Vo-Dinh, Ed., New York.). The filter already has nano/micropores and interstices that provide the nano/micro features (e.g., nano/micro arrays) required to induce SERS. Since these membranes, include silver, these membranes can be used directly as plasmonics-active substrates without necessarily adding additional silver. The fabrication procedures described in this reference (which is incorporated in its entirety herein by reference) are applicable to the invention.

There a large variety of micro/nanofabrication techniques that can be used to produce nanostructures on metal substrates. These techniques include (but not limited to) 1) lithography such as for example electron beam lithography; photolithography, and nanoimprint tithography, 2) dry etching such as for example reactive ion etching (RIE), inductively coupled plasma (ICP) etching, and plasma etching, 3) thin film deposition and processing, 4) focused ion beam (FIB), 5) e-beam and thermal evaporation, 6) plasma enhanced chemical vapor deposition (PECVD), 7) sputtering, and 8) nanoimprinting Further, a sol-gel matrix with embedded silver or other metal nanoparticles can also be used in the invention. An optically translucent material has been prepared that acts as a plasmonics-active substrate [M. Volcan, D. L. Stokes and T. Vo-Dinh, *A Sol-Gel Derived AgCl Photochromic Coating on Glass for SERS Chemical Sensor Application*, Sensors and Actuators B, 106, 660-667 (2005)]. This material is a silica matrix, synthesized by the sol-gel method and containing in-situ precipitated AgCl particles which serve as precursors for nanoparticles of elemental silver. Reduction of AgCl to silver nanoparticles is achieved by UV irradiation. The plasmonics-active medium was distributed on solid, hence producing thin, sturdy, and optically translucent substrates. This procedure can be further adapted to produce coatings with embedded metal nanoparticles discussed above. The fabrication procedures described in this reference (which is incorporated in its entirety herein by reference) are applicable to the invention.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The claims read as follows:

1. A method for producing a change in a medium, comprising:
   (1) placing inside the medium an activatable agent,
   (2) placing inside the medium a plasmonics agent and a photon emitter which is capable of emitting therefrom at least one of ultraviolet and visible light into the medium to be treated, wherein said photon emitter comprises a member selected from the group consisting of an up converter and a light needle emitting said at least one of ultraviolet and visible light;

(3) emitting from said photon emitter said at least one of ultraviolet and visible light at one or more positions inside the medium to be treated, wherein the plasmonics agent enhances the at least one of ultraviolet and visible light emitted from said photon emitter; and (4) inducing from the light emitted into the medium a photoreactive change inside the medium.

2. The method of claim 1, wherein said activatable agent is capable of producing a pharmacological, cellular, chemical, electrical, or mechanical effect in a medium.

3. The method of claim 1, wherein said photon emitter comprises an up converter excited by an infrared source.

4. The method of claim 1, wherein said photon emitter comprises a plasmonics agent for enhancing an intensity of the light emitted into the medium.

5. The method of claim 1, wherein said photon emitter comprises a light needle emitting said at least one of ultraviolet and visible light.

6. The method of claim 1, wherein placing inside the medium a photoactivatable agent comprises placing the photoactivatable agent inside a patient.

7. The method of claim 1, wherein placing inside the medium a photoactivatable agent comprises placing a psoralen, a coumarin, or a derivative thereof inside a patient.

8. The method of claim 1,
wherein placing inside the medium a photoactivatable agent comprises placing a psoralen, a coumarin, or a derivative thereof inside a patient, and
wherein the psoralen, the coumarin, or the derivative thereof is activated by said at least one of ultraviolet and visible light.

9. The method of claim 1, wherein the photoreactive change inside the medium treats a disorder.

10. The method of claim 1, wherein the photoreactive change inside the medium treats a cancer or a tumor.

11. The method of claim 1, wherein the photoreactive change inside the medium treats an autoimmune deficiency.

12. The method of claim 1, wherein the photoreactive change inside the medium sterilizes the medium.

13. The method of claim 1, wherein the photoreactive change inside the medium cures resins in the medium.

14. The method of claim 1, wherein the activatable agent placed inside the medium is a photocatalyst, and the photoreactive change inside the medium treats a fluid medium by interaction of the at least one of ultraviolet and visible light with the photocatalyst.

15. The method of claim 1, wherein the photoreactive change inside the medium treats a cancer by inducing autovaccine response in a patient.

16. The method of claim 1, wherein the photoreactive change inside the medium treats a cancer by inducing apoptosis of cancer cells in a patient.

17. A method for producing a change in a medium, comprising:

(1) placing inside the medium an activatable agent capable of producing a pharmacological or cellular change in the medium, (2) placing inside the medium a plasmonics agent and a photon emitter which is capable of emitting therefrom at least one of ultraviolet and visible light into the medium to be treated, wherein said photon emitter comprises a member selected from the group consisting of a down converter excited by x-ray or a high energy source, an up converter excited by an infrared source and a light needle emitting said at least one of ultraviolet and visible light;

(3) emitting from said photon emitter said at least one of ultraviolet and visible light at one or more positions inside the medium to be treated, wherein the plasmonics agent enhances the at least one of ultraviolet and visible light emitted from said photon emitter; and (4) inducing from the light emitted into the medium a photoreactive change inside the medium.

18. The method of claim 17, wherein said photon emitter comprises a down converter excited by x-ray or a high energy source.

19. The method of claim 17, wherein said photon emitter comprises an up converter excited by an infrared source.

20. The method of claim 17, wherein said photon emitter comprises a plasmonics agent for enhancing an intensity of the light emitted into the medium.

21. The method of claim 17, wherein said photon emitter comprises a light needle emitting said at least one of ultraviolet and visible light.

22. The method of claim 17, wherein placing inside the medium a photoactivatable agent comprises placing the photoactivatable agent inside a patient.

23. The method of claim 17, wherein placing inside the medium a photoactivatable agent comprises placing a psoralen, a coumarin, or a derivative thereof inside a patient.

24. The method of claim 17,
wherein placing inside the medium a photoactivatable agent comprises placing a psoralen, a coumarin, or a derivative thereof inside a patient, and
wherein the psoralen, the coumarin, or the derivative thereof is activated by said at least one of ultraviolet and visible light.

25. The method of claim 24, wherein said at least one of ultraviolet and visible light is emitted into the patient from at least one of a down converter excited by x-ray or a high energy source, an up converter excited by an infrared source, a light needle, and a fiber optic.

26. The method of claim 17, wherein the photoreactive change inside the medium treats a disorder.

27. The method of claim 17, wherein the photoreactive change inside the medium treats a cancer or a tumor.

28. The method of claim 17, wherein the photoreactive change inside the medium treats an autoimmune deficiency.

29. The method of claim 17, wherein the photoreactive change inside the medium sterilizes the medium.

30. The method of claim 17, wherein the photoreactive change inside the medium treats a cancer by inducing an autovaccine response in a patient.

31. The method of claim 17, wherein the photoreactive change inside the medium treats a cancer by inducing apoptosis of cancer cells in a patient.

32. A method for producing a change in a medium, comprising:

(1) placing inside the medium an activatable agent, (2) placing inside the medium a plasmonics agent and a photon emitter which is capable of emitting therefrom at least one of ultraviolet and visible light into the medium to be treated;

(3) emitting from said photon emitter said at least one of ultraviolet and visible light at one or more positions inside the medium to be treated, wherein the plasmonics agent enhances the at least one of ultraviolet and visible light emitted from said photon emitter; and (4) inducing from the light emitted into the medium a photoreactive change inside the medium, wherein the photoreactive change inside the medium treats a cancer by inducing an autovaccine response in a patient or by inducing apoptosis of cancer cells in a patient or both.

33. The method of claim 32, wherein said photon emitter comprises a down converter excited by x-ray or a high energy source.

34. The method of claim 32, wherein said photon emitter comprises an up converter excited by an infrared source.

35. The method of claim 32, wherein said photon emitter comprises a plasmonics agent for enhancing an intensity of the light emitted into the medium.

36. The method of claim 32, wherein said photon emitter comprises a light needle emitting said at least one of ultraviolet and visible light.

37. The method of claim 32, wherein said photon emitter comprises a fiber optic emitting said at least one of ultraviolet and visible light.

38. The method of claim 32, wherein placing inside the medium a photoactivatable agent comprises placing the photoactivatable agent inside a patient.

39. The method of claim 32, wherein placing inside the medium a photoactivatable agent comprises placing a psoralen, a coumarin, or a derivative thereof inside a patient.

40. The method of claim 32,
wherein placing inside the medium a photoactivatable agent comprises placing a psoralen, a coumarin, or a derivative thereof inside a patient, and
wherein the psoralen, the coumarin, or the derivative thereof is activated by said at least one of ultraviolet and visible light.

41. The method of claim 40, wherein said at least one of ultraviolet and visible light is emitted into the patient from at least one of a down converter excited by x-ray or a high energy source, an up converter excited by an infrared source, a light needle, and a fiber optic.

42. The method of claim 32, wherein the photoreactive change inside the medium treats a cancer or a tumor.

43. The method of claim 32, wherein the photoreactive change inside the medium treats a cancer by inducing an autovaccine response in a patient.

44. The method of claim 32, wherein the photoreactive change inside the medium treats a cancer by inducing apoptosis of cancer cells in a patient.

* * * * *

UNITED STATES PATENT AND TRADEMARK OFFICE
CERTIFICATE OF CORRECTION

PATENT NO. : 10,201,796 B2
APPLICATION NO. : 15/443656
DATED : February 12, 2019
INVENTOR(S) : Frederic A. Bourke et al.

It is certified that error appears in the above-identified patent and that said Letters Patent is hereby corrected as shown below:

On the Title Page

On page 5, Column 1, item (56), other publications, Line 10, "Biometerials," should read --Biomaterials,--

In the Drawings

In sheet 15 of 30, FIG. 16C, "INTERACALATED" should read --INTERCALATED--

In the Specification

Column 4, Line 28, "probes:" should read --probes;--

Column 4, Line 32, "bioreceptors:" should read --bioreceptors;--

Column 7, Line 16, "napththoquinones," should read --naphthoquinones,--

Column 7, Line 21, "anthroquinones," should read --anthraquinones,--

Column 9, Line 9, "edt/" should read --edu/--

Column 11, Line 34, "Rivera." should read --Rivera,--

Column 11, Line 43, "El-Saved." should read --El-Sayed,--

Column 11, Line 44, "Science." should read --Science,--

Column 13, Line 13 (approx.), "cyotoxic" should read --cytotoxic--

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,201,796 B2

Column 13, Lines 32-33, "Letters. 16(10). pp." should read --Letters, 16(10), pp.--

Column 13, Line 53, "Then." should read --Then,--

Column 16, Line 42, "necessan," should read --necessary--

Column 16, Line 65, "IR" should read --IR,--

Column 18, Line 24, "Vo-Dinh." should read --Vo-Dinh,--

Column 18, Line 25, "Moody." should read --Moody,--

Column 18, Line 27, "analysis."" should read --analysis,"--

Column 18, Line 54, "plasmons."" should read --plasmons,"--

Column 18, Line 66, "plasmons."" should read --plasmons,"--

Column 19, Line 51, "6C." should read --6C,--

Column 19, Line 65, "17.557" should read --17,557--

Column 20, Line 5, "analysis."" should read --analysis,"--

Column 20, Line 17, "Westcoit," should read --Westcott,--

Column 20, Line 21, "S J." should read --S. J.--

Column 20, Line 21, "Vo-Dinh." should read --Vo-Dinh,--

Column 20, Line 37, "Vo-Dinh." should read --Vo-Dinh,--

Column 21, Line 1, "polycarpolactone" should read --polycaprolactone--

Column 21, Line 5, "poly(ether)(ster)" should read --poly(ether)(ester)--

Column 22, Line 48, "3781-6]" and insert --3781-6],--

Column 24, Line 19, "radiology." should read --radiology,--

Column 25, Line 33, "1997" should read --1997,--

Column 25, Line 50, "Chen." should read --Chen,--

Column 25, Line 50, "Liu." should read --Liu,--

Column 25, Lines 52-53, "multilabels." should read --multilabels,--

Column 25, Line 53, "10(2," should read --10(2),--

Column 26, Line 43, ".XAbZ." should read --.XAFZ,--

Column 26, Line 43, "Phys." should read --Phys,--

Column 26, Line 47, "Aoyagi." should read --Aoyagi,--

Column 26, Lines 49-50, "luminescence." should read --luminescence,--

Column 27, Line 57, "Letter. VOLUME 91." should read --Letter, VOLUME 91,--

Column 28, Line 32, "apoferrtin" should read --apoferritin--

Column 28, Line 45, "statistics:" should read --statistics;--

Column 28, Line 52, "Nikl." should read --Nikl,--

Column 28, Line 53, "x-rays." should read --x-rays,--

Column 29, Line 14, "[Kadshchuk." should read --[Kadshchuk,--

Column 29, Line 14, "Ostapenko." should read --Ostapenko,--

Column 29, Line 26, "Izvekov." should read --Izvekov,--

Column 29, Line 26, "Sugakov." should read --Sugakov,--

Column 29, Line 62, "hydrocarbons." should read --hydrocarbons,--

Column 30, Line 5, "Vo-Dinh." should read --Vo-Dinh,--

Column 30, Line 6, "spectrometry" should read --spectrometry,--

Column 30, Line 46, "Mugnier." should read --Mugnier,--

Column 30, Line 48, "Semiconductor." should read --Semiconductor,--

Column 30, Line 50, delete "ahs" should read --has--

Column 30, Lines 57-58, "Govorov." should read --Govorov,--

Column 30, Line 58, "Skeini." should read --Skeini,--

CERTIFICATE OF CORRECTION (continued)
U.S. Pat. No. 10,201,796 B2

Column 30, Line 60, "Naik." should read --Naik,--

Column 30, Line 61, "Assemblies." should read --Assemblies,--

Column 30, Line 62, "6." should read --6,--

Column 31, Line 36, "Evans." should read --Evans,--

Column 31, Line 40, "Hvbridized" should read --Hybridized--

Column 32, Line 35, "photoactivation." should read --photoactivation,--

Column 33, Line 36, "Govorov." should read --Govorov,--

Column 33, Line 39, "Effects." should read --Effects,--

Column 34, Line 40, "C." should read --C,-- (2nd occurrence)

Column 34, Lines 40-41, "microcavities." should read --microcavities,--

Column 34, Line 67, "6782-6786" should read --6782-6786,--

Column 35, Line 13, "Schifrin." should read --Schiffrin,--

Column 35, Line 20, "E;" should read --E.;--

Column 35, Line 21, "J; Strokes. J. J;" should read --J.; Strokes, J. J.;--

Column 35, Line 22, "Porter." should read --Porter,--

Column 35, Line 23, "17" should read --17,--

Column 35, Line 28, "Calls," should read --Calis,--

Column 35, Line 29, "Reed." should read --Reed,--

Column 35, Line 34, "W;" should read --W.;--

Column 35, Line 39, "Letters 2003." should read --Letters; 2003,--

Column 35, Line 49, "DYES." should read --DYES,--

Column 35, Line 50, "13." should read --13,--

Column 36, Line 67, "$BaFBr:Tb_{3+}$;" should read --$BaFBr:Tb^{3+}$;--

CERTIFICATE OF CORRECTION (continued)
U.S. Pat. No. 10,201,796 B2

Column 37, Line 12, "Asian" should read --Aslan--

Column 37, Line 18, "Asian" should read --Aslan--

Column 38, Line 15, "RbMnCl$_3$." should read --RbMnCl$_3$,--

Column 38, Line 27, "emission)." should read --emission),--

Column 38, Line 41, "Cd$_{1-x}$MnTe$_y$," should read --Cd$_{1-x}$Mn$_x$Te$_y$,--

Column 38, Line 62, "ZnS:Mn,Er$^+$" should read --ZnS:Mn, Er$^{3+}$--

Column 40, Line 29 (approx.), "BaFBr:Eu$^2$," should read --BaFBr:Eu$^{2+}$,--

Column 41, Line 20, "119=17" should read --119±17--

Column 42, Line 18, "actived" should read --activated--

Column 42, Line 25, "rhodamine." should read --rhodamine,--

Column 42, Line 33, "anthroquinones." should read --anthraquinones.--

Column 43, Line 54, "(O$_2$)" should read --(O$_{2-}$)--

Column 48, Line 2, "(4-vinvlphenyl)" should read --(4-vinylphenyl)--

Column 48, Line 17, "camphoquinone," should read --camphorquinone,--

Column 49, Line 3, "SPHEREICEL" should read --SPHERICAL--

Column 50, Line 31, "particular." should read --particular,--

Column 51, Line 15, "cured" should read --cured.--

Column 54, Line 25, "modern" should read --modem--

Column 56, Line 60, "anthroquinones." should read --anthraquinones.--

Column 57, Lines 7-8, "chemilumiscent" should read --chemiluminescent--

Column 57, Line 55, "gaent" should read --agent--

Column 58, Line 1, "camphoquinone," should read --camphorquinone,--

Column 58, Lines 51-52, "chemilumiscent" should read --chemiluminescent--

CERTIFICATE OF CORRECTION (continued)
U.S. Pat. No. 10,201,796 B2

Column 65, Line 35, "naonoparticles." should read --nanoparticles.--

Column 66, Line 14, "Wenneng" should read --Wenneng,--

Column 66, Line 17, "Robinson." should read --Robinson,--

Column 66, Line 45, "Leygraf." should read --Leygraf,--

Column 66, Line 47, "Tanner." should read --Tanner,--

Column 67, Line 41, "phihalocyanine" should read --phthalocyanine--

Column 67, Line 49, "Cotton." should read --Cotton,--

Column 68, Line 23, "M." should read --M.,--

Column 68, Line 26, "43." should read --43,--

Column 69, Line 14, "Plasmonica-active" should read --Plasmonics-active--

Column 69, Line 25, "Wokaun." should read --Wokaun,--

Column 69, Line 44, "quartz," should read --quartz--

Column 70, Line 24, "tithography," should read --lithography,--

Column 70, Line 30, "nanoimprinting" should read --nanoimprinting.--